US011041867B2

(12) United States Patent
Wilson et al.

(10) Patent No.: US 11,041,867 B2
(45) Date of Patent: Jun. 22, 2021

(54) PROADM AND/OR HISTONES AS MARKERS INDICATING AN ADVERSE EVENT

(71) Applicant: B.R.A.H.M.S GmbH, Hennigsdorf (DE)

(72) Inventors: Darius Cameron Wilson, Berlin (DE); Jesus Bermejo, Soria (ES); David Andaluz, Soria (ES); Dolores Calvo, Soria (ES)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

(21) Appl. No.: 16/480,546

(22) PCT Filed: Feb. 1, 2018

(86) PCT No.: PCT/EP2018/052499
§ 371 (c)(1),
(2) Date: Jul. 24, 2019

(87) PCT Pub. No.: WO2018/141840
PCT Pub. Date: Aug. 9, 2018

(65) Prior Publication Data
US 2020/0081018 A1  Mar. 12, 2020

(30) Foreign Application Priority Data

Feb. 2, 2017 (EP) .................................... 17154348

(51) Int. Cl.
*G01N 33/68* (2006.01)
*G01N 33/53* (2006.01)

(52) U.S. Cl.
CPC .......... *G01N 33/6893* (2013.01); *G01N 33/53* (2013.01); *G01N 2800/26* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

WO    2010040564 A1    4/2010
WO    2010054810 A1    5/2010

OTHER PUBLICATIONS

PCT International Search Report for PCT/EP2018/052499, dated Mar. 21, 2018.
Werner C Albrich et al: "Enhancement of CURB65 score with proadrenomedullin (CURB65-A) for outcome prediction in lower respiratory tract infections: Derivation of a clinical algorithm", BMC Infectious Diseases, Biomed Central, London, GB, vol. II, No. 1, (May 3, 2011) p. 112.
Andaluz-Ocheda et al: "Sustained value of proadrenomedullin as mortality predictor in severe sepsis", Journal of Infection, vol. 71, No. I, (Feb. 19, 2015), pp. 136-139.
Akpinar et al: "Performance evaluation of MR-proadrenomedullin and other scoring systems in severe sepsis with pneumonia", Journal of thoracic disease, Jul. 1, 2014 (Jul. 1, 2014), p. 921.
Cicuendez R et al: "Prognostic Value of Proadrenomedulin in Severe Sepsis and Septic Shock is Independent of Etiology and Focus of Infection", Intensive Care Medicine Experimental, Biomed Central Ltd, London, UK, vol. 3, No. I, (Oct. 1, 2015) , pp. 1-2.
Cicuendez R et al: "Sustained prognostic value of proadrenomedulin in severe sepsis and septic shock", Intensive Care Medicine Experimental, Biomed Central Ltd, London, UK, vol. 3, No. 1, (Oct. 1, 2015) , p. 1.
Rossella Marino et al: "Plasma adrenomedullin is associated with short-term mortality and vasopressor requirement in patients admitted with sepsis", Critical Care, Biomed Central Ltd., London, GB, vol. 18, No. I, (Feb. 17, 2014), p. R34.
Christ-Crain Mirjam et al: "Mid-regional pro-adrenomedullin as a prognostic marker in sepsis: an observational study", Critical Care, Biomed Central Ltd., London, GB, vol. 9, No. 6, (Nov. 15, 2005), pp. R816-R824.
Wang R L et al: "Prediction about severity and outcome of sepsis by pro-atrial natriuretic peptide and pro-adrenomedullin", Chinese Journal of Traumatology English Edition, Elsevier, Amsterdam, NL, vol. 13, No. 3, (Jun. 1, 2010), pp. 152-157.
Andaluz-Ocheda et al: "Superior accuracy ofmid-regional proadrenomedullin formortality prediction insepsis withvarying levels ofillness severity", Intensive Care, (Feb. 10, 2017), p. 15.

*Primary Examiner* — Padmavathi Baskar
(74) *Attorney, Agent, or Firm* — McBee Moore & Vanik IP, LLC

(57) ABSTRACT

The present invention relates to diagnosis, prognosis, risk assessment, and/or risk stratification of an adverse event, particularly mortality, of a subject. The invention relates to a method that comprises determining a level of proadrenomedullin (proADM) in a sample of said subject, and wherein said level of proADM is indicative of said adverse event of said subject, wherein said level of proADM is compared to a reference level of proADM; and wherein said adverse event of said subject is identified based on the comparison. The invention further relates to kits for carrying out the methods of the invention.

Figure 1:
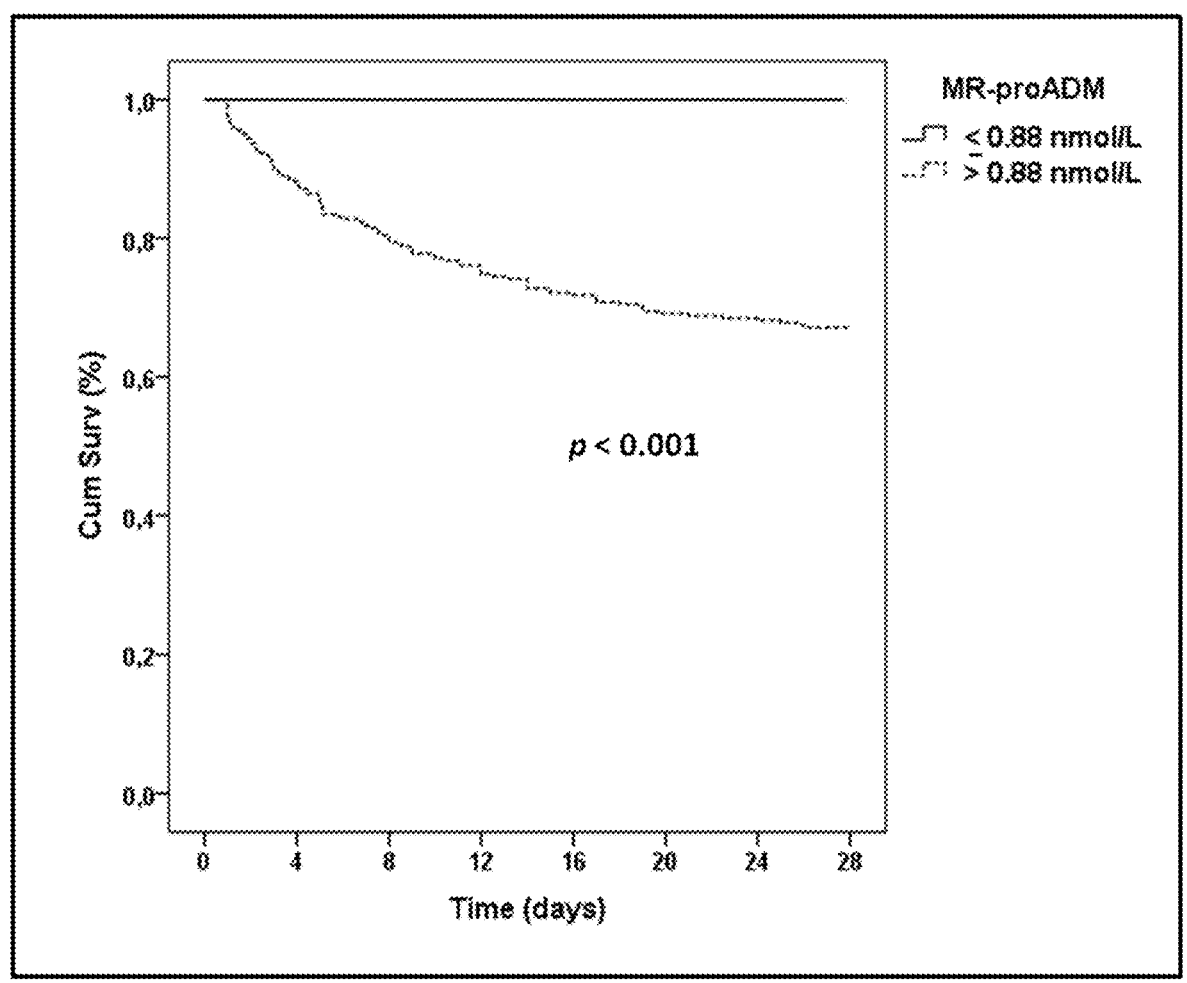

9 Claims, 4 Drawing Sheets
Specification includes a Sequence Listing.

SEQUENCE LISTING

```
<160> NUMBER OF SEQ ID NOS: 16

<210> SEQ ID NO 1
<211> LENGTH: 102
<212> TYPE: PRT
<213> ORGANISM: Homo sapiens
<220> FEATURE:
<221> NAME/KEY: MISC_FEATURE
<222> LOCATION: (1)..(102)
<223> OTHER INFORMATION: amino acid sequence of human histone H4,
      uniprot ID P62805.2, initial methionine not included

<400> SEQUENCE: 1

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
    50                  55                  60

Val Ile Arg Asp Ala Val Thr Tyr Thr Glu His Ala Lys Arg Lys Thr
65                  70                  75                  80
```

```
Val Thr Ala Met Asp Val Val Tyr Ala Leu Lys Arg Gln Gly Arg Thr
                85                  90                  95

Leu Tyr Gly Phe Gly Gly
            100

<210> SEQ ID NO 2
<211> LENGTH: 130
<212> TYPE: PRT
<213> ORGANISM: Homo sapiens
<220> FEATURE:
<221> NAME/KEY: MISC_FEATURE
<222> LOCATION: (1)..(130)
<223> OTHER INFORMATION: amino acid sequence of human histone H2A type
      1, uniprot ID Q96QV6, initial methionine not included

<400> SEQUENCE: 2

Ser Gly Arg Gly Lys Gln Gly Gly Lys Ala Arg Ala Lys Ser Lys Ser
1               5                   10                  15

Arg Ser Ser Arg Ala Gly Leu Gln Phe Pro Val Gly Arg Ile His Arg
            20                  25                  30

Leu Leu Arg Lys Gly Asn Tyr Ala Glu Arg Ile Gly Ala Gly Ala Pro
        35                  40                  45

Val Tyr Leu Ala Ala Val Leu Glu Tyr Leu Thr Ala Glu Ile Leu Glu
    50                  55                  60

Leu Ala Gly Asn Ala Ser Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Gly Gly Val Thr Ile Ala Gln Gly Gly Val Leu Pro Asn Ile Gln
            100                 105                 110

Ala Val Leu Leu Pro Lys Lys Thr Glu Ser His His His Lys Ala Gln
        115                 120                 125

Ser Lys
    130

<210> SEQ ID NO 3
<211> LENGTH: 135
<212> TYPE: PRT
<213> ORGANISM: Homo sapiens
<220> FEATURE:
<221> NAME/KEY: MISC_FEATURE
<222> LOCATION: (1)..(135)
<223> OTHER INFORMATION: amino acid sequence of human histone H3.1,
      uniprot ID P68431.2, initial methionine not included

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110
```

His Ala Lys Arg Val Thr Ile Met Pro Lys Asp Ile Gln Leu Ala Arg
        115                 120                 125

Arg Ile Arg Gly Glu Arg Ala
        130                 135

<210> SEQ ID NO 4
<211> LENGTH: 126
<212> TYPE: PRT
<213> ORGANISM: Homo sapiens
<220> FEATURE:
<221> NAME/KEY: MISC_FEATURE
<222> LOCATION: (1)..(126)
<223> OTHER INFORMATION: amino acid sequence of human histone H2B,
      uniprot ID P62807

<400> SEQUENCE: 4

Met Pro Glu Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

<210> SEQ ID NO 5
<211> LENGTH: 185
<212> TYPE: PRT
<213> ORGANISM: Homo sapiens
<220> FEATURE:
<221> NAME/KEY: MISC_FEATURE
<222> LOCATION: (1)..(185)
<223> OTHER INFORMATION: amino acid sequence of pre-pro-ADM

<400> SEQUENCE: 5

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
                20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

```
Asp Lys Asp Lys Asp Asn Val Ala Pro Arg Ser Lys Ile Ser Pro Gln
        130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 6
<211> LENGTH: 48
<212> TYPE: PRT
<213> ORGANISM: Homo sapiens
<220> FEATURE:
<221> NAME/KEY: MISC_FEATURE
<222> LOCATION: (1)..(48)
<223> OTHER INFORMATION: amino acid sequence of MR-proADM (AS 45-92 of
      pre-pro-ADM)

<400> SEQUENCE: 6

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45

<210> SEQ ID NO 7
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: position 21-29 of SEQ ID NO:2

<400> SEQUENCE: 7

Ala Gly Leu Gln Phe Pro Val Gly Arg
1               5

<210> SEQ ID NO 8
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: amino acid sequence of residues 82-88 of SEQ ID
      NO:2

<400> SEQUENCE: 8

His Leu Gln Leu Ala Ile Arg
1               5

<210> SEQ ID NO 9
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: amino acid sequence of residues 89-95 of SEQ ID
      NO:2

<400> SEQUENCE: 9
```

-continued

```
Asn Asp Glu Glu Leu Asn Lys
1               5

<210> SEQ ID NO 10
<211> LENGTH: 19
<212> TYPE: PRT
<213> ORGANISM: Homo sapiens
<220> FEATURE:
<221> NAME/KEY: MISC_FEATURE
<222> LOCATION: (1)..(19)
<223> OTHER INFORMATION: amino acid sequence of residues 100-118 of SEQ
      ID NO:2

<400> SEQUENCE: 10

Val Thr Ile Ala Gln Gly Gly Val Leu Pro Asn Ile Gln Ala Val Leu
1               5                   10                  15

Leu Pro Lys

<210> SEQ ID NO 11
<211> LENGTH: 57
<212> TYPE: PRT
<213> ORGANISM: Homo sapiens
<220> FEATURE:
<221> NAME/KEY: MISC_FEATURE
<222> LOCATION: (1)..(57)
<223> OTHER INFORMATION: amino acid sequence of residues 46-102 of SEQ
      ID NO:1

<400> SEQUENCE: 11

Ile Ser Gly Leu Ile Tyr Glu Glu Thr Arg Gly Val Leu Lys Val Phe
1               5                   10                  15

Leu Glu Asn Val Ile Arg Asp Ala Val Thr Tyr Thr Glu His Ala Lys
            20                  25                  30

Arg Lys Thr Val Thr Ala Met Asp Val Val Tyr Ala Leu Lys Arg Gln
        35                  40                  45

Gly Arg Thr Leu Tyr Gly Phe Gly Gly
    50                  55

<210> SEQ ID NO 12
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: amino acid sequence of residues 46-55 of SEQ ID
      NO:1

<400> SEQUENCE: 12

Ile Ser Gly Leu Ile Tyr Glu Glu Thr Arg
1               5                   10

<210> SEQ ID NO 13
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: amino acid sequence of residues 60-67 of SEQ ID
      NO:1

<400> SEQUENCE: 13

Val Phe Leu Glu Asn Val Ile Arg
1               5
```

```
<210> SEQ ID NO 14
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: amino acid sequence of residues 80-91 with
      acetylated K91 of SEQ ID NO:1

<400> SEQUENCE: 14

Thr Val Thr Ala Met Asp Val Val Tyr Ala Leu Lys
1               5                   10

<210> SEQ ID NO 15
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: amino acid sequence of residues 24-35 of SEQ ID
      NO:1

<400> SEQUENCE: 15

Asp Asn Ile Gln Gly Ile Thr Lys Pro Ala Ile Arg
1               5                   10

<210> SEQ ID NO 16
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: amino acid sequence of residues 68-77 of SEQ ID
      NO:1

<400> SEQUENCE: 16

Asp Ala Val Thr Tyr Thr Glu His Ala Lys
1               5                   10
```

PROADM AND/OR HISTONES AS MARKERS INDICATING AN ADVERSE EVENT

CROSS-REFERENCE TO RELATED APPLICATIONS

This application is a National Stage entry of International Application No. PCT/EP2018/052499, filed Feb. 1, 2018, which claims priority to European Patent Application No. 17154348.1, filed Feb. 2, 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence Listing 2905193-029000 ST25" created on 24 Jul. 2019 and 10,881 bytes in size) is submitted concurrently with the instant application, and the entire contents of the Sequence Listing are incorporated herein by reference.

BACKGROUND

Field

The present invention relates to diagnosis, prognosis, risk assessment, and/or risk stratification of an adverse event, particularly mortality, of a subject. The invention relates to a method that comprises determining a level of proadrenomedullin (proADM) in the sample of the subject, and wherein the level of proADM is indicative of the adverse event of said subject and/or determining a level of at least one histone, particularly histone H2B, H4, H2A and/or H3, in a sample of the subject, and wherein the level of at least one histone is indicative of the adverse event of said subject. The invention further relates to kits for carrying out the methods of the invention.

Description of Related Art

The intensive care unit (ICU) in a hospital is usually the unit with the most critically ill patients and the highest mortality rates (Kaneko-Wada Fde, Dominguez-Cherit et al. 2015). It is a very expensive component for any healthcare system, mainly due to long stays on the ICU, modern and costly technologies and the overall complexity of intensive care (Halpern and Pastores 2010). Despite high efforts of intensive care medicine, mortality rates on ICUs range from 6.4% up to 40%, depending on the analyzed patient population and their status of severity (Mayr, Dunser et al. 2006). Major causes of adverse outcome and death on the ICU are related to failing organs like the multiple organ dysfunction syndrome (MODS) and to sepsis (Vincent 2008; Ferreira and Sakr 2011). For the sub-group of septic patients, the mortality rate in Europe is even higher, ranging between 27% and 54% (Vincent 2008).

In order to identify high risk patients with adverse or fatal event/outcomes (i), to help clinicians in early decisions after ICU admission (ii), to optimize clinical treatments and resources (iii) and finally to decrease ICU mortality (iv), knowledge about determinant parameters like short- and long-term outcomes are of high value (Mayr, Dunser et al. 2006). Up to now, severity scores are mostly used for risk and severity assessment as well as outcome prediction of critically ill patients. Predominant ICU scoring systems are the acute physiology and chronic health evaluation (APACHE) score, the simplified acute physiology score (SAPS) and the sequential organ failure assessment (SOFA) score, based on 17, 14 or 6 physiology or organ specific parameters, respectively (Bouch and Thompson 2008). Despite their ability to predict a patient's outcome, such scores also have various disadvantages. For example, each single parameter of the scores has to be assessed and evaluated. Therefore, the determination of the results of the scores is time consuming (1 day), which is particularly disadvantageous in ICU care where fast tests are highly appreciated. Furthermore, such scores are dependent on the subjectivity of every assessing clinician, need to be recalibrated frequently and rely on several parameters to be individually determined.

Accordingly, there is a need of simple, fast and objective criteria for the diagnosis, prognosis, risk assessment, and/or risk stratification of an adverse event in a subject, particularly in a critically ill subject.

Therefore, the technical problem underlying the invention is the provision of means and methods to provide a fast and reliable way to predict an adverse event, particularly a fatal event, e.g. mortality/death, of a subject.

The technical problem is solved by provision of the embodiments provided herein below and as characterized in the appended claims.

Summary

The invention relates to a method for the diagnosis, prognosis, risk assessment, and/or risk stratification of an adverse event of a subject, wherein said method comprises determining a level of proadrenomedullin (proADM) in a sample of said subject, and wherein said level of proADM or said fragment thereof is indicative of said adverse event of said subject.

Further, the invention relates to a method for the diagnosis, prognosis, risk assessment, and/or risk stratification of an adverse event of a subject, wherein said method comprises determining a level of at least one histone or a fragment thereof in a sample of said subject, and wherein said level of at least one histone or said fragment thereof is indicative of said adverse event of said subject.

Further, the invention relates to a method for the diagnosis, prognosis, risk assessment, and/or risk stratification of an adverse event of a subject, wherein said method comprises determining a level of at least one histone and a level of proadrenomedullin (proADM) and/or fragment(s) thereof in a sample of said subject, and wherein said level of at least one histone and said level of proADM and/or said fragment(s) thereof are indicative of said adverse event of said subject. As used herein, "proADM" also encompasses fragments such as MR-proADM and mature ADM unless stated otherwise.

DETAILED DESCRIPTION OF A PREFERRED EMBODIMENT

The present invention solves the above identified technical problem. As documented herein below and in the appended examples, it was unexpectedly found in a clinical study that the levels of at least one histone, particularly histone H2B, H4, H2A and H3, and/or the level of proADM, particularly MR-proADM, demonstrate(s) a strong statistical relationship with an adverse event, e.g. mortality, of the subjects; see illustrative Example 1. Accordingly, it is documented herein that said at least one histone protein and/or said proADM, e.g. MR-proADM, can be used as a marker for the prediction of an adverse event. In particular, the examples document that such markers can be employed for the prediction of a survivor or non-survivor, i.e. mortality of the subject.

In the appended examples, it was surprisingly demonstrated that a level of proADM (particularly of MR-proADM) of the subject of less than or equal to about a reference level, e.g. about 0.9 nmol/L, indicates that the adverse does not occur within about 28 days. A reference level of about 0.9 nmol/L of proADM provides a sensitivity of 100% in identifying non-survivors, i.e. a level below this threshold reliably identifies patients that will survive within the 28 day period. A reference level of about 1.8 nmol/L for proADM also predicts reliably the adverse event, e.g. mortality, in the appended examples. Accordingly, the level of proADM indicates whether the subject will survive or not, e.g. within about 28 days.

It was further demonstrated that proADM (particularly MR-proADM) is reliable to discriminate non-survivors or survivors if the subjects were stratified by the severity of the disease and/or condition, e.g. organ failure. The predictive method works in principal for subjects having any number of organ failures, i.e. for any SOFA score. The detection of the level of proADM (particularly MR-proADM) allows the identification of non-survivors in all the severity groups i.e. for any SOFA score. This is particularly important for the less severely ill patients (SOFA score <6), since this group represents either the earliest presentation in the clinical course of sepsis and/or the less severe form of this disease in the clinical (particularly ICU or ED) setting. Thus, proADM (particularly MR-proADM) is a reliable marker for early sepsis management, since it provides a rapid prognostic value and help to guide diagnostic interventions and treatment decisions. It is shown in the appended examples that the subjects can be classified in less severely ill subjects (e.g. a SOFA score 6), moderately severe ill subjects (e.g. a SOFA score of 7 to 12), or severely ill subjects (e.g. a SOFA score 13). Accordingly, the subjects can be classified based on the SOFA score. The predictive value of proADM (particularly MR-proADM) can be improved by combining it with the determination of the SOFA score of a subject. However, the predictive value of this marker is such that the determination of the SOFA score is not required; in other words in some aspects of the method of the invention, the level of proADM (preferably MR-proADM) of a subject is determined but the SOFA score is not determined. In the appended examples, it was shown that the level of proADM (particularly MR-proADM) shows the best performance among the tested markers in case of subjects with a low degree of disease severity (less severely ill subjects). Such subjects may have a SOFA score of 6. In particular, it was demonstrated that the level of proADM (particularly MR-proADM) of less severely ill subjects that is lower than the reference level of about 1.8 nmol/L indicates that the adverse event does not occur, particularly mortality, within about 28 days; see Example 2, Table 9. Further, proADM is also advantageous in the prediction of the adverse event compared to other markers, such as lactate, in case of moderately severe diseased subjects. Such subjects may have a SOFA score of 7 to 12. In particular, it was demonstrated that the level of proADM of moderately severe ill subjects that is lower than the reference level of about 3.2 nmol/L indicates that the adverse event does not occur, particularly mortality, within about 28 days; see Example 2, Table 9. Finally, the level of proADM also reliably predicts an adverse event of severely ill subjects. In particular, it was demonstrated that the level of proADM of severely ill subjects that is lower than the reference level of 5.6 nmol/L indicatives that the adverse event does not occur, particularly mortality, within about 28 days; see Example 2, Table 9.

Accordingly, the level of proADM (particularly MR-proADM) predicts the risk of the subject and thus helps the clinician in the decision which therapy is most suitable. Therefore, the level of proADM improves the treatment of patient in the clinic. Hence, the level of proADM may also be used in the intensive care unit management, particularly to identify subjects that do not need further intensive care, e.g. treatment in the ICU or the Emergency Department (ED). In particular, a proADM reference value lower than about 0.9 nmol/L (preferably 0.88 nmol/L) allows to "rule out" mortality in the 28 days following admission to the ICU or ED. This cut-off is therefore useful for guiding early clinical decisions, when the clinical signs of overt organ failure are not yet apparent. Hence, the method of the invention can be used for this purpose. The identification of subjects that do not require (further) intensive care (e.g. in the ICU or ED) but can for example be transferred to a general ward reduces costs for the cost-bearer and frees beds in the ICU or ED. In a specific aspect, the method of the invention is used to predict the mortality or stratify subjects in which the clinical signs of organ failure have not yet manifested (e.g. patients corresponding to subjects having a low SOFA score such as 6, preferably 4, more preferably 3).

In addition, is shown in the appended examples that the level of proADM (particularly MR-proADM) can also be used to modify the SOFA score of said subject. For example, the SOFA can be adapted, e.g. increased, based on the level of proADM of said subject, and wherein said modified SOFA score is indicative of said adverse event.

In particular, the SOFA score of the subject may be increased by one if the subject has a proADM level that is higher than about 1.8 nmol/L. Such a modified SOFA score further improves the prediction; see e.g. Example 2.

Instead or in addition to the SOFA score, also the quick SOFA (qSOFA) score can be determined.

In the appended examples, it is also surprisingly demonstrated that the level of the at least one histone, particularly H2B, H4, H2A and H3, is strongly associated with the adverse event, e.g. mortality, of the subject. In particular, the appended examples demonstrate that the levels of the histones are statistically associated with the adverse event, e.g. mortality, occurring within about 28 days, within about 7 days or within about 3 days. The appended examples revealed that an increase of the level of the marker indicate that the adverse event, e.g. mortality, occurs in the subject; see appended Example 1, e.g. Table 1 to 6. Moreover, the levels of the histones demonstrated to be particularly correlated to short adverse events, e.g. occurring within 7 days or 3 days. Furthermore, the level of the at least one histone in a sample of subjects suffering from respiratory disease was found to be correlated with the adverse event, e.g. mortality, occurring within 7 days; see e.g. table 4. In addition, the level of the at least one histone in a sample of the subjects suffering from urinary tract infection was found to be correlated with the adverse event, e.g. mortality, occurring within 28 days; see e.g. table 5. Moreover, the level of the at least one histone in a sample of the subject suffering from malignancies was found to be correlated with the adverse event, e.g. mortality, occurring within 28 days; see e.g. table 6.

In addition, it is also surprisingly demonstrated in the appended examples that the level of proADM, e.g. the level of the fragment MR-proADM, is strongly correlated with the adverse event, e.g. mortality, of the subject. In particular, the appended examples demonstrate that the level of proADM is statistically associated with the adverse event, e.g. mortality, occurring within about 28 days, within about 7 days or within about 3 days; see e.g. Tables 2 and 3. Particularly, the appended examples document that the level of proADM are indicative of the adverse event, e.g. mortality, occurring within 28 days or occurring within 7 days; see e.g. Tables 2 and 3.

In addition, it is documented in the appended examples that the prediction is further improved if a combination of the levels of the markers is determined. In particular, the determination of the level of at least one histone in addition to the level of proADM further improved the prognosis of the adverse event, e.g. mortality; see tables 1 to 3. It is documented in the appended examples that the determination of a level of a further marker and/or parameter in addition to the level of at least one histone or of proADM further improves the prediction of the adverse event, e.g. mortality; see illustrative tables 1 to 3. For example, it is demonstrated in the appended examples that determining a clinical score also improves the prediction based on the level of proADM or the histones. Also, the determination of the level of a biomarker, such as aldolase B, improves the prediction based on the level of proADM or the histones. Accordingly, the invention also relates to a method comprising determining the level of a further marker and/or parameter, i.e. the use of marker panels.

The present invention has, inter alia, the following advantages over the conventional methods: the inventive methods and the kits are fast, objective, easy to use and precise for the prediction of an adverse event: The methods and kits of the invention relate to markers that are easily measurable in routine in hospitals because the levels of histones and of proADM can be determined in routinely obtained blood samples or further biological fluids obtained from a subject. In addition, the determination of the levels of the histones or proADM is very fast. Therefore, the methods and the kits of the invention are suitable for a quick assessment, and diagnosis and prognosis of an adverse event, e.g. mortality. Accordingly, the quick determination also is suitable for a fast treatment decision avoiding or reducing the risk of occurrence of the adverse event. Furthermore, due to the simple outcome of a biomarker measurement as one specific value, there is no subjective bias of medical staff when using this method or the kits of the invention. The reproducibility is thus improved compared to subjective scoring for physiological parameters as, for example, employed in the SOFA score. The level of the histone or proADM can also be combined with further marker(s) and/or parameter(s), e.g. clinical scores, such as SOFA score, in order to further improve the prediction and to adapt the analysis to specific sensitivities and specificities for evaluating the overall status of critical ill patients.

Accordingly, the herein provided methods and kits are advantageous in the diagnosis, prognosis, risk assessment, and/or risk stratification of an occurring adverse event, e.g. mortality/death, of a subject.

As documented herein above and in the appended examples, the level of histones and the level of proADM were surprisingly found to correlate with an adverse event, such as mortality, in subjects. Accordingly, the invention relates to methods and kits for the diagnosis, prognosis, risk assessment, and/or risk stratification of the adverse event, particularly mortality, of a subject. Further, the invention relates to methods and kits for monitoring, therapy guidance and/or therapy control of subjects, wherein the level of the at least one histone and/or of proADM is indicative of the adverse event, particularly mortality. The definitions provided herein above and below also apply to such aspects.

In particular, the invention relates to a method for the diagnosis, prognosis, risk assessment, and/or risk stratification of an adverse event, particularly mortality, of a subject, wherein said method comprises (i) determining a level of at least one histone in a sample of said subject, and wherein said level of at least one histone is indicative of said adverse event, particularly mortality, of said subject; and/or (ii) determining a level of proadrenomedullin (proADM) in a sample of said subject, and wherein said level of proADM is indicative of said adverse event, particularly mortality, of said subject.

As used herein, the term "determining the level of at least one histone" or the like refers to determining a level of a histone or a fragment thereof in a sample of the subject or determining a level of more than one histones or fragments thereof in the sample of the subject. Particularly, "determining the level of at least one histone" may refer to determining a level of a histone in the sample of the subject, wherein preferably the histone is selected from the group consisting of histone H2B, H4, H2A and H3. Particularly, the level of the histone H2B is determined. Further, "determining the level of at least one histone" may refer to determining a level of a histone in the sample of the subject, wherein particularly the level of the histone H4 is determined. Further, "determining the level of at least one histone" may refer to determining a level of two histones in the sample of the subject, wherein preferably the levels of the histones H2B and H4 are determined. Further, "determining the level of at least one histone" may refer to determining a level of three histones in the sample of the subject, wherein preferably the levels of the histones H2B, H4, and H2A are determined. Further, "determining the level of at least one histone" may refer to determining a level of four histones in the sample of the subject, wherein preferably the levels of the histones H2B, H4, H2A and H3 are determined.

Accordingly, in the context of the present invention, "determining the level of at least one histone" may refer to determining a level of histone H2B, a level of histone H4, a level of histone H2A and/or a level of histone H3.

In particular, the term "determining the level of at least one histone" or the like may refer to determining a level of a histone in the sample of the subject. Accordingly, the invention also relates to a method for the diagnosis, prognosis, risk assessment, risk stratification, and/or monitoring of an adverse event of a subject, wherein said method comprises determining a level of a histone or a fragment thereof in a sample of said subject and wherein said level of a histone or said fragment thereof is indicative of said adverse event, particularly mortality.

As used herein, "histone" or "histone protein", or "histones" or "histone proteins" refers to the canonical histone(s), such as H1, H2A, H2B, H3 or H4, as well as histone variant(s), such as H3.3, H2A.Z etc. or fragment(s) thereof. Histones form the octamer particle around which DNA is wrapped in order to assemble the chromatin structure (Luger, Nature. 1997 Sep. 18; 389(6648):251-60). For example, the histone proteins H2A, H2B, H3, and H4 (two of each) form an octamer, which is wrapped by 165 base pairs of DNA to form the fundamental subunit of chromatin, the nucleosome. Histones are also detected outside the nucleus in multiple pathophysiological processes (WO 2009/061918). The presence of extracellular histones has been described in the blood of patients suffering from different etiologies involving inflammatory processes. Histone release from activated immune cells can be mediated by extracellular traps. Activated neutrophils, as an ultimate mechanism of controlling and clearing an infection, can release extracellular fibers, so called neutrophile extracellular traps (NETs) (Brinkmann V., et al. Science 2004; 303 (5663): p. 1532-5). Other mechanisms by which histones may be released into a patient's blood stream include apoptosis, necrosis, pyroptosis or necroptosis of cells.

In particular, the at least one histone is selected from the group consisting of H2B, H4, H2A and H3. Accordingly, the level of the histone to be determined in the methods and kits of the invention is particularly a level of the histones(s) H2B, H4, H2A and/or H3. The sequences of the histones are known to the skilled person. Exemplary sequences of the histones are given in SEQ ID NOs: 1 to 4. The exemplary amino acid sequence of histone H4 is given in SEQ ID NO: 1. The exemplary amino acid sequence of histone H2A is given in SEQ ID NO: 2. The exemplary amino acid sequence of histone H3 is given in SEQ ID NO: 3. The exemplary amino acid sequence of histone H2B is given in SEQ ID NO: 4. Particularly, the at least one histone is selected from the group consisting of H2B, H4, H2A and H3. More particularly, the at least one histone is selected from the group consisting of H2B, H4 and H2A. More particularly, the at least one histone is H2B and H4. More particularly, the at least one histone is H2B or H4.

It is understood that "determining the level of at least one histone" or the like refers to determining the level of at least one histone or a fragment of the at least one histone in the sample. In particular, the level of the histone H2B, H4, H2A, and/or H4 is determined in the sample. Accordingly, the at least one histone determined in the sample can be a free histone or the at least one histone determined in the sample can occur and can be assembled in a macromolecular complex, for example, in the octamer, nucleosome and/or NETs. Therefore, the level of at least one histone in the sample can comprise the level of free histone protein and/or histone protein assembled in a macromolecular complex.

In particular aspects of the invention, a level of a histone or a fragment thereof can be determined in the sample that is not assembled in a macromolecular complex, such as a nucleosome, octamer or a neutrophil extracellular trap (NET). Such histone(s) are herein referred to as "free histone(s)". Accordingly, the level of the at least one histone may particularly be a level of at least one free histone.

The level of such free histones can be determined by the detection of amino acid sequences or structural epitopes of histones that are not accessible in an assembled stoichiometric macromolecular complex, like a mono-nucleosome or an octamer. In such structures, particular regions of the histones are covered and are thus sterically inaccessible as shown for the neutrophil extracellular traps ("NETs"), (Brinkmann V., et al. Science 303(5663): p. 1532-5, 2004). In addition, in the octamer or nucleosome, regions of histones also participate in intramolecular interactions, such as between the individual histones. Accordingly, the region/peptide/epitope of the histone that is determined in the context of the invention may determine whether the histone is a free histone or a histone that is assembled in a macromolecular complex. For example, in an immunoassay based method, the utilized antibodies may not detect histones, e.g. H4, when they are part of the octameric core of nucleosomes as the epitopes are structurally inaccessible. Herein below, regions/peptides/epitopes of the histone are exemplified that could be employed to determine a free histone. For example, regions/peptides/epitopes of the N-terminal or C-terminal tail of the histones can be employed to determine histones independent of whether they are assembled in the macromolecular complex or are free histones according to the present invention.

It is understood that the determination of histones may include post-translational modified histone proteins. Accordingly, the post-translational modifications can comprise deacetylation or acetylation, phosphorylation, methylation, ubiquitylation and citrullination of amino acids.

"Stoichiometric" in this context relates to intact complexes, e.g. a mononucleosome or an octamer. "Free histone proteins" can also comprise non-chromatin-bound histones. For example, "free histone proteins" may also comprise individual histone proteins or non-octameric histone complexes. Free histones may (e.g. transiently) be bound to individual histones, for instance, histones may form homo- or hetero-dimers. The free histones may also form homo- or hetero-tetramers. The homo- or heterotetramer may consist of four molecules of histones, e.g. H2A, H2B, H3 and/or H4. A typical heterotetramer is formed by two heterodimers, wherein each heterodimer consists of H3 and H4. It is also understood herein that a heterotetramer may be formed by H2A and H2B. It is also envisaged herein that a heterotetramer may be formed by one heterodimer consisting of H3 and H4, and one heterodimer consisting of H2A and H2B. Free histones are thus herein referred to as and can be monomeric, heterodimeric or tetrameric histone proteins, which are not assembled in a ("stoichiometric") macromolecular complex consisting of the histone octamer bound to nucleic acid, e.g. a nucleosome. In addition, free histones may also be bound to nucleic acids, and wherein said free histones are not assembled in a ("stoichiometric") macromolecular complex, e.g. an intact nucleosome. Preferably, the free histone(s) is/are essentially free of nucleic acids.

The fragment of the at least one histone can have any length, e.g. at least about 5, 10, 20, 30, 40, 50 or 100 amino acids, so long as the fragment allows the unambiguous determination of the level of the particular histone. The fragment of the at least one histone refers to an independent fragment of the histones, e.g. of the histones H2B, H4, H2A and H3. Various exemplary fragments of the histones are disclosed herein below that are suitable to determine the level of the histone in the sample of the subject. It is also herein understood that the level of the histones can be determined by determining a fragment spanning the N-terminal or C-terminal tail of the histones. In addition, the histone or the fragment thereof to be determined in the context of the present invention may also be modified, e.g. by post-translational modification. Exemplary post translational modifications can be acetylation, citrullination, deacetylation, methylation, demethylation, deimination, isomerization, phosphorylation and ubiquitination.

As used herein, the term "proadrenomedullin" or "proADM" refers to proadrenomedullin or a fragment thereof, particularly MR-proADM. It is understood that "determining the level of proADM" or the like refers to determining proADM or a fragment thereof. The fragment can have any length, e.g. at least about 5, 10, 20, 30, 40, 50 or 100 amino acids, so long as the fragment allows the unambiguous determination of the level of the proADM. In particular preferred aspects of the invention, "determining the level of proADM" refers to determining the level of midregional proadrenomedullin (MR-proADM). MR-proADM is a fragment of proADM. The peptide adrenomedullin (ADM) was discovered as a hypotensive peptide comprising 52 amino acids, which had been isolated from a human phenochromocytomeby (Kitamura et al., 1993). Adrenomedullin (ADM) is encoded as a precursor peptide comprising 185 amino acids ("preproadrenomedullin" or "pre-proADM"). An exemplary amino acid sequence of ADM is given in SEQ ID NO: 5. ADM comprises the positions 95-146 of the pre-proADM amino acid sequence and is a splice product thereof. "Proadrenomedullin" ("proADM") refers to pre-proADM without the signal sequence (amino acids 1 to 21), i.e. to amino acid residues 22 to 285 of pre-proADM. "Midregional proadrenomedullin" ("MR-proADM") refers to the amino acids 42-95 of pre-proADM. An exemplary amino acid sequence of MR-proADM is given in SEQ ID NO: 6. It is also envisaged herein that a peptide and fragment thereof of pre-proADM or MR-proADM can be used for the herein described methods. For example, the peptide or the fragment thereof can comprise the amino acids 22-41 of pre-proADM (PAMP peptide) or amino acids 95-146 of pre-proADM (mature adrenomedullin). A C-terminal fragment of proADM (amino acids 153 to 185 of preproADM) is called adrenotensin. Fragments of the proADM peptides or fragments of the MR-proADM can comprise, for example, at least about 5, 10, 20, 30 or more amino acids. Accordingly, the fragment of proADM may, for example, be selected from the group consisting of MR-proADM, PAMP, adrenotensin and mature adrenomedullin, preferably herein the fragment is MR-proADM.

It is also envisaged herein that polypeptides can be determined, which have a sequence identity to proADM or to the at least one histone. For example, polypeptides can be determined in the methods and kits of the invention that have at least 75%, 80%, 85%, 90%, 91%, 92%, 93%, 94%, 95%, 96%, 97%, 98% or 99% sequence identity to SEQ ID NO: 5 or 6, or respectively to SEQ ID NO: 1, SEQ ID NO: 2, SEQ ID NO: 3, or SEQ ID NO: 4, wherein the higher values of sequence identity are preferred. In accordance with the present invention, the terms "sequence identity", "homology" or "percent homology" or "identical" or "percent identity" or "percentage identity" in the context of two or more amino acid sequences refers to two or more sequences or subsequences that are the same, or that have a specified percentage of amino acids that are the same, when compared and aligned for maximum correspondence over the window of comparison (preferably over the full length), or over a designated region as measured using a sequence comparison algorithm as known in the art, or by manual alignment and visual inspection. Sequences having, for example, 70% to 90% or greater (preferably 95% or greater) sequence identity may be considered to be substantially identical. Such a definition also applies to the complement of a test sequence. Preferably, the described identity exists over a region that is at least about 10 to about 15 amino acids in length, more preferably, over a region that is at least about 20 to about 35 amino acids in length, most preferably, over the full length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

As used herein, the "level" of the marker refers to the quantity of the molecular entity of the marker in the sample. In other words, the concentration of the marker is determined in the sample. For example, the concentration of proADM or a fragment thereof, preferably MR-proADM, and/or the concentration of the histone(s) H2B, H4, H3 and/or H2A or (a) fragment(s) thereof is determined in the sample of the subject.

As used herein, the term "level of at least one histone" refers to the quantity of the molecular entity of the at least histone, e.g. the quantity of H2B, H4, H2A and/or H3, or a fragment thereof in a sample that is obtained from the subject. In other words, the concentration of the at least one histone protein or the fragment thereof is determined in the sample.

As used herein, the term "level of the marker proadrenomedullin (proADM)" or the "level of the marker proadrenomedullin (proADM) or a fragment thereof" refers to the quantity of the molecular entity of the marker proadrenomedullin or fragments thereof in a sample that is obtained from a subject. In other words, the concentration of the marker is determined in the sample. Hence, the term "level of the marker midregional proadrenomedullin (MR-proADM)" refers to the quantity of the molecular entity of the marker midregional proadrenomedullin (MR-proADM) in the sample that is obtained from a subject. As described above, it is also envisaged herein that a fragment of proadrenomedullin (proADM), preferably MR-proADM, can be detected and quantified. Also, fragments of MR-proADM can be detected and quantified. Suitable methods to determine the level of proADM or a fragment thereof (preferably MR-proADM) or to determine the level of the at least one histone or a fragment thereof are described herein below.

As used herein, the "adverse event" means a health condition/status of the subject that is or will be life threatening. Therefore, the adverse event refers to a critical deterioration of the health condition/status of the subject in comparison to an earlier health condition of the same subject, e.g. that is diagnosed and confirmed e.g. about 28 days, 14 days, 7 days, 3 days, 1 day, 12 hours, 5 hours, 1 hour or less before the deterioration; or in comparison to the health condition of subjects suffering from (a) similar disease(s) or medical condition(s), i.e. the progression of the disease(s) or medical disorder(s) is or becomes life threatening in the subject tested. The adverse event also can refer to a critical deterioration of the health condition/status of the subject in comparison to the health condition of healthy subjects. It is herein understood that a critical deterioration of the health condition/status, a life threatening condition/status of the subject or life threatening progression can mean that the subject is at risk to die, i.e. the fatal outcome of the subject is likely. A critical deterioration, critical health condition/status, or life threatening health condition/status can also be assessed/diagnosed by clinical scores, e.g. the SOFA score. For example, a SOFA score above 14 indicates a very severe health status indicating a critical health status of the subject. A SOFA score between 0 and 6 indicates a less severe health status and a SOFA score of 7 to 14 indicates a severe health status. For example, the health condition of the subject may critically deteriorate due to organ dysfunction, multiple organ dysfunctions, (a) disease(s) or medical disorder(s), such as an infection. Accordingly, the term "adverse event" may refer to an organ dysfunction, multiple organ dysfunctions, a disease or medical condition, such as an infection, that is or will be life threatening. For example, organ dysfunction or multiple organ dysfunction can lead to such a critical deterioration and thus the term "adverse event" may also refer to organ dysfunction or multiple organ dysfunctions, particularly organ failure or multiple organ failure. For example, a disease or medical disorder can lead to such a critical deterioration and thus the term "adverse event" may also refer to (a) disease(s) or medical disorder(s), wherein said disease(s) or medical disorder(s) could mean disease(s) or medical disorder(s) that are life threatening. The subject can also suffer from (a) disease(s)

and/or medical disorder(s) and the adverse event in such a scenario is the condition when the progression of the disease(s) or medical disorder(s) become(s) life threatening, i.e. the adverse event may also refer to a life threatening progression of the disease or disorder. A disease or disorder can be selected from the group consisting of respiratory disease, urinary tract infection, an inflammatory response related to infective and non-infective etiologies, systemic inflammatory response syndrome (SIRS), sepsis, severe sepsis, septic shock, organ failure(s), cardiovascular disease, hematologic disease, disseminated coagulation, diabetes mellitus, malignancy, liver disease, renal disease, immunodepression, viral infection, fungal infection, bacterial infection, gram-negative bacterial infection, gram-positive bacterial infection, abdominal infection and immunosuppression. The disease can also be (an) infection(s). In particular aspects, the subject suffers from a viral infection, fungal infection, bacterial infection, gram-negative bacterial infection, and/or gram-positive bacterial infection. The respiratory disease may also refer to a respiratory infection (such as Community Acquired Pneumonia (CAP) or lower respiratory tract infections (LRTI)). In a very particular aspect, the subject suffers from a fungal infection.

As used herein, the term "immunosuppressed subject" refers to a subject with a suppressed immune system compared to at least one healthy subject. Such an immunosuppressed may suffer from human immunodeficiency virus (HIV), or may be a subject undergoing radiotherapy, and/or receiving immunosuppressive drugs.

Preferably herein, the subjects suffer from severe sepsis or septic shock, preferably based on the SEPSIS-2 definition by the American College of Chest Physicians/Society of Critical Care Medicine Consensus Conference.

In particular aspects of the invention, the adverse event is mortality. In other words, the adverse event is the death of the subject in particular aspects of the invention. Accordingly, the term "adverse event" particularly means "mortality", or "death". As used herein, "mortality" means that the subject dies, i.e. the fatal outcome. Accordingly, the methods and kits of the invention determine/predict whether the subject will die and/or whether the subject is at risk to die.

As used herein, the general term "organ dysfunction" can also mean that more than one organ has a dysfunction, i.e. it can also relate to organ dysfunctions unless stated otherwise. The term "organ dysfunction" or "organ dysfunctions" relates to a condition in the subject where an organ or more than one organ do(es) not perform its/their normal function compared to an unaffected organ, such for example the organ(s) of at least one healthy subject. For example, the organ(s) can have a reduced activity or the organ(s) can be abnormally active in the subject with the organ dysfunction in comparison to (an) organ(s) of at least one healthy subject. Preferably, the organ(s) with the organ dysfunction(s) can have a reduction or an increase of activity of at least about 10%, 20%, 30%, 50%, 70%, 90%, 100% or 200% compared to unaffected organ(s), e.g. of at least one healthy subject. In particular, organ dysfunction(s) can result in organ failure(s). Accordingly, "organ dysfunction(s)" can preferably also refer to organ failure(s). "Organ failure(s)" refers to (an) organ dysfunction(s) to such a degree that normal homeostasis cannot be maintained, e.g. without external clinical intervention. "Organ failure(s)" may also refer to (an) organ dysfunction(s) to such a degree that normal homeostasis of the organ(s) cannot be maintained, e.g. without external clinical intervention. "Organ failure(s)" may also refer to (an) organ dysfunction(s) to such a degree that normal homeostasis of the subject cannot be maintained, e.g. without external clinical intervention. In particular aspects of the invention, the organ dysfunction is an organ failure or at least one organ failure. The general term "organ failure" can also mean that more than one organ has a failure, i.e. it can also relate to organ failures unless stated otherwise. It is herein understood that organ dysfunctions can also be referred to as multiple organ dysfunction. It is herein understood that organ failures can also be referred to as multiple organ failure. Exemplary organ dysfunctions or organ failures are circulatory shock, hematologic failure, liver failure, neurologic failure, renal failure, respiratory failure and metabolic acidosis. Accordingly, in the context of the invention, the organ dysfunction or the at least one dysfunction can preferably be selected from the group consisting of circulatory shock, hematologic failure, liver failure, neurologic failure, renal failure, respiratory failure and metabolic acidosis. It is herein understood that the subject can also have more than one organ dysfunctions or failures that are e.g. a combination of two, three, four organ dysfunctions selected from the group consisting of circulatory shock, hematologic failure, liver failure, neurologic failure, renal failure, respiratory failure and metabolic acidosis.

In particular aspects of the invention, the level of at least one histone and/or the level of proADM, particularly MR-proADM, is/are indicative of said adverse event occurring within about 28 days. As used herein, the term "the adverse event occurring within" means that the subject will likely, will or is experience(ing)/have(ing)/suffer(ing) from the adverse event within that particular time period.

As used herein, the term "adverse event does not occur" means that the event does not happen, e.g. within about 28 days. For example, the death of subject does not occur within this time range. Accordingly, this indicates that the subject survives, e.g. within about 28 days.

The level of at least one histone and/or the level of proADM, particularly MR-proADM, is/are also indicative of said adverse event occurring within about 28 days, about 25 days, about 20 days, about 15 days, about 14 days, about 13 days, about 12 days, about 11 days, about 10 days, about 9 days, about 8 days, about 7 days, about 6 days, about 5 days, about 4 days, about 3 days, about 2 days or about 1 day. The level of at least one histone and/or the level of proADM, particularly MR-proADM, may also be indicative of said adverse event occurring within 14 days. Particularly, the level of at least one histone and/or the level of proADM, particularly MR-proADM, may also be indicative of said adverse event occurring within 7 days. Particularly, the level of at least one histone and/or the level of proADM, particularly MR-proADM, may also be indicative of said adverse event occurring within 3 days.

In particular preferred aspects of the invention, the level of at least one histone and/or the level of proADM, particularly MR-proADM, is/are indicative of mortality of the subject occurring within about 28 days. The level of at least one histone and/or the level of proADM, particularly MR-proADM, may also be indicative of mortality occurring within about 28 days, about 25 days, about 20 days, about 15 days, about 14 days, about 13 days, about 12 days, about 11 days, about 10 days, about 9 days, about 8 days, about 7 days, about 6 days, about 5 days, about 4 days, about 3 days, about 2 days or about 1 day. The level of at least one histone and/or the level of proADM, particularly MR-proADM, may also be indicative of mortality occurring within 14 days. Particularly, the level of at least one histone and/or the level of proADM, particularly MR-proADM, may also be indicative of mortality occurring within 7 days. Particularly, the level of at least one histone and/or the level of proADM, particularly MR-proADM, may also be indicative of mortality occurring within 3 days.

In preferred aspects of the invention, said level of MR-proADM of said subject is indicative of the adverse event, particularly mortality, of said subject occurring within about 28 days or occurring within about 7 days.

In particular aspects of the invention, the level of at least one histone is indicative of the adverse event, particularly mortality, occurring within about 7 or, preferably within about 3 days. Particularly, the level of H2B is indicative of the adverse even occurring within about 7 or preferably within about 3 days.

In particular aspects of the invention, the level of at least one histone is indicative of the adverse event, particularly mortality, occurring within about 7 or, preferably within about 3 days. Particularly, the level of H4 is indicative of the adverse even occurring within about 7 or preferably within about 3 days.

In particular aspects of the invention, the level of at least one histone and the level proADM are indicative of the adverse event, particularly mortality, of said subject occurring within 28 days.

The term "indicative of said adverse event" means that the subject has or will likely experience/have/suffer from said adverse event, e.g. mortality. Therefore, the level of the at least one histone and/or the level of proADM of the subject indicate(s) the adverse event, e.g. mortality of the subject.

The method of the invention also relates to a method, wherein a level of at least one histone is determined in a sample of a subject, wherein said level of at least one histone is compared to a reference level of at least one histone and wherein said level of at least one histone is indicative of said adverse event.

Preferably, the invention also relates to a method, wherein a level of proadrenomedullin (proADM), particularly MR-proADM, is determined in a sample of a subject, wherein said level of proADM, particularly MR-proADM, is compared to a reference level of proADM and wherein said level of proADM, particularly MR-proADM, is indicative of said adverse event.

The method also relates to a method, wherein a level of at least one histone is determined and wherein a level of proadrenomedullin (proADM), particularly MR-proADM, is determined in a sample of a subject, wherein said level of at least one histone is compared to a reference level of at least one histone, and wherein said level of proADM is compared to a reference level of proADM, and wherein said adverse event in said subject is identified based on the comparison step.

As used herein, the term "is compared to a reference level of at least one histone" or grammatical variants thereof means that the level of the at least one histone of the subject is compared to a reference level of the at least one histone. Thus, a level of the histone of the subject is compared to a corresponding reference level of the same histone. For example, the level of the histone H2B determined in the sample of the subject is compared to a reference level of histone H2B. This applies mutatis mutandis to the other histones. The reference level of at least one histone is particularly a level of histone H2B, a level of histone H4, a level of histone H2A and/or a level of histone H3.

As used herein, the term "is compared to a reference level of proADM" or grammatical variants thereof means that the level of the proADM of the subject is compared to a reference level of the proADM. If a level of (a) fragment(s) of the at least one histone and/or of the proADM is determined the reference level may also be a level of (the) corresponding fragment(s).

As used herein, the "reference level" may reflect a normal level of the corresponding marker that is indicative of no adverse event in preferred aspects of the invention. Accordingly, such a reference level reflects a normal level of the corresponding marker that does not indicate a life threatening condition or particularly death/mortality of the subject. Accordingly, the reference level may be a level of at least one histone and/or a level of proADM of at least one reference subject, and wherein the reference subject(s) has/have no adverse event within about 28 days, preferably within about 14 days, more preferably within about 7 days or particularly preferably within about 3 days.

The reference level may represent the level of the at least one histone and/or the level of proADM of a group of healthy subjects (e.g. a cohort). Accordingly, the reference level is preferably a level of the at least one histone and/or a level of proADM, particularly MR-proADM of healthy subjects. A healthy subject is a subject with no diagnosed (and confirmed) disease and/or disorder. The healthy subjects may preferably have normally functioning organs, i.e. no organ dysfunction(s) or no organ failure(s), and/or no diagnosed disease(s) or medical disorder(s) such as those as described above. Accordingly, the reference level(s) can be a level of at least one histone and/or a level of proADM that is determined in samples of healthy subjects. The reference subjects or healthy subjects are herein preferably defined as a group of subjects or a group of healthy subjects, e.g. a cohort of subjects. The healthy reference subjects have no organ dysfunction or no organ failure. Accordingly, the reference level may be a level of the at least one histone and/or a level of proADM of subjects having no organ dysfunction or no organ failure. Accordingly, the reference level may be a level indicating no organ dysfunction or no organ failure.

In preferred embodiments, the reference level of proADM (preferably herein MR-proADM) is about 0.7 nmol/L to about 2.0 nmol/L. In more preferred embodiments, the reference level of proADM is about 0.8 nmol/L to about 1.9 nmol/L. In more preferred embodiments, the reference level of proADM is about 0.9 nmol/L to about 1.8 nmol/L. In more preferred embodiments, the reference level of proADM is about 0.88 nmol/L to about 1.79 nmol/L. In more preferred embodiments, the reference level of proADM is about 0.9 nmol/L or about 1.8 nmol/L. In most preferred embodiments, the reference level of proADM is about 0.88 nmol/L or about 1.79 nmol/L. The reference level applied depends on the desired specificity and sensitivity for the prediction, i.e. a lower threshold such as about 0.9 nmol/L (preferably 0.88 nmol/L) proADM (preferably MR-proADM) will reliably identify subjects not undergoing the adverse event (particularly mortality, i.e. specifically identify survivors within the 28 day time period).

In particular embodiments, a level of proADM of the subject that is (i) less than or equal to the reference level of proADM (e.g. about 0.9 nmol/L to 1.8 nmol/L) is indicative that the adverse event, particularly mortality, does not occur within 28 days; or (ii) higher than the reference level of proADM (e.g. about 0.9 nmol/L to 1.8 nmol/L) is indicative that the adverse event, particularly mortality, occurs or will occur within 28 days.

The sensitivity and specificity of the provided methods depend on more than just the analytical quality of the test. Sensitivity and specificity also depend on the definition of what constitutes an abnormal (e.g. mortality) or normal result. The distribution of levels of the at least one histone and/or of proADM, preferably the level of MR-proADM, for subjects with and without the adverse event may overlap. Under such conditions, a test does not absolutely distinguish normal from a dysfunctioning state with 100% accuracy. The skilled person is aware of the fact that the condition per se of a subject or at least one further maker and/or parameter of the subject can assist in the interpretation of the data and that this further information allows a more reliable prognosis in the areas of overlap. The condition per se may refer to the general health condition of subject. The general health condition of a subject can influence the decision which reference level to select. The appended examples document which reference levels were shown to be most suitable for the particular condition. With this knowledge the reference level can further be adapted. For example, the appropriate reference level may depend on the general health state of the subject. The general health state may be determined based on the SOFA score. For example, the reference level of proADM of about 1.8 nmol/L can be employed for less severely ill subjects, e.g. subjects with a SOFA score ≤6. The reference level of proADM of about 3.2 nmol/L can be employed for moderately severe ill subjects, e.g. subjects with a SOFA score of 7 to 12. The reference level of proADM of about 5.5 nmol/L can be employed for severely ill subjects, e.g. subjects with a SOFA score ≥13.

In preferred embodiments, the reference level of proADM may be about 1.8 nmol/L if the SOFA score of the subject is ≤6, the reference level of proADM may be about 3.2 nmol/L if the SOFA score of the subject is 7 to 12; or the reference level of proADM may be about 5.6 nmol/L if the SOFA score of the subject is ≥13. In most preferred aspects, the reference level of proADM may be about 1.8 nmol/L if the SOFA score of the subject is ≤6, or the reference level of proADM may be about 3.2 nmol/L if the SOFA score of the subject is 7 to 12.

Accordingly, the appropriate reference level may be selected by determining the level(s) of at least one further marker and/or parameter (e.g. sex, group and age). The levels of at least one further marker and/or parameter can also be compared to reference levels, wherein similar or identical values/levels of said at least one further marker and/or parameter of the subject compared to the corresponding levels of said at least one further marker and/or parameter of said reference levels indicate that the risk of the subject to experience/have/suffer from an adverse event is decreased, and/or wherein higher or lower levels/values of said at least one further marker and/or parameter compared to the corresponding levels of said at least one further marker and/or parameter of said reference levels indicate that the risk to experience/have/suffer from an adverse event is increased.

In addition, ROC tests as described below and in the appended examples may be employed to select the appropriate reference level that provides the most suitable prediction.

The appropriate reference level can also be influenced by the disease/disorder from which the subject suffers. For example, the appended examples show that subjects suffering from a fungal infection show the highest proADM levels. Accordingly, if a subject suffers from a fungal infection, the reference level of proADM may be 5.6 nmol/L.

Further, the reference level may also be a level of at least one histone and/or a level of proADM of at least one reference subject, wherein said reference subject(s) suffer(s) from a disease and/or medical disorder, and wherein the progression of the disease or disorder is not life threatening.

In other words, the reference level can also be a level of at least one histone and/or a level of proADM of at least one reference subject, wherein said reference subject(s) suffer(s) from a disease and/or medical disorder, and wherein the adverse event, particularly mortality, does not occur within 28 days, 7 days or 3 days.

Further, the reference level may also be a level of at least one histone and/or a level of proADM of at least one reference subject, wherein said reference subject(s) suffer(s) from a disease and/or medical disorder and an infection (such as sepsis or septic disorders), and wherein the adverse event, particularly mortality, does not occur within 28 days, 7 days or 3 days. In other words, the adverse event of the reference subject does not occur within 28 days, 7 days or 3 days.

Particularly, the reference subject suffers from the same disease or medical condition/disorder as the subject to be tested.

Further, the reference level may also be a level of at least one histone and/or a level of proADM of at least one reference subject, wherein said reference subject(s) suffer(s) from a disease and/or medical disorder and not from an infection, and wherein the adverse event, particularly mortality, does not occur within 28 days, 7 days or 3 days.

Further, the reference level may also be a level of at least one histone and/or a level of proADM of at least one reference subject, and wherein said reference subject(s) suffer(s) from a disease and/or medical disorder including SIRS, wherein said subject(s) do(es) not suffer from an infection, and wherein the adverse event, particularly mortality, does not occur within 28 days, 7 days or 3 days.

As used herein, the at least one reference subject refers to more than one reference subject. Particularly, the at least one reference subject is a group or a cohort of reference subjects. As described herein below, means and methods are described to determine the levels of the markers e.g. in reference.

The reference level as used herein is typically a predetermined level, i.e. it has been determined in advance as a reference for later use at the point-of-care, e.g. ICU or ED.

In preferred aspects of the invention, the adverse event is mortality. In these aspects, the reference level may also be level of at least one histone and/or a level of proADM of at least one reference subject, wherein the reference subject(s) do(es) not die within about 28 days, within about 14 days, within about 7 days or within about 3 days. Further, in these aspects, the reference level can also be a level of at least one histone and/or a level of proADM of at least one reference subject, wherein said reference subject(s) suffer(s) from a disease and/or medical disorder, and wherein the reference subject(s) do(es) not die within about 28 days, within about 14 days, within about 7 days or within about 3 days. Further, in these aspects, the reference level can also be a level of at least one histone and/or a level of proADM of at least one reference subject, wherein said reference subject(s) suffer(s) from a disease and/or medical disorder and an infection, and wherein the reference subject(s) do(es) not die within about 28 days, within about 14 days, within about 7 days or within about 3 days. Further, in these aspects, the reference level can also be a level of at least one histone and/or a level of proADM of at least one reference subject, wherein said reference subject(s) suffer(s) from a disease and/or medical disorder and not from an infection, and wherein the reference subject(s) do(es) not die within about 28 days, within about 14 days, within about 7 days or within about 3 days. Further, in these aspects, the reference level can also be a level of at least one histone and/or a level of proADM of at least one reference subject, and wherein said reference subject(s) suffer(s) from a disease and/or medical disorder including SIRS, wherein said subject(s) do(es) not suffer from an infection, and wherein the reference subject(s) do(es) not die within about 28 days, within about 14 days, within about 7 days or within about 3 days.

As documented herein, an increased level of at least one histone (or an increase in the level of at least one histone) and/or an increased level of proADM (or an increase in the level of proADM), particularly MR-proADM, as compared to the reference level is indicative of an adverse event, particularly mortality. In particular, the adverse event occurs within 28 days, 7 days or 3 days as described above. Accordingly, said level of the at least one histone and/or said level of proADM indicating said adverse event may be an increased level as compared to a reference level. Accordingly, the method of the invention includes a method that comprises determining a level of at least one histone in a sample of said subject, and wherein an increased level of said at least one histone of said subject as compared to a reference level of at least one histone is indicative of said adverse event, particularly mortality, of said subject.

Further, the invention includes a method that comprises determining a level of proADM, particularly MR-proADM, in a sample of said subject, and wherein an increased level of said proADM, particularly MR-proADM, of said subject as compared to a reference level of said proADM, particularly MR-proADM, is indicative of said adverse event, particularly mortality of said subject.

Further, the invention includes a method that comprises determining a level of proADM, particularly MR-proADM, in a sample of said subject, and wherein an increased level of proADM, particularly MR-proADM, as compared to the reference level of proADM, particularly MR-proADM, is indicative of said adverse event of said subject, wherein preferably said adverse event occurs within about 28 days; or wherein a decreased level or an equivalent level of proADM, particularly MR-proADM, as compared to the reference level of proADM, particularly MR-proADM, is indicative that said adverse event of said subject does not occur, preferably within about 28 days.

Further, the invention includes a method that comprises determining a level of at least one histone in a sample of said subject and determining a level of proADM, particularly MR-proADM, in a sample of said subject, and wherein an increased level of said at least one histone of said subject and an increased level of said proADM, particularly MR-proADM, of said subject as compared to a reference level of at least one histone and a reference level of said proADM, particularly MR-proADM are indicative of said adverse event, particularly mortality, of said subject.

The invention also relates to a method comprising
(i) determining a level of at least one histone in a sample of said subject, wherein said level of at least one histone is compared to a reference level of at least one histone,
and wherein an increased level of said at least one histone of said subject as compared to said reference level of at least one histone is indicative of said adverse event in said subject; and/or
(ii) determining a level of proadrenomedullin (proADM) in a sample of said subject, wherein said level of proADM is compared to a reference level of proADM and wherein an increased level of said proADM of said subject as compared to said reference level of proADM is indicative of said adverse event in said subject.

In other words, the invention also relates to a method comprising
(i) determining a level of at least one histone in a sample of a subject, wherein said level of at least one histone is compared to a reference level of at least one histone, and wherein an increase in the level of at least one histone as compared to the reference level of at least one histone is indicative of said adverse event of said subject; and/or
(ii) determining a level of proadrenomedullin (proADM) in a sample of said subject, wherein said level of proADM is compared to a reference level of proADM, and wherein an increase in the level of proADM as compared to the reference level of proADM is indicative of said adverse event of said subject.

The invention may also relate to a method comprising
(i) determining a level of at least one histone in a sample of said subject, wherein said level of at least one histone is compared to a reference level of at least one histone of the same subject obtained from prior analysis, and wherein an increase in the level of at least one histone as compared to said reference level of at least one histone is indicative of said adverse event in said subject; and/or
(ii) determining a level of proadrenomedullin (proADM) in a sample of said subject, wherein said level of proADM is compared to a reference level of proADM of the same subject obtained from prior analysis,
and wherein an increase in the level of proADM as compared to said reference level of proADM is indicative of said adverse event in said subject.

As used herein, "obtained from prior analysis" refers to a determination of the marker level in the sample of the same subject at a pervious time, e.g. 28 days, 7 days, 6 days, 5 days, 4 days, 3 days, 2 days or 1 day prior to the next analysis, and wherein in such aspects said previously determined level of the marker is considered as the reference level.

As used herein, the term "increase in the level of (the) marker" means that the level of the marker is increased, i.e. it refers to an increased level of the marker. Accordingly, the term "increase in the level of (the) marker" is used interchangeably herein with the term "increased level of (the) marker". An increased level of the marker or an increase in the level of the marker of the subject means that the level of the marker is at least about 15%, preferably at least about 20%, more preferably at least about 25%, or even more preferably at least about 30% higher than the reference level of the marker.

In the context of the invention, the term "increase in the level of at least one histone as compared to the reference level" or the like is used interchangeably herein with the term "increased level of the at least one histone of said subject as compared to said reference level" or the term "increased level of the at least one histone as compared to said reference level" or the like. Such terms mean that the level of the at least one histone, e.g. the level of H2B, the level of H4, the level of H2A and/or the level of H3, of the subject is at least about 15%, preferably at least about 20%, more preferably at least about 25%, more preferably at least about 30%, more preferably at least about 40%, more preferably at least about 50%, more preferably at least about 60%, more preferably at least about 70%, more preferably at least about 80%, more preferably at least about 90%, most preferably at least about 100% higher than the reference level of the at least one histone. In other words, in most preferred aspects, the increased level of said at least one histone (or the increase in the level) may be about twice as high as said reference level of at least one histone. An increase of the level of about twice further increases the risk of the adverse event, e.g. mortality. For example, a hazard ratio of 1.45 of H4 as documented in table 1 means that the risk of an adverse event is further increased by 45%. Therefore, such values are also an indication of a strong correlation and optimal markers for the diagnosis.

As used herein, the term "increase in the level of proADM as compared to the reference level" or the like is used interchangeably herein with the term "increased level of the proADM of said subject as compared to said reference level" or the term "increased level of the proADM as compared to said reference level" or the like. Such terms mean that the level of proADM, particularly the level of MR-proADM, of the subject is at least about 10%, preferably at least about 15%, more preferably at least about 20% more preferably at least about 25%, or even more preferably at least about 30%, more preferably at least about 40%, more preferably at least about 50%, more preferably at least about 60%, more preferably at least about 70%, more preferably at least about 80%, more preferably at least about 90%, most preferably at least about 100% higher than the reference level of proADM, particularly MR-proADM. In other words, in most preferred aspects, the increased level of said proADM may be about twice as high as said reference level of proADM.

As used herein, the term "decrease in the level of proADM as compared to the reference level" or the like is used interchangeably herein with the term "decreased level of the proADM of said subject as compared to said reference level" or the term "decreased level of the proADM as compared to said reference level" or the like. Such terms mean that the level of proADM, particularly the level of MR-proADM, of the subject is at least about 10%, preferably at least about 15%, more preferably at least about 20%, more preferably at least about 25%, or even more preferably at least about 30%, more preferably at least about 40%, more preferably at least about 50%, more preferably at least about 60%, more preferably at least about 70%, more preferably at least about 80%, more preferably at least about 90%, most preferably at least about 100% lower than the reference level of proADM, particularly MR-proADM. In other words, in most preferred aspects, the decreased level of said proADM may be about twice as low as said reference level of proADM.

The term "equal" also includes level that the level can be similar than the reference level. Accordingly, the term "equal" refers to a level of proADM of the subject that is +/−10%, preferably, +/−5%, more preferably +/−2% or most preferably the same or identical compared to the reference level of proADM.

As used herein, the term "decrease in the level or an equal level of proADM as compared to the reference level" mean that the level of proADM, particularly the level of MR-proADM, of the subject is +/−10%, +/−5%, +/−2% or the same or identical compared to the reference level or is at least about 10%, preferably at least about 20%, more preferably at least about 25%, or even more preferably at least about 30%, more preferably at least about 40%, more preferably at least about 50%, more preferably at least about 60%, more preferably at least about 70%, more preferably at least about 80%, more preferably at least about 90%, most preferably at least about 100% lower than the reference level of proADM, particularly MR-proADM.

It is herein understood that the reference levels and the determined marker levels (i.e. the levels that are determined for the individual subject at the point-of-care, e.g. ICU or ED) can vary depending on the assay/method by which the levels are determined. For example, the reference level and the determined marker level determined by mass spectrometry based methods can be different from respective levels determined by immunoassays. The appended examples demonstrate that the levels of the markers can be determined by several methods, e.g. immunoassays and mass spectrometry based methods. The reference levels can be optimized by statistical methods as exemplified in the appended examples, such as Cox regression analysis. Hazard ratios may also be calculated. For example and as exemplified in the appended examples, Hazard ratios higher than 0 (HR>0) indicate a worse prognosis, i.e. that the adverse event likely occurs, and Hazard rations smaller than 0 indicating a good prognosis, i.e. that the adverse event does likely not occur. Accordingly, the skilled person is aware how to determine reference levels. For example, the levels (including reference levels) can be determined by an immunoassay, e.g. by determining the level of at least one histone and/or the level of proADM, e.g. MR-proADM, in samples of subjects (or reference subjects).

In certain aspects of the invention, the reference level of the at least one histone may be about 100 ng/ml, more preferably about 90 ng/ml, more preferably about 80 ng/ml, more preferably about 70 ng/ml, more preferably about 60 ng/ml, more preferably about 50 ng/ml, more preferably about 45 ng/ml, more preferably about 40 ng/ml, or most preferably about 35 ng/ml. In certain aspects of the invention, the reference level of the at least one histone may be about 10 ng/ml, more preferably about 15 ng/ml, more preferably about 20 ng/ml, more preferably about 25 ng/ml, more preferably about 30 ng/ml, or most preferably about 35 ng/ml.

In certain aspects of the invention, the reference level of the at least one histone may be about 10 ng/ml to about 100 ng/ml, about 10 ng/ml to about 90 ng/ml, more preferably about 10 ng/ml to about 60 ng/ml, more preferably about 10 ng/ml to about 40 ng/ml, more preferably about 15 ng/ml to about 40 ng/ml, or most preferably about 20 ng/ml to about 40 ng/ml.

In certain aspects of the invention, the reference level of proADM may be about 4 nmol/L, more preferably about 5 nmol/L, more preferably about 7 nmol/L, more preferably about 8 nmol/L, more preferably about 9 nmol/L or particular preferably about 6 nmol/L.

Moreover, the levels (including reference levels) can be determined by mass spectrometric based methods, such as methods determining the relative quantification or determining the absolute quantification of the protein or fragment thereof of interest.

Relative quantification "rSRM" may be achieved by:

1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.

2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g. to amount of protein analyzed in each sample.

3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.

4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

Accordingly, the skilled person is aware how to determine marker levels and in particular appropriate reference levels as is also exemplified in the appended examples.

The methods and kits of the present invention can also comprise determining at least one further marker and/or parameter in addition to the at least one histone and/or proADM.

As used herein, a parameter is a characteristic, feature, or measurable factor that can help in defining a particular system. A parameter is an important element for health- and physiology-related assessments, such as a disease/disorder/clinical condition risk, preferably an adverse event. Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation score (APACHE scores I-IV), the simplified acute physiology score (SAPS I-Ill score), sequential organ failure assessment score (SOFA score), the quick SOFA (qSOFA) score, simplified acute physiology score II (SAPSII score), mortality probability model (MPM multiple organ dysfunction score (MODS), therapeutic intervention scoring system (TISS), nine equivalents of nursing manpower use score (NEMS), World Federation of Neurosurgical Societies (WFNS) grading, and Glasgow Coma Scale (GCS), CURB-65 pneumonia severity score, Pneumonia Severity Index (PSI), age, gender, family history, ethnicity, body weight, body mass index (BMI), cystoscopy report, white blood cell count, CT scan, blood pressure, heart rate, antihypertensive treatment, liquid intake, wheezing, body temperature, presence of diabetes mellitus and current smoking habits.

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker is defined as a characteristic that can be objectively measured and evaluated as an indicator of normal biological processes, pathogenic processes, or pharmacologic responses to a therapeutic intervention. Biomarkers may be measured in a sample (as a blood, plasma, urine, or tissue test). The at least one further marker of said subject can be selected from the group consisting of procalcitonin, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24) other ILs, Presepsin (sCD14-ST), Lipopolysaccharide Binding Protein (LBP), Alpha-1-Antitrypsin, Matrix Metalloproteinase 2 (MMP2), Matrix Metalloproteinase 9 (MMP9), Matrix Metalloproteinase 7 (MMP9), Chromogranin A, S100A protein, S100B protein and Tumor Necrosis Factor α (TNFα) or a fragment thereof.

In particular aspects of the invention, the at least one further marker and/or parameter of said subject can be selected from the group consisting of a level of aldolase B in said sample, a level of copeptin in said sample, a level of proendothelin-1 in said sample, a level of lactate in said sample, a level of procalcitonin (PCT) in said sample, the sequential organ failure assessment score (SOFA score) of said subject, the simplified acute physiology score (SAPSII score), the Acute Physiology and Chronic Health Evaluation II (APACHE II) score of said subject and a level of the soluble fms-like tyrosine kinase-1 (sFlt-1) in said sample.

In certain aspects of the invention the at least one further marker and/or parameter of said subject can be selected from the group consisting of procalcitonin, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-6 (IL-6), Interleukin-1, Interleukin-24 (IL-24) other ILs, Presepsin (sCD14-ST), Lipopolysaccharide Binding Protein (LBP), Alpha-1-Antitrypsin, Matrix Metalloproteinase 2 (MMP2), Matrix Metalloproteinase 9 (MMP9), Matrix Metalloproteinase 7 (MMP7), Chromogranin A, S100A protein, S100B protein, Tumor Necrosis Factor α (TNFα), age, gender, family history, ethnicity, body weight, body mass index (BMI), cystoscopy report, white blood cell count, CT scan, blood pressure, heart rate, antihypertensive treatment, liquid intake, wheezing, body temperature, presence of diabetes mellitus, current smoking habits, Acute Physiology and Chronic Health Evaluation score (APACHE scores I-IV), the simplified acute physiology score (SAPS I-Ill score), sequential organ failure assessment score (SOFA score), mortality probability model (MPM multiple organ dysfunction score (MODS), therapeutic intervention scoring system (TISS), nine equivalents of nursing manpower use score (NEMS), World Federation of Neurosurgical Societies (WFNS) grading, and Glasgow Coma Scale (GCS).

As used herein, "Aldolase B" refers to fructose-bisphosphate aldolase B or liver-type aldolase that is one of three isoenzymes (A, B, and C) of the class I fructose 1,6-bisphosphate aldolase enzyme. The level of Aldolase B in the sample of the subject can be determined by mass spectrometry based methods.

"Copeptin" is also referred to as "CT-proAVP" or "C-terminal portion of vasopressin". Vasopressin is a powerful vasoconstrictor. The level of CT-proAVP can be measured in the plasma or serum of a subject by immunoassays as described below.

As used herein, "lactate" refers to the maximal lactate concentration measured in the blood. Normally, the lactate concentration is assessed daily or even more often. The lactate concentration in the blood can be determined by lactate oxidase spectrophotometric methods.

As used herein, "procalcitonin" or "PCT" relates to a peptide spanning amino acid residues 1-116, 2-116, 3-116 or fragments thereof. Thus the length of procalcitonin fragments is at least 12 amino acids, preferably more than 50 amino acids, more preferably more than 110 amino acids. PCT may comprise post-translational modifications such as glycosylation, liposidation or derivatisation. Procalcitonin is a precursor of calcitonin and katacalcin. Thus, under normal conditions the PCT levels in the circulation are very low (< about 0.05 ng/ml). The level of PCT in the sample of the subject can be determined by immunoassays as described below.

As used herein, the "sequential organ failure assessment score" or "SOFA score" is one score used to track a patient's status during the stay in an intensive care unit (ICU) or Emergency Department (ED). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU or ED predicts a mortality rate of at least 50% up to 95%. Scores less than 9 give predictive mortality at 33% while above 14 can be close to or above 95%. As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU or ED. The SAPS II score can be determined at any time, preferably, at day 2. The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) or Emergency Department (ED) and may be determined based on 12 different physiologic parameters.

As used herein, the "quick SOFA score" or "qSOFA score" is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die.

As used herein, "Soluble fms-like tyrosine kinase-1" or "sFlt-1" is a tyrosine kinase protein that disables proteins that cause blood vessel growth. Soluble Flt-1 (sFlt-1) is a splice variant of VEGF receptor 1 (Flt-1) which is produced by a variety of tissues. The level of sFLT1 in the sample of the subject can be determined by mass spectrometry based assays and immunoassays.

As used herein, the "CURB-65" score (Lim et al., 2003) relates to the following risk factors of the subject:
Confusion of new onset (defined as an abbreviated mental test score (AMTS) (Hodkinson, 1972) of 8 or less),
Blood Urea nitrogen greater than 7 mmol/l (19 mg/dL),
Respiratory rate of 30 breaths per minute or greater,
Blood pressure less than 90 mmHg systolic or diastolic blood pressure 60 mmHg or less,
Age 65 or older.
Each risk factor scores one point, for a maximum score of 5.

As used herein, the "Pneumonia Severity Index" (PSI) relates to a clinical prediction rule for calculating the probability of morbidity and mortality among patients with community acquired pneumonia (Fine et al., 1997).

The methods or the kits of the invention can comprise determining the level of at least one histone and/or the level of proADM and a level of a further marker and/or parameter as described above. In preferred aspects, said methods or the kits of the invention can comprise determining said level of proADM and said SOFA score. Further, said methods or the kits of the invention can comprise determining said level of proADM, said SOFA score and said level of lactate of said subject.

The methods and the employed kits of the present invention may also comprise determining at least one further parameter, such as the SAPS II score, SOFA score and/or APACHE II score.

For example, the method can comprise determining the level of at least one histone and/or the level of proADM in the sample of the subject and the SAPS II score of the subject. Preferably, the method comprises determining said level of at least one histone in said sample of said subject and said SAPSII score of said subject. The level of at least one histone and the SAPSII score can be indicative of the adverse event, particularly mortality, of said subject occurring within 28 days. Preferably, the method comprises determining the level of proADM in said sample of said subject and said SAPSII score of said subject. The level of proADM and the SAPSII score can be indicative of the adverse event, particularly mortality, of said subject occurring within 28 days or within 7 days.

Further, the method may comprise determining the level of at least one histone and/or the level of proADM in the sample of the subject and the SOFA score of the subject.

Further, the method can comprise determining the level of at least one histone and/or the level of proADM in the sample of the subject and the level of PCT in the sample of the subject. Further, the method can comprise determining the level of at least one histone and/or the level of proADM in the sample of the subject and the level of aldolase B in the sample of the subject.

As used herein, the "subject" (or "patient") may be a vertebrate. In the context of the present invention, the term "subject" includes both humans and animals, particularly mammals, and other organisms. Thus, the herein provided methods are applicable to both human and animal subjects. Accordingly, said subject may be an animal such as a mouse, rat, hamster, rabbit, guinea pig, ferret, cat, dog, chicken, sheep, bovine species, horse, camel, or primate. Preferably, the subject is a mammal. Most preferably, the subject is human.

The method provided herein can be used on any subject that is a healthy subject or a subject that suffers from any diseases(s) or disorder(s). In preferred aspects, the subject suffers from a disease, disorder or medical condition. The subject to be tested can be a critical ill patient, preferably wherein said subject is admitted to an intensive care unit. As used herein, critical ill means that the subject or patient is in a life threatening situation.

The subject or the reference subject(s) may suffer from a disease or medical condition/disorder and wherein said disease or medical condition/disorder may be selected from the group consisting of respiratory disease, urinary tract infection, an inflammatory response related to infective and non-infective etiologies, systemic inflammatory response syndrome (SIRS), sepsis, severe sepsis, septic shock, organ failure(s), cardiovascular disease, diabetes mellitus, malignancy(ies), liver disease, renal disease, immunodepression, viral infection, fungal infection, bacterial infection, gram-negative bacterial infection, gram-positive bacterial infection and immunosuppresion. Herein, the method of the invention based on the detection of the proADM level (particularly the MR-proADM level) is particularly useful for the prediction of the adverse event in subjects suffering from a fungal infection. It is also particularly useful for subjects suffering from an infection of the respiratory tract, particularly the lower respiratory tract.

The subject may also suffer from an infection that followed a bone and/or tissue defect, e.g. a fracture of the bone.

Further, the subject may also be elected for surgery. This means that the subject will undergo surgery. This surgery may be connected to the disease and/or disorder being the reason or a symptom for the admission to the hospital.

Particularly, the subject of suffers from respiratory disease, urinary tract infection, and/or malignancy(ies).

"Systematic inflammation" in the context of the invention preferably relates to a condition characterized by a release of pro-inflammatory cytokines and an activated innate immune system which can be caused by biological factors, chemical factors or by genetic factors. Severe "Systemic Inflammation" can lead to organ failure and death.

"SIRS" in the context of the invention is a systemic inflammatory response syndrome with no signs of infection. It includes, but is not limited to more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a $PaCO_2$ of less than 32 mm Hg; and (4) an alteration in the white blood cell count such as a count greater than $12,000/mm^3$, a count less than $4,000/mm^3$, or the presence of more than 10% immature neutrophiles (Bone et al., CHEST 101(6): 1644-55, 1992).

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 Apr.; 31(4): 1250-6). The term "sepsis" used herein includes, but is not limited to, sepsis, severe sepsis, septic shock. Severe sepsis in this context means sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992).

The term "sepsis" also includes severe sepsis or septic shock based on the SEPSIS-2 definition (Bone et al., 2009). The term "sepsis" also includes subjects falling within the SEPSIS-3 definition (Singer et al., 2016).

The term "sepsis" used herein relates to all possible stages in the development of sepsis.

As used herein, "infection" within the scope of the invention means a pathological process caused by the invasion of normally sterile tissue or fluid by pathogenic or potentially pathogenic microorganisms and relates to infection(s) by bacteria, viruses, fungi, and/or parasites. Accordingly, the infection can be a bacterial infection, viral infection, and/or fungal infection. The infection can be a local or systemic infection. Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection.

Particularly, the subject suffers from sepsis. Further, the subject may preferably suffer from a respiratory disease, preferably an infection of the lower respiratory tract. As used herein respiratory disease comprises pathological conditions affecting the organs and tissues that make gas exchange possible in higher organisms, and also includes conditions of the upper respiratory tract, trachea, bronchi, bronchioles, alveoli, pleura and pleural cavity, and the nerves and muscles of breathing.

Particularly, in the methods and kits of the invention, the level of at least one histone in said sample of said subject suffering from said respiratory disease is indicative of the adverse event, particularly mortality occurring within 7 days.

Particularly, in the methods and kits of the invention, the subject suffers from a urinary tract infection and wherein said level of at least one histone in said sample of said subject suffering from said urinary tract infection is indicative of the adverse event, particularly, mortality occurring within 28 days.

Particularly, in the methods and kits of the invention, the subject suffers from a malignancy and wherein said level of at least one histone in said sample of said subject suffering from said malignancy is indicative of the adverse event, particularly mortality, occurring within 7 days.

As used herein, the term "sample" is a biological sample that is obtained from the subject. "Sample" as used herein may, e.g., refer to a sample of bodily fluid or tissue obtained for the purpose of diagnosis, prognosis, or evaluation of a subject of interest, such as a patient. Preferably herein, the sample is a sample of a bodily fluid, such as blood, serum, plasma, cerebrospinal fluid, urine, saliva, sputum, and pleural effusions. Particularly, the sample is blood, blood plasma, blood serum, or urine. The samples could be processed (pre-treated), such as by fractionation or purification procedures, for example, separation of whole blood into serum or plasma components. Such pre-treatments can also include, but are not limited to dilution, filtration, centrifugation, concentration, sedimentation, precipitation or dialysis. Pre-treatments may also include the addition of chemical or biochemical substances to the solution, such as acids, bases, buffers, salts, solvents, reactive dyes, detergents, emulsifiers, chelators. Preferably, the sample is a blood sample, more preferably a serum sample or a plasma sample.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

As described above, the level of at least one histone and/or of proADM is determined in the sample of the subject. The skilled person is aware of methods/assay that can be employed to determine the level of biomarkers in a sample.

As described above, the level of at least one histone is determined, particularly, the level(s) of the histones H2B, H4, H2A and/or H3 is/are determined. Particularly, the histone or the histone fragment can be determined. Such fragments are herein exemplified below.

Such a histone or fragment thereof may also represent a free histone. For example, the methods, kits and antibodies of the present invention may particularly detect peptides or epitopes of free histones. Such stretches of amino acids are also referred herein as central regions or parts of the histones. In the following, peptides or epitopes are described that may also be employed to detect free histones using the methods herein provided.

In particular, the at least one histone can be histone H4 and wherein at least a peptide of the sequence spanning amino acid residues 22 to 102 of histone H4 according to SEQ ID NO:1 is determined. Particularly, the least one histone is histone H4 and wherein at least a peptide of the sequence is determined selected from the group consisting of an amino acid sequence spanning residues 60 to 67 of SEQ ID NO: 1, residues 46 to 56 of SEQ ID NO:1, residues 67 to 78 of SEQ ID NO: 1, residues 22 to 30 of SEQ ID NO: 1, residues 67 to 78 of SEQ ID NO: 1, residues 92 to 102 of SEQ ID NO: 1, residues 22 to 34 of SEQ ID NO: 1, residues 46 to 102 of SEQ ID NO: 1, residues 46 to 55 of SEQ ID NO: 1, residues 80 to 91 of SEQ ID NO: 1, residues 24 to 35 of SEQ ID NO: 1, and residues 68 to 77 of SEQ ID NO: 1. For example, two peptides may be determined Particularly, the least one histone is histone H4 and wherein the peptides are determined of an amino acid sequence spanning residues 46 to 56 of SEQ ID NO:1 and residues 67 to 78 of SEQ ID NO: 1.

Further, the least one histone is histone H2A and wherein at least a peptide of the sequence spanning amino acid residues 20 to 118 of histone H2A according to SEQ ID NO: 2 is determined. In particular, the least one histone is histone H2A and wherein at least a peptide of the sequence is determined selected from the group consisting of an amino acid sequence spanning residues 21 to 53 of SEQ ID NO: 2, residues 21 to 29 of SEQ ID NO: 2, residues 30 to 53 of SEQ ID NO: 2, residues 120 to 129 of SEQ ID NO: 2, residues 21 to 29 of SEQ ID NO: 2, residues 82 to 88 of SEQ ID NO: 2, residues 89 to 95 of SEQ ID NO: 2, and residues 100 to 118 of SEQ ID NO: 2.

Further, the least one histone is histone is histone H3 and wherein at least a peptide of the sequence spanning amino acid residues 27 to 62 of histone H3 according to SEQ ID NO: 3 is determined. Further, the least one histone is histone H3 and wherein at least a peptide of the sequence spanning amino acid residues 27 to 37 of SEQ ID NO: 3 and/or spanning amino acid residues 52 to 62 of SEQ ID NO: 3 is determined.

Further, the least one histone is histone H2B and wherein at least a peptide of the sequence spanning amino acid residues 41 to 69 of histone H2B according to SEQ ID NO: 4 is determined.

Further, the least one histone is histone H2A and wherein at least a peptide or a fragment thereof is determined selected from the group consisting of SEQ ID NOs: 7, 8, 9 and 10 is determined.

Further, the least one histone is histone H4 and wherein at least a peptide or a fragment thereof selected from the group consisting of SEQ ID NOs: 11, 12, 13, 14, 15 and 16 is determined. It is herein understood that one, two three, four or more peptides can be determined.

The level of the markers, e.g. the at least one histone or the fragment thereof and/or the proADM or the fragment thereof, can be determined by any assay that reliably determines the concentration of the marker. Particularly, mass spectrometry (MS) and/or immunoassays can be employed as exemplified in the appended examples. As used herein, an immunoassay is a biochemical test that measures the presence or concentration of a macromolecule/polypeptide in a solution through the use of an antibody or antibody binding fragment or immunoglobulin.

Alternatively, instead of antibodies, other capture molecules or molecular scaffolds that specifically and/or selectively recognize histone sequences, histone epitopes, and structural conformations of histones may be encompassed by the scope of the present invention. Herein, the term "capture molecules" or "molecular scaffolds" comprises molecules which may be used to bind target molecules or molecules of interest, i.e. analytes (e.g. the histone(s) and/or proADM), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins), Affimers and the like.

As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to the at least one histone and/or that bind specifically to proADM are used. An antibody is considered to be specific, if its affinity towards the molecule of interest, e.g. the at least one histone and/or proADM, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of the at least one histone protein. Thus, the herein defined peptides can also be epitopes to which the antibodies specifically bind to. Further, an antibody or an antibody binding fragment is used in the methods and kits of the invention that binds specifically to proADM, particularly to MR-proADM. Exemplary immunoassays can be luminescence immunoassay (LIA), radio-immunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed.

In certain aspects of the invention, the method is a method for the diagnosis, prognosis, risk assessment, and/or risk stratification of an adverse event of a subject, wherein said method comprises
(i) obtaining a sample of the subject;
(ii) detecting a level of at least one histone and/or a level of proadrenomedullin (proADM) in the sample of said subject by contacting the sample with (an) antibody(ies) or (an) antigen-binding fragment(s) or derivative(s) thereof specific for a epitope of said at least one histone and/or of said proADM and detecting binding between the antibody (ies) or the antigen-binding fragment(s) or derivative(s) thereof and said at least one histone and/or said proADM; and
(iii) wherein said level of at least one histone and/or said level of proadrenomedullin (proADM) is/are indicative of is indicative of said adverse event of said subject.

In certain aspects of the invention, the method is an immunoassay comprising the steps of:
a) contacting the sample with
(i) a first antibody or an antigen-binding fragment or derivative thereof specific for a first epitope of a histone or of proADM, and
(ii) a second antibody or an antigen-binding fragment or derivative thereof specific for a second epitope of the histone or the proADM; and
b) detecting the binding of the first and second antibodies or antigen-binding fragments or derivates thereof to the histone or to proADM.

Preferably, one of the antibodies can be labeled and the other antibody can be bound to a solid phase or can be bound selectively to a solid phase. In a particularly preferred aspect of the assay, one of the antibodies is labeled while the other is either bound to a solid phase or can be bound selectively to a solid phase. The first antibody and the second antibody can be present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said at least one histone and/or to said proADM to be detected, a measurable signal which permits detection of the resulting sandwich complexes in the measuring solution is generated. The labelling system can comprise a rare earth cryptate or chelate in combination with a fluorescent or chemiluminescent dye, in particular of the cyanine type.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, e.g., the histone or the proADM or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of the histone or proADM or a fragment thereof, and/or the level of any further marker of the herein provided method is determined. In particular preferred aspects, the diagnostic device is KRYPTOR®.

Further, the immunoassay methods of the present invention may preferably utilize a first antibody and/or a second antibody or antigen-binding fragment(s) or derivative(s) thereof being specific for (an) epitope(s) of at least one histone and/or of proADM. Exemplary, peptides are described herein below and above that can be suitable for the determination of the level of proADM and/or of the at least one histone.

For example, the immunoassay methods of the present invention may preferably utilize a first antibody and/or a second antibody or antigen-binding fragment(s) or derivative(s) thereof being specific for (an) epitope(s) of histone H4, wherein the first epitope and/or second epitope are epitopes of histone H4 present in the sequence spanning amino acid residues 22 to 102 of SEQ ID NO:1.

Further, the immunoassay methods of the present invention may utilize a first antibody, antigen-binding fragment or derivative thereof that is specific for an epitope of histone H4 present in the sequence spanning amino acid residues 46 to 56 of SEQ ID NO:1, and a second antibody, antigen-binding fragment or derivative thereof that is specific for an epitope of histone H4 present in the sequence spanning amino acid residues 67 to 78 of SEQ ID NO: 1.

For example, the immunoassay methods of the present invention may preferably utilize a first antibody and/or a second antibody or antigen-binding fragment(s) or derivative(s) thereof being specific for (an) epitope(s) of histone H2B, wherein the first epitope and/or second epitope are epitopes of histone H2B present in the sequence spanning amino acid residues 41 to 69 of SEQ ID NO:4.

Further, the immunoassay methods of the present invention may preferably utilize a first antibody and/or a second antibody or antigen-binding fragment(s) or derivative(s) thereof being specific for (an) epitope(s) of histone H2A, wherein the first epitope and/or second epitope are epitopes of histone H2A present in the sequence spanning amino acid residues 20 to 118 of SEQ ID NO:2. Further, the immunoassay methods of the present invention may utilize a first antibody and/or a second antibody or antigen-binding fragment(s) or derivative(s) thereof being specific for (an) epitope(s) of histone H2A, wherein the first epitope and/or second epitope are epitopes of histone H2A present in the sequence spanning amino acid residues 21 to 53, 20 to 118 or 120 to 129 of SEQ ID NO:2.

Further, the immunoassay methods of the present invention may utilize a first antibody and/or a second antibody or antigen-binding fragment(s) or derivative(s) thereof being specific for (an) epitope(s) of histone H3, wherein the first epitope and/or second epitope are epitopes of histone H3 present in the sequence spanning amino acid residues 27 to 62 of SEQ ID NO:3.

More preferably, the immunoassay methods of the present invention may utilize a first antibody and/or a second antibody or antigen-binding fragment(s) or derivative(s) thereof being specific for (an) epitope(s) of histone H4, wherein the epitope(s) is/are selected from the group consisting of an amino acid sequence spanning residues 22 to 30 of SEQ ID NO:1, residues 46 to 56 of SEQ ID NO:1, residues 67 to 78 of SEQ ID NO:1, residues 92 to 102 of SEQ ID NO:1, residues 22 to 34 of SEQ ID NO: 1, and residues 46 to 102 of SEQ ID NO: 1.

Further, the immunoassay methods of the present invention may utilize a first antibody and/or a second antibody or antigen-binding fragment(s) or derivative(s) thereof being specific for (an) epitope(s) of histone H2A, wherein the epitope(s) is/are selected from the group consisting of an amino acid sequence spanning residues 21 to 53 of SEQ ID NO:2, residues 21 to 29 of SEQ ID NO:2, residues 30 to 53 of SEQ ID NO:2, and residues 120 to 129 of SEQ ID NO: 2.

Further, the immunoassay methods of the present invention may utilize a first antibody and/or a second antibody or antigen-binding fragment(s) or derivative(s) thereof being specific for (an) epitope(s) of histone H2B spanning residues 41 to 69 of SEQ ID NO: 4.

Further, the immunoassay methods of the present invention may utilize a first antibody and/or a second antibody or antigen-binding fragment(s) or derivative(s) thereof being specific for (an) epitope(s) of histone H3 spanning residues 27 to 37 of SEQ ID NO: 3 and/or spanning residues 52 to 62 of SEQ ID NO: 3.

Further, the immunoassay methods of the present invention may utilize a first antibody and/or the second antibody or the antigen-binding fragment or derivative thereof which are specific for an epitope of histone H2A present in the sequence spanning amino acid residues 21 to 53 and/or 120 to 129 of the histone H2A sequence represented by SEQ ID NO:2.

Further, the immunoassay methods of the present invention may utilize a first antibody, antigen-binding fragment or derivative thereof that is specific for an epitope of histone H4 present in the sequence spanning amino acid residues 22 to 102 of SEQ ID NO:1, and a second antibody, antigen-binding fragment or derivative thereof that is specific for an epitope of a free histone H2A, H2B, or preferably H3.

Further, the immunoassay methods of the present invention may utilize a first antibody, antigen-binding fragment or derivative thereof that is specific for an epitope of histone H2B present in the sequence spanning amino acid residues 41 to 69 of SEQ ID NO:4, and a second antibody, antigen-binding fragment or derivative thereof that is specific for an epitope of a free histone H2A, H4, or H3.

Further, the immunoassay methods of the present invention may utilize a first antibody, antigen-binding fragment or derivative thereof that is specific for an epitope of histone H2B present in the sequence spanning amino acid residues 20 to 118 of SEQ ID NO:2, and a second antibody, antigen-binding fragment or derivative thereof that is specific for an epitope of a free histone H2B, H4, or H3.

Further, the immunoassay methods of the present invention may utilize a first antibody, antigen-binding fragment or derivative thereof that is specific for an epitope of histone H2B present in the sequence spanning amino acid residues 27 to 62 of SEQ ID NO:3, and a second antibody, antigen-binding fragment or derivative thereof that is specific for an epitope of a free histone H2B, H4, or H2A.

Further, the immunoassay methods of the present invention may utilize a first antibody, antigen-binding fragment or derivative thereof that is specific for an epitope of histone H2A present in the sequence spanning amino acid residues 21 to 53, 120 to 129, or 20 to 118 of SEQ ID NO:2, and a second antibody, antigen-binding fragment or derivative thereof that is specific for an epitope of a free histone H3, H4 or preferably H2B.

The invention further relates to an antibody or an antigen-binding fragment or derivative thereof which is specific for an epitope of a histone protein or fragment thereof as detailed above. Exemplary antibodies that are successfully employed to detect histones or proADM, preferably MR-proADM are shown in the appended examples. The present invention thus relates to an antibody(ies), (an) antigen-binding fragment(s) or derivative(s) thereof that is/are specific for an epitope of histone H2B, H4, H2A, H3 and/or proADM, preferably MR-proADM. Exemplary epitopes or peptides to which the antibodies are specifically binding to are herein documented above and below.

The level of the marker, e.g. the at least one histone and/or proADM, can also be determined by a mass spectrometric (MS) based analysis as described in the appended examples. Such a method may comprise detecting the presence, amount or concentration of one or more modified or unmodified fragment peptides of e.g. proADM and/or the histone in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of at least one histone peptide. Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

As used herein, "diagnosis" in the context of the present invention relates to the recognition and (early) detection of the adverse event, particularly mortality, in a subject and may also comprise differential diagnosis. Also the assessment of the severity of the adverse event may be encompassed by the term "diagnosis". For example, the assessment of how critical the condition is and how likely the occurrence of the adverse event is. In addition, diagnosis means that the time can be predicted when the adverse event in the subject occurs, e.g. within about at least 28, 7 or 3 days.

"Prognosis" relates to the prediction of an outcome or a specific risk for a subject to experience/have/suffer from an adverse event, particularly mortality. This may also include an estimation of the chance of recovery or the chance of an adverse outcome for said subject.

The invention also relates to methods and kits for monitoring, therapy guidance and/or therapy control of subjects, the method comprises
(i) determining a level of at least one histone in a sample of said subject, and wherein said level of at least one histone is indicative of said adverse event of said subject; and/or
(ii) determining a level of proadrenomedullin (proADM) in a sample of said subject, and wherein said level of proADM is indicative of said adverse event of said subject.

The methods and kits of the invention may also be used for monitoring. "Monitoring" relates to keeping track of an already diagnosed disease or medical condition, e.g. to analyze the progression of the disease or medical condition or the influence of a particular treatment on the progression, and to predict the adverse outcome, e.g. a live threatening health condition or even mortality.

The term "therapy control" in the context of the present invention refers to the monitoring and/or adjustment of a therapeutic treatment of the subject. The adjustment of a therapeutic treatment may also include the decision whether the subject is treated further as done before or whether the treatment is adapted. For example, the adjustment of the therapeutic treatment may be whether the subject is kept on the ICU or ED or whether it is released.

In the present invention, the terms "risk assessment" and "risk stratification" relate to the grouping of subjects into different risk groups according to their further prognosis. Risk assessment also relates to stratification for applying preventive and/or therapeutic measures.

As used herein, the term "therapy guidance" refers to application of certain therapies or medical interventions based on the value of one or more biomarkers and/or clinical parameter and/or clinical scores.

The methods of the present invention may in part be computer-implemented. For example, the step of comparing the detected level of a marker, e.g. the proADM level and/or a histone level, with a reference level can be performed in a computer system. In the computer-system, the determined level of the marker(s) can be combined with other marker levels and/or parameters of the subject in order to calculate a score which is indicative for the diagnosis, prognosis, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. ICU or ED) or it can be at a remote location connected via a computer network (e.g. via the internet). Typically, the computer-system will store the values (e.g. marker level or parameters such as age, blood pressure, weight, sex, etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment or stratification will be displayed and/or printed for the user (typically a health professional such as a physician).

Hence, the present invention in a further aspect relates to a system for the diagnosis, prognosis, risk assessment, and/or risk stratification of an adverse event in the subject, comprising
(i) a sample analyzer for determining the level of proADM and/or a histone in the sample of a subject (and optionally further marker levels); and
(ii) a computer sub-system programmed to calculate the diagnosis, prognosis, risk assessment, and/or risk stratification of an adverse event in the subject, typically based on the comparison of the determined level(s) with (a) reference level(s).

The computer-sub-system may combine the detected marker level(s) with further level(s) and/or parameter(s) as described herein. The output of the device can be a score or directly the diagnosis, prognosis, risk assessment, and/or risk stratification of an adverse event in the subject.

In a related aspect the invention pertains to a computer program product embodied in a computer readable medium that, when executing on a computer, performs steps comprising determining the diagnosis, prognosis, risk assessment, and/or risk stratification of an adverse event in a subject based on the determined level of proADM and/or a histone in the sample of the subject. Typically this step is based on the comparison of the determined level(s) with (a) reference level(s) as described herein.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for the diagnosis, prognosis, risk assessment, and/or risk stratification, wherein said kit comprises
(i) detection reagents for determining said level of at least one histone in said sample of said subject, and
reference data including said reference level of at least one histone, and wherein an increased level of said at least one histone in said sample of said subject as compared to said reference level of at least one histone is indicative of an adverse event of said subject; and/or
(ii) detection reagents for determining said level of proADM in said sample of said subject, and
reference data including said reference level of proADM, and
wherein an increased level of said proADM in said sample of said subject as compared to said reference level of proADM is indicative of an adverse event of said subject.

Further, the invention preferably relates to a kit and its use for carrying out the method of the invention, wherein said kit comprises detection reagents for determining said level of proADM in said sample of said subject, and reference data including said reference level of proADM, and wherein an increase in the level of proADM in said sample of said subject as compared to said reference level of proADM is indicative of an adverse event of said subject.

Further, the invention preferably relates to a kit and its use for carrying out the method of the invention, wherein said kit comprises detection reagents for determining said level of proADM in said sample of said subject, and reference data including said reference level of proADM, and wherein a decrease in the level of proADM or a similar level of proADM in said sample of said subject as compared to said reference level of proADM indicates that an adverse event of said subject does not occur within about 28 days.

The invention also relates to a kit for and its use kits in the diagnosis, prognosis, risk assessment, and/or risk stratification of an adverse event of a subject,
(i) wherein the level of at least one histone is determined in the sample of the subject,
wherein the level of the at least one histone is compared to the reference level of at least one histone, and
wherein the adverse event of said subject is identified based on the comparison of the level of at least one histone determined in the sample and the reference level of at least one histone; and/or
(ii) wherein the level of proADM is determined in the sample of the subject,
wherein the level of proADM is compared to the reference level of proADM, and
wherein the adverse event of the subject is identified based on the comparison of the level of proADM determined in the sample and the reference level of proADM.

The invention also relates to the kit and its use for the diagnosis, prognosis, risk assessment,
and/or risk stratification of an adverse event of a subject,
(i) wherein the kit comprises detection reagents for determining a level of at least one histone in the sample of a subject, and
wherein the level of at least one histone is indicative of the adverse event of said subject s; and/or
(ii) wherein the kit comprises detection reagents for determining a level of proADM in the sample of a subject, and
wherein said level of said proADM is indicative of said adverse event of said subject.

As used herein, "reference data" comprise reference level(s) of at least one histone and/or of proADM, particularly MR-proADM. The levels of the at least one histone and/or of proADM in the sample of the subject can be compared to the reference levels comprised in the reference data of the kit. An increased level of the marker(s) determined is indicative of the adverse event, particularly mortality. A decreased level or an equal level of the marker(s) determined indicates that the adverse event does not occur, particularly mortality. The reference levels are herein described above. The reference data can also include a reference sample to which the level of the at least one histone and/or the level of proADM is compared to. The reference data can also include an instruction manual how to use the kits of the invention.

As used herein, the "detection reagent" or the like are reagents that are suitable to determine the herein described marker(s), e.g. the at least one histone and/or the proADM. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents, e.g. enzymes, chemicals, buffers, etc, that are used to prepare the sample for the MS analysis.

A mass spectrometer can also be considered as a detection reagent. Detection reagents according to the invention can also be calibration solution(s), e.g. that can be employed to determine and compare the level of the marker(s).

The given definitions and explanations also apply mutatis mutandis to the following items. The present invention also relates to the following items:

1. A method for the diagnosis, prognosis, risk assessment, and/or risk stratification of an adverse event of a subject, wherein said method comprises
   (i) determining a level of at least one histone in a sample of said subject, and wherein said level of at least one histone is indicative of said adverse event of said subject; and/or
   (ii) determining a level of proadrenomedullin (proADM) in a sample of said subject, and wherein said level of proADM is indicative of said adverse event of said subject.
2. The method of item 1, wherein said adverse event occurs within 28 days or wherein said adverse event does not occur within 28 days.
3. The method of item 1 or 2, wherein
   (i1) said level of at least one histone is compared to a reference level of at least one histone; and/or
   (ii1) said level of proADM is compared to a reference level of proADM; and
   (iii) wherein said adverse event of said subject is identified based on the comparison in step (i1) and/or (ii1), respectively.
4. The method of any one of items 1 to 3, wherein
   (i) an increase in the level of at least one histone as compared to the reference level of at least one histone is indicative of said adverse event of said subject; and/or
   (ii) an increase in the level of proADM as compared to the reference level of proADM is indicative of said adverse event of said subject wherein preferably said adverse event occurs within about 28 days, or
      a decrease in the level or an equal level of said proADM of said subject as compared to said reference level of said proADM is indicative that the adverse event does not occur, preferably within about 28 days.
5. The method of any one of items 1 to 4, wherein said adverse event is selected from the group consisting of mortality, organ dysfunction, multiple organ dysfunctions, and a disease or medical disorder, such as an infection.
6. The method of any one of items 1 to 5, wherein said adverse event is mortality.
7. The method of any one of items 3 to 6, wherein the reference level of proADM is about 0.9 nmol/L to about 1.8 nmol/L.
8. The method of any one of items 1 to 7, wherein
   (i) the increased level of said at least one histone is about twice as high as said reference level of at least one histone; and/or
   (ii) the increased level of said proADM is about twice as high as said reference level of proADM.
9. The method of any one of items 3 to 8, wherein said reference level of at least one histone and/or the reference level of proADM is/are a level of at least one histone and/or a level of proADM of at least one reference subject.
10. The method of any one of items 3 to 9, wherein the reference subject(s) is/are healthy subject(s) and/or subject(s) that has/have no adverse event.
11. The method of any one of items 3 to 10, wherein said reference level of at least one histone and/or the reference level of proADM is a level of at least one histone and/or of proADM that is/are obtained from prior analysis of said subject.
12. The method of any one of items 1 to 11, wherein said proADM is midregional proadrenomedullin (MR-proADM).
13. The method of any one of items 1 to 12, wherein said level of proADM of said subject is indicative of said adverse event, preferably mortality, of said subject occurring within 28 days.
14. The method of any one of items 1 to 13, wherein said level of proADM of said subject is indicative of said adverse event, preferably mortality, of said subject occurring within 7 days.
15. The method of any one of items 1 to 14, wherein said at least one histone is histone H2B, histone H2A, histone H3 and/or histone H4.
16. The method of any one of items 1 to 15, wherein said at least one histone is histone H2B.
17. The method of any one of items 1 to 16, wherein said level of the at least one histone of said subject is indicative of said adverse event, preferably mortality, of said subject occurring within 7 days or within 3 days.
18. The method of any one of items 1 to 17, wherein said method further comprises determining at least one marker and/or parameter of said subject selected from the group consisting of a level of lactate in said sample, a level of at least one histone, a level of aldolase B in said sample, a level of copeptin in said sample, a level of lactate in said sample, a level of procalcitonin (PCT) in said sample, the sequential organ failure assessment score (SOFA score) of said subject, the simplified acute physiology score (SAPSII score), the Acute Physiology and Chronic Health Evaluation II (APACHE II) score of said subject and a level of the soluble fms-like tyrosine kinase-1 (sFlt-1) in said sample.
19. The method of any one of items 1 to 18, wherein further the sequential organ failure assessment score (SOFA score) of said subject is determined.
20. The method of any one of items 3 to 19, wherein the reference level of proADM is about 1.8 nmol/L if the SOFA score of the subject is 6; the reference level of proADM is about 3.2 nmol/L if the SOFA score of the subject is 7 to 12; or the reference level of proADM is about 5.5 nmol/L if the SOFA score of the subject is 13.
21. The method of any one of items 1 to 20, wherein
   a decrease in the level or an equal level of proADM of said subject as compared to the reference level of proADM that is about 1.8 nmol/L and a SOFA score of ≤6 of said subject are indicative that said adverse event does not occur;
   a decrease in the level or an equal level of proADM of said subject as compared to the reference level of proADM that is about 3.2 nmol/L and a SOFA score of 7 to 12 of said subject are indicative that said adverse event does not occur; or
   a decrease in the level or an equal level of proADM of said subject as compared to the reference level of proADM that is about 5.6 nmol/L and a SOFA score of ≥13 of said subject are indicative that said adverse event does not occur; and
   wherein preferably said adverse event does not occur within about 28 days.

22. The method of any one of items 1 to 20, wherein
an increase in the level of proADM of said subject as compared to the reference level of proADM that is about 1.8 nmol/L and a SOFA score of ≤6 of said subject are indicative of said adverse event of said subject;
an increase in the level of proADM of said subject as compared to the reference level of proADM that is about 3.2 nmol/L and a SOFA score of 7 to 12 of said subject are indicative of said adverse event of said subject; or
an increase in the level of proADM of said subject as compared to the reference level of proADM that is about 5.6 nmol/L and a SOFA score of ≥13 of said subject are indicative of said adverse event of said subject,
wherein preferably said adverse event occurs within about 28 days.
23. The method of any one of items 19 to 23, wherein the SOFA score of said subject is increased based on the level of proADM of said subject, and wherein said modified SOFA score is indicative of said adverse event.
24. The method of item 23, wherein the SOFA score of the subject is increased by one if the subject has a proADM level that is higher than about 1.8 nmol/L.
25. The method of any one of items 1 to 24, wherein said method comprises determining said level of at least one histone and said level of proADM in said sample of said subject.
26. The method of item 25, wherein said level of at least one histone and said level proADM are indicative of said adverse event, preferably mortality, of said subject occurring within 28 days.
27. The method of any one of items 1 to 26, wherein said method comprises determining said level of at least one histone in said sample of said subject and said SAPSII score of said subject.
28. The method of item 27, wherein said level of at least one histone and said SAPSII score are indicative of said adverse event, preferably mortality, of said subject occurring within 28 days.
29. The method of any one of items 1 to 28, wherein said method comprises determining said level of proADM in said sample of said subject and said SAPSII score of said subject.
30. The method of item 29, wherein said level of proADM and said SAPSII score are indicative of said adverse event, preferably mortality, of said subject occurring within 28 days or within 7 days.
31. The method of any one of items 1 to 30, wherein said method comprises determining said level of proADM, said SOFA score and said level of lactate of said subject.
32. The method of any one of items 1 to 31, wherein said subject suffers from a disease or medical condition.
33. The method of any one of items 1 to 32, wherein said subject is a critical ill patient, preferably wherein said subject is admitted to an intensive care unit.
34. The method of any one of items 1 to 33, wherein said subject suffers from a disease or medical condition and wherein said disease or medical condition is selected from the group consisting of respiratory disease, urinary tract infection, an inflammatory response related to infective and non-infective etiologies, systemic inflammatory response syndrome (SIRS), sepsis, severe sepsis, septic shock, organ failure(s), cardiovascular disease, diabetes mellitus, malignancy, liver disease, renal disease, immunodepression, viral infection, fungal infection, bacterial infection, gram-negative bacterial infection, gram-positive bacterial infection and immunosuppresion.
35. The method of any one of items 1 to 34, wherein said subject suffers from sepsis.
36. The method of any one of items 1 to 35, wherein said subject is an immunosuppressed subject, such as a subject suffering from human immunodeficiency virus (HIV), a subject undergoing radiotherapy, and/or a subject receiving immunosuppressive drugs
37. The method of any one of items 1 to 36, wherein said subject suffers from a respiratory disease, preferably an infection of the lower respiratory tract.
38. The method of item 37, wherein said level of at least one histone in said sample of said subject suffering from said respiratory disease is indicative of mortality occurring within 7 days.
39. The method of any one of items 1 to 38, wherein said subject suffers from a urinary tract infection
40. The method of item 39, wherein said level of at least one histone in said sample of said subject suffering from said urinary tract infection is indicative of mortality occurring within 28 days.
41. The method of any one of items 1 to 40, wherein said subject suffers from a malignancy.
42. The method of item 41, wherein said level of at least one histone in said sample of said subject suffering from said malignancy is indicative of mortality occurring within 7 days.
43. The method of any one of items 1 to 42, wherein the level of the marker or the parameter is determined during about 12 h of admission of said subject.
44. The method of any one of items 1 to 43, wherein said sample is a body fluid, blood, blood plasma, blood serum, or urine.
45. The method of any one of items 1 to 44, wherein said level of at least one histone and/or of proADM is/are determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, and rare cryptate assay.
46. The method of item 45, wherein the method is an immunoassay and wherein the assay is performed in homogeneous phase or in heterogeneous phase.
47. The method of item 45 or 46, wherein the method is an immunoassay comprising the steps of:
a) contacting the sample with
(i) a first antibody or an antigen-binding fragment or derivative thereof specific for a first epitope of a histone or proADM, and
(ii) a second antibody or an antigen-binding fragment or derivative thereof specific for a second epitope of the histone or proADM; and
b) detecting the binding of the first and second antibodies or antigen-binding fragments or derivates thereof to said first histone or to proADM.
48. The method of item 47, wherein one of the first or second antibodies is labeled and the other antibody is bound to, or is capable of being selectively bound to a solid phase.
49. The method of item 47 or 48, wherein the first antibody and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said at least one histone or to said proADM to be detected, a measurable signal which permits detection of the resulting sandwich complexes in the measuring solution is generated.

50. The method of item 49, wherein the labelling system comprises a rare earth cryptate or chelate in combination with a fluorescent or chemiluminescent dye, in particular of the cyanine type.

51. The method of item 45, wherein the MS analysis method is reaction monitoring (SRM), multiple reaction monitoring (MRM) or parallel reaction monitoring (PRM).

52. The method of any one of items 1 to 51, wherein said at least one histone is histone H4 and wherein at least a peptide of the sequence spanning amino acid residues 22 to 102 of histone H4 according to SEQ ID NO:1 is determined.

53. The method of any one of items 1 to 52, wherein said at least one histone is histone H4 and wherein at least a peptide of the sequence is determined selected from the group consisting of an amino acid sequence spanning residues 47 to 59 of SEQ ID NO:1, residues 68 to 79 of SEQ ID NO: 1, residues 60 to 67 of SEQ ID NO: 1, residues 22 to 30 of SEQ ID NO: 1, residues 67 to 78 of SEQ ID NO: 1, residues 92 to 102 of SEQ ID NO: 1, residues 22 to 34 of SEQ ID NO: 1, residues 46 to 102 of SEQ ID NO: 1, residues 46 to 55 of SEQ ID NO: 1, residues 80 to 91 of SEQ ID NO: 1, residues 24 to 35 of SEQ ID NO: 1, and residues 68 to 77 of SEQ ID NO: 1.

54. The method of any one of items 1 to 53, wherein said at least one histone is histone H2A and wherein at least a peptide of the sequence spanning amino acid residues 20 to 118 of histone H2A according to SEQ ID NO: 2 is determined.

55. The method of any one of items 1 to 54, wherein said at least one histone is histone H2A and wherein at least a peptide of the sequence is determined selected from the group consisting of an amino acid sequence spanning residues 21 to 53 of SEQ ID NO: 2, residues 21 to 29 of SEQ ID NO: 2, residues 30 to 53 of SEQ ID NO: 2, residues 120 to 129 of SEQ ID NO: 2, residues 21 to 29 of SEQ ID NO: 2, residues 82 to 88 of SEQ ID NO: 2, residues 89 to 95 of SEQ ID NO: 2, and residues 100 to 118 of SEQ ID NO: 2.

56. The method of any one of items 1 to 55, wherein said at least one histone is histone H3 and wherein at least a peptide of the sequence spanning amino acid residues 27 to 62 of histone H3 according to SEQ ID NO: 3 is determined.

57. The method of any one of items 1 to 56, wherein said at least one histone is histone H3 and wherein at least a peptide of the sequence spanning amino acid residues 27 to 37 of SEQ ID NO: 3 and/or spanning amino acid residues 52 to 62 of SEQ ID NO: 3 is determined.

58. The method of any one of items 1 to 57, wherein said at least one histone is histone H2B and wherein at least a peptide of the sequence spanning amino acid residues 41 to 69 of histone H2B according to SEQ ID NO: 4 is determined.

59. The method of any one of items 1 to 58, wherein said at least one histone is histone H2A and wherein at least a peptide or a fragment thereof is determined selected from the group consisting of SEQ ID NOs: 7, 8, 9 and 10 is determined.

60. The method of any one of items 1 to 59, wherein said at least one histone is histone H4 and wherein at least a peptide or a fragment thereof selected from the group consisting of SEQ ID NOs: 11, 12, 13, 14, 15 and 16 is determined.

61. A kit for carrying out the method according to any one of items 1 to 60, wherein said kit comprises
    (i) detection reagents for determining said level of at least one histone in said sample of said subject, and
      reference data including said reference level of at least one histone, and wherein an increase in the level of at least one histone in said sample of said subject as compared to said reference level of at least one histone is indicative of an adverse event of said subject; and/or
    (ii) detection reagents for determining said level of proADM in said sample of said subject, and
      reference data including said reference level of proADM, and
      wherein an increase in the level of proADM in said sample of said subject as compared to said reference level of proADM is indicative of an adverse event of said subject.

62. A kit for carrying out the method according to any one of items 1 to 29, wherein said kit comprises detection reagents for determining said level of proADM in said sample of said subject, and reference data including said reference level of proADM, and wherein a decrease in the level of proADM or a similar level of proADM in said sample of said subject as compared to said reference level of proADM is indicative that an adverse event of said subject does not occur, preferably within about 28 days.

63. Use of the kit according to item 61 or 62 in the method of any one of the items 1 to 60.

64. Use of the kit according to item 63 for the diagnosis, prognosis, risk assessment, and/or risk stratification of an adverse event of a subject,
    (i) wherein said level of at least one histone is determined in said sample of said subject,
      wherein said level of said at least one histone is compared to said reference level of at least one histone, and
      wherein said adverse event of said subject is identified based on the comparison of said level of at least one histone determined in said sample and said reference level of at least one histone; and/or
    (ii) wherein said level of proADM is determined in said sample of said subject,
      wherein said level of proADM is compared to said reference level of proADM, and
      wherein said adverse event of said subject is identified based on the comparison of said level of proADM determined in said sample and said reference level of proADM.

65. Use of a kit for the diagnosis, prognosis, risk assessment, and/or risk stratification of an adverse event of a subject,
    (i) wherein said kit comprises detection reagents for determining a level of at least one histone in a sample of a subject, and
      wherein said level of at least one histone is indicative of said adverse event of said subject s; and/or
    (ii) wherein said kit comprises detection reagents for determining a level of proADM in a sample of a subject, and
      wherein said level of said proADM is indicative of said adverse event of said subject.

The present invention also relates to the following items in preferred embodiments:

1. A method for the diagnosis, prognosis, risk assessment, and/or risk stratification of an adverse event of a subject, wherein said method comprises
   determining a level of proadrenomedullin (proADM) in a sample of said subject, and wherein said level of proADM is indicative of said adverse event of said subject.
2. The method of item 1, wherein
   said level of proADM is compared to a reference level of proADM; and wherein said adverse event of said subject is identified based on the comparison.
3. The method of item 1 or 2,
   wherein a decrease in the level or a lower level or an equal level of said proADM of said subject as compared to said reference level of said proADM is indicative that the adverse event does not occur, preferably within about 28 days; or
   wherein an increase in the level of proADM or higher level of proADM as compared to the reference level of proADM is indicative of said adverse event of said subject, wherein preferably said adverse event occurs within about 28 days.
4. The method of any one of items 1 to 3, wherein the reference level of proADM is about 0.7 nmol/L to about 2.0 nmol/L, preferably about 0.8 nmol/L to about 1.9 nmol/L.
5. The method of any one of items 1 to 4, wherein said adverse event is mortality.
6. The method of item 5, wherein a level of proADM above about 0.9 nmol/L, preferably above about 1.9 nmol/L, more preferably above about 2.0 nmol/L is indicative for non-survival of the subject within about 28 days.
7. The method of any one of items 1 or 2, wherein a level of proADM below about 1.0 nmol/L, preferably below about 0.9 nmol/L, most preferably below about 0.88 nmol/L is indicative for the subject to survive within about 28 days.
8. The method of any one of items 1 to 7, wherein further the sequential organ failure assessment score (SOFA score) of said subject is determined.
9. The method of any one of items 2 to 5, wherein
   the reference level of proADM is about 1.8 nmol/L for subjects having symptoms corresponding to a SOFA score of 6;
   the reference level of proADM is about 3.2 nmol/L for subjects having symptoms corresponding to a SOFA score of 7 to 12; or
   the reference level of proADM is about 5.5 nmol/L for subjects having symptoms corresponding to a SOFA score of 13.
10. The method of any one of items 1 to 5 or 9, wherein
    a decrease in the level or an equal level of proADM of said subject as compared to the reference level of proADM that is about 1.8 nmol/L and a SOFA score of ≤6 of said subject are indicative that said adverse event does not occur;
    a decrease in the level or an equal level of proADM of said subject as compared to the reference level of proADM that is about 3.2 nmol/L and a SOFA score of 7 to 12 of said subject are indicative that said adverse event does not occur; or
    a decrease in the level or an equal level of proADM of said subject as compared to the reference level of proADM that is about 5.6 nmol/L and a SOFA score of ≥13 of said subject are indicative that said adverse event does not occur; and
    wherein preferably said adverse event does not occur within about 28 days.
11. The method of any one of items 1 to 5 or 9, wherein
    an increase in the level of proADM of said subject as compared to the reference level of proADM that is about 1.8 nmol/L and a SOFA score of ≤6 of said subject are indicative of said adverse event of said subject;
    an increase in the level of proADM of said subject as compared to the reference level of proADM that is about 3.2 nmol/L and a SOFA score of 7 to 12 of said subject are indicative of said adverse event of said subject; or
    an increase in the level of proADM of said subject as compared to the reference level of proADM that is about 5.6 nmol/L and a SOFA score of ≥13 of said subject are indicative of said adverse event of said subject,
    wherein preferably said adverse event occurs within about 28 days.
12. The method of any one of items 8 to 11, wherein the SOFA score of said subject is increased based on the level of proADM of said subject, and wherein said modified SOFA score is indicative of said adverse event.
13. The method of item 12, wherein the SOFA score of the subject is increased by one if the subject has a proADM level that is higher than about 1.8 nmol/L.
14. The method of any one of items 3 to 5 and 9 to 13, wherein the increase in the level of said proADM is about twice as high as said reference level of proADM.
15. The method of any one of items 1 to 14, wherein said proADM is midregional proadrenomedullin (MR-proADM) or mature ADM.
16. The method of any one of items 1 to 15, wherein said level of proADM of said subject is indicative of said adverse event, preferably mortality, of said subject occurring within 28 days.
17. The method of any one of items 1 to 16, wherein said method further comprises determining at least one marker and/or parameter of said subject selected from the group consisting of a level of at least one histone, a level of procalcitonin (PCT) in said sample, the simplified acute physiology score (SAPSII score), the Acute Physiology and Chronic Health Evaluation II (APACHE II) score of said subject, the Pneumonia Severity Index (PSI) score of said subject and the CURB-65 score of said subject.
18. The method of item 17, wherein the level of the marker or the parameter is determined during about 12 h of admission of said subject.
19. The method of any one of items 1 to 18, wherein the level of proADM is determined during about 12 h of admission of said subject.
20. The method of any one of items 1 to 19, wherein said method comprises determining said level of proADM and the SOFA score of said subject.
21. The method of any one of items 1 to 20, wherein said subject suffers from a disease or medical condition.
22. The method of any one of items 1 to 21, wherein said subject is a critical ill patient, preferably wherein said subject is admitted to an intensive care unit or an emergency department, preferably said subject is admitted to an intensive care unit.
23. The method of any one of items 1 to 22, wherein said subject suffers from a disease or medical condition and wherein said disease or medical condition is selected from the group consisting of respiratory disease, urinary tract infection, an inflammatory response related to infective and non-infective etiologies, systemic inflammatory response syndrome (SIRS), sepsis, severe sepsis, septic shock, organ failure(s), cardiovascular disease, diabetes mellitus, malignancy, liver disease, renal disease, immunodepression, viral infection, fungal infection, bacterial infection, gram-negative bacterial infection, gram-positive bacterial infection and immunosuppresion.

24. The method of any one of items 1 to 23, wherein said subject suffers from sepsis.

25. The method of any one of items 1 to 24, wherein said subject is an immunosuppressed subject, such as a subject suffering from human immunodeficiency virus (HIV), a subject undergoing radiotherapy, and/or a subject receiving immunosuppressive drugs.

26. The method of any one of items 1 to 25, wherein said sample is a body fluid, blood, blood plasma, blood serum, or urine.

27. The method of any one of items 1 to 26, wherein said level of proADM is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, and rare cryptate assay.

28. The method of item 27, wherein the method is an immunoassay and wherein the assay is performed in homogeneous phase or in heterogeneous phase.

29. The method of item 28, wherein the method is an immunoassay comprising the steps of:
   a) contacting the sample with
      (i) a first antibody or an antigen-binding fragment or derivative thereof specific for a first epitope of proADM, and
      (ii) a second antibody or an antigen-binding fragment or derivative thereof specific for a second epitope of proADM; and
   b) detecting the binding of the first and second antibodies or antigen-binding fragments or derivates thereof to proADM.

30. The method of item 29, wherein one of the first or second antibodies is labeled and the other antibody is bound to, or is capable of being selectively bound to a solid phase.

31. The method of item 29 or 30, wherein the first antibody and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said proADM to be detected, a measurable signal which permits detection of the resulting sandwich complexes in the measuring solution is generated.

32. The method of item 31, wherein the labelling system comprises a rare earth cryptate or chelate in combination with a fluorescent or chemiluminescent dye, in particular of the cyanine type.

33. A kit for carrying out the method according to any one of items 1 to 32, wherein said kit comprises detection reagents for determining said level of proADM in said sample of said subject, and reference data including said reference level of proADM, and wherein an increase in the level of proADM in said sample of said subject as compared to said reference level of proADM is indicative of an adverse event of said subject.

34. A kit for carrying out the method according to any one of items 1 to 32, wherein said kit comprises detection reagents for determining said level of proADM in said sample of said subject, and reference data including said reference level of proADM, and wherein a decrease in the level of proADM or a similar level of proADM in said sample of said subject as compared to said reference level of proADM is indicative that an adverse event of said subject does not occur within about 28 days.

35. Use of the kit according to item 33 or 34 in the method of any one of the items 1 to 29.

36. Use of the kit according to item 33 or 34 for the diagnosis, prognosis, risk assessment, and/or risk stratification of an adverse event of a subject,
   wherein said level of proADM is determined in said sample of said subject,
   wherein said level of proADM is compared to said reference level of proADM, and
   wherein said adverse event of said subject is identified based on the comparison of said level of proADM determined in said sample and said reference level of proADM.

37. Use of a kit for the diagnosis, prognosis, risk assessment, and/or risk stratification of an adverse event of a subject,
   wherein said kit comprises detection reagents for determining a level of proADM in a sample of a subject, and
   wherein said level of said proADM is indicative of said adverse event of said subject.

38. The method of any one of items 2 to 32, wherein said comparison is performed in a computer system.

39. The method of item 1 to 32, wherein the determined value of proADM is used in the calculation of a score indicative of said diagnosis, prognosis, risk assessment, and/or risk stratification of an adverse event in the subject.

40. The method of item 40, wherein additionally at least one further marker and or parameter of the subject is used for the calculation of said score.

41. The method of item 40, wherein the at least one further marker and/or parameter of said subject is selected from the group consisting of a level of at least one histone, a level of procalcitonin (PCT) in said sample, the simplified acute physiology score (SAPSII score), the Acute Physiology and Chronic Health Evaluation II (APACHE II) score of said subject, the Pneumonia Severity Index (PSI) score of said subject and the CURB-65 score of said subject.

As used herein, the terms "comprising" and "including" or grammatical variants thereof are to be taken as specifying at least the stated features, integers, steps or components but do not preclude the addition of one or more additional features, integers, steps, components or groups thereof. This term encompasses the terms "consisting of" and "consisting essentially of" that are understood to specify only the stated feature, integers, steps or components to the exclusion of any additional features.

Thus, the terms "comprising"/"including"/"having" mean that any further component (or likewise features, integers, steps and the like) can/may be present.

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The term "about" preferably refers to ±10% of the indicated numerical value, more preferably to ±5% of the indicated numerical value, and in particular to the exact numerical value indicated.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 amino acids" refers to the range of 23 to 28 amino acids, in particular the range of 24 to 26 amino acids, and preferably refers to the specific value of 25 amino acids.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having a prenatal disorder or condition) and "disease" populations, e.g. subjects experiencing/having/suffering from an adverse event, e.g. mortality. For any particular marker (like MR-proADM), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. the abnormal event. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples (or adverse event) might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +1-5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of the adverse event, particularly mortality. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disorder or condition (adverse outcome), i.e. "diseased group". In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse event/outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value; see, e.g., Dowdy and Wearden, Statistics for Research, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

The present invention is further described by reference to the following non-limiting figures.

FIG. 1: Kaplan Meier analysis for mortality prediction at 28 days

Figure 2:
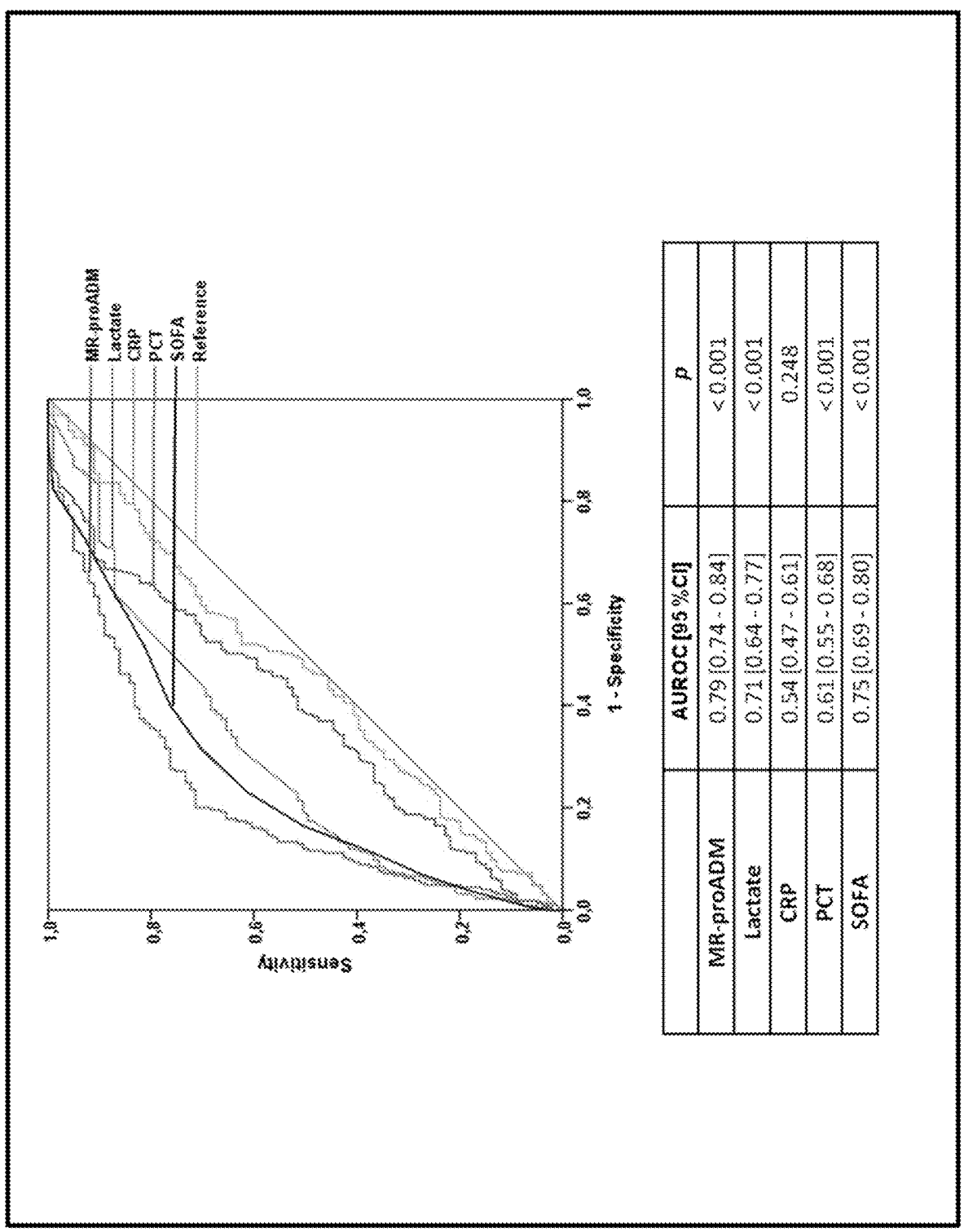

FIG. 2: AUROC analysis for identifying non-survivors at 28 days (entire cohort)

Figure 3:
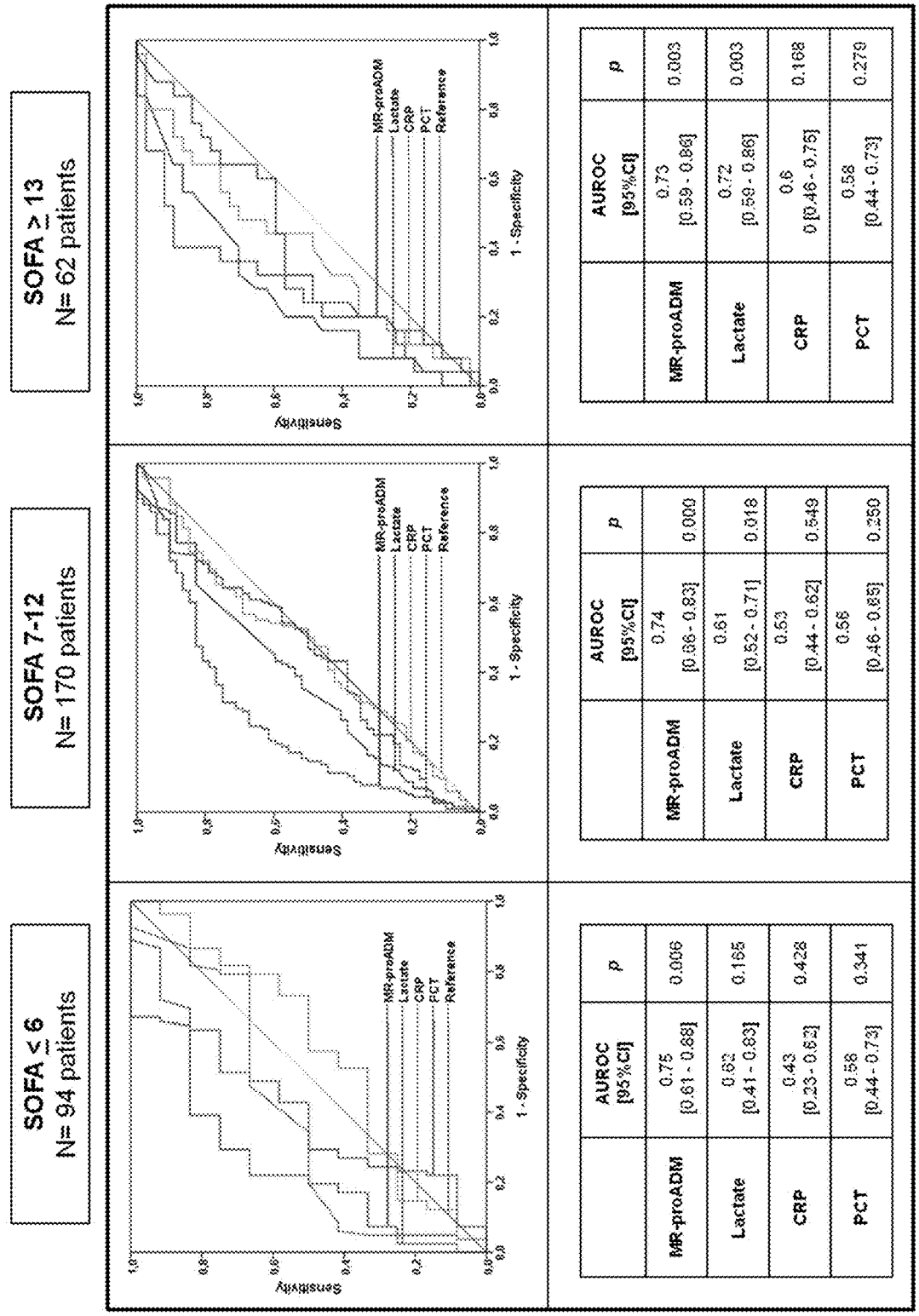

FIG. 3: AUROC analysis for identifying non-survivors at 28 days depending on biomarker levels in the three severity groups.

Figure 4:
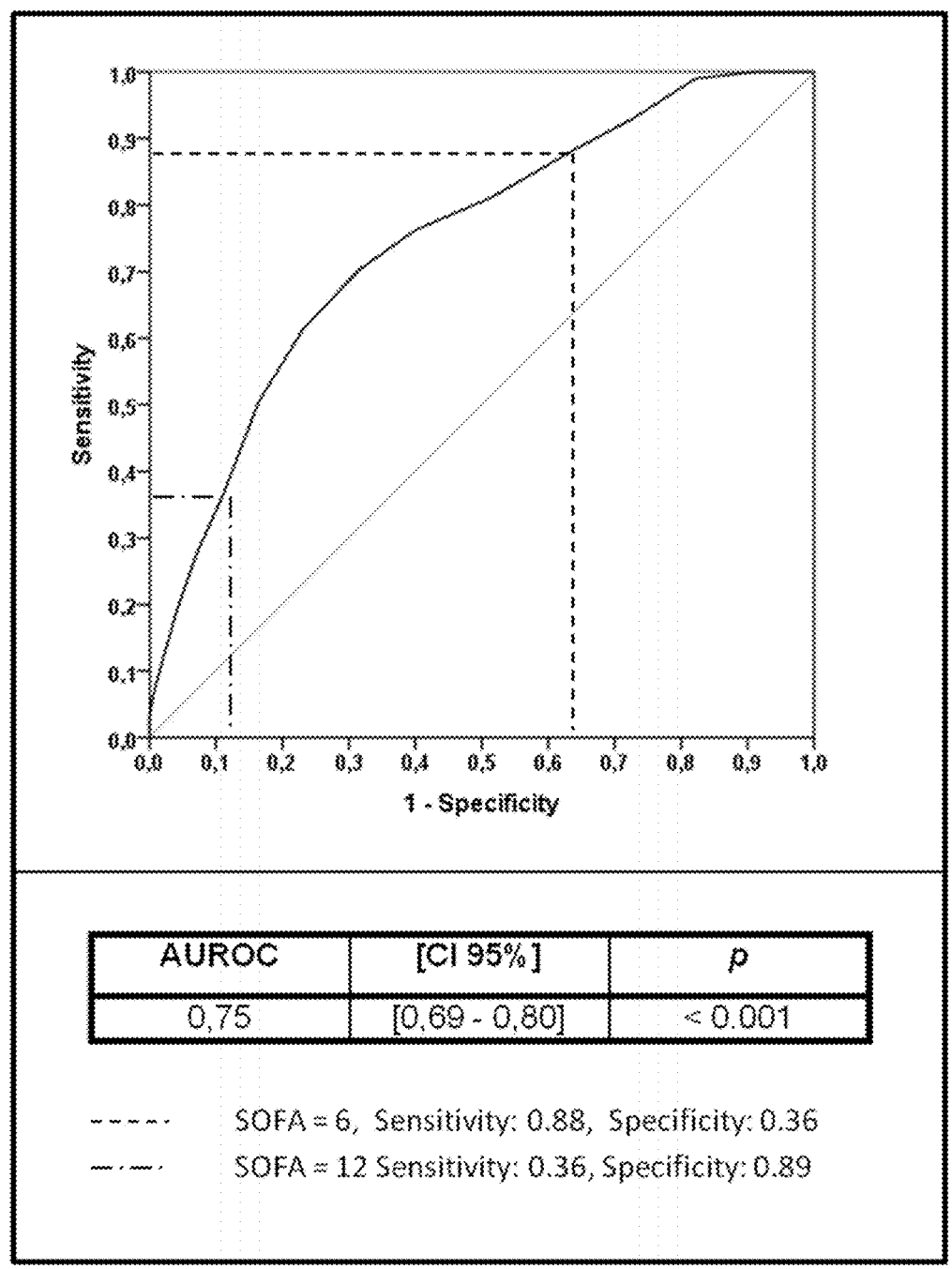

FIG. 4: AUROC analysis for identifying non-survivors at 28 days based upon SOFA score.

The present invention is further described by reference to the following non-limiting examples.

Example 1

Methods:
Study Population

Two hundred and thirty-seven critically ill patients admitted to the medical intensive care unit of 'centre hospitalier universitaire (CHU) de Dijon Bourgogne' from the $1^{st}$ of Jun. 2013 to the $14^{th}$ of Jun. 2014 were consecutively enrolled in the clinical study. Patients younger than 18 years were excluded. The study was approved by the local institutional review board. Before enrolment, written informed consent was obtained from patients themselves or from the patient's next of kin. All patients showed a broad spectrum of diseases including cardiovascular disease, diabetes mellitus, malignancy, respiratory disease, liver disease, renal disease and immunodepression and were monitored until discharge or death in the hospital. Based on retrospective review of medical records, imaging and microbiology results two independent physicians classified the patients on the day of admission as either non-sepsis (systemic inflammatory response syndrome (SIRS) or no SIRS), severe sepsis or septic shock according to international standardized criteria (Bone, Balk et al. 1992). A blood sample was taken on the day of admission, i.e. during the first 24 hours. Baseline demographics and clinical data including medical history, results from physical examination, routine blood analyses (e.g. blood cultures), non-laboratory diagnostic investigations (e.g. SIRS criteria, organ failure criteria), therapeutic interventions (e.g. mechanical ventilation (MV), vasopressors and renal replacement therapy (RRT)) as well as outcome parameters (e.g. length of stay, all cause mortality) were recorded. The sequential organ failure assessment (SOFA) score, based on six organ parameters, and the simplified acute physiology score (SAPS II), based on 17 mainly physiology variables, were calculated on admission (Le Gall, Lemeshow et al. 1993; Vincent, Moreno et al. 1996).

Biomarkers

Serum lactate levels were measured by colorimetric assay using the e501 module analyser from Roche Diagnostics, Meylan, France. Reference limit for lactate was 0.5-2.2 mmol/L. MR-proADM (midregional proadrenomedullin), copeptin and PCT (procalcitonin) levels were determined in plasma samples using ultrasensitive assays, such as KRYPTOR random access analyser (Thermo Scientific B•R•A•H•M•S). The levels of histone H2A, H2B, H3 and H4 as well as the level of Aldolase B were determined in the plasma samples by e.g. selected reaction monitoring or multiple reaction monitoring (SRM/MRM) assays as described in the following. Specific peptides derived from the markers were measured by LC-MS/MS technology (TSQ Quantiva mass spectrometer (MS); ThermoFisher Scientific). Identified peptide sequences and fragmentation ions thereof, so-called Transitions, for each peptide were found to be useful surrogates for monitoring marker proteins levels in a blood sample. Optimization was done on synthetic peptides which can be isotopically heavy labeled. Best peptides regarding signal to noise were selected. Optimal retention time and at least 4 best transitions were set up for each peptide.

Exemplary MS Quantification and Choice of Peptides and Transitions 5 uL of each clinical plasma sample was added to 20 uL of 8M Urea/2.5% n-propanol/300 mM Tris/10 mM DTT pH 8.5 and incubated at 37 C for one hour. 500 mM iodoacetic acid prepared in 1M ammonium bicarbonate was added to each sample well and incubated in the dark at room temperature for one hour. 113 uL of 50 mM Tris/5 mM CaCl2) pH 8.0 were added to each well. Trypsin (Thermo Fisher Scientific) was rehydrated with 150 uL of 25 mM acetic acid is added with a ratio 1:10 (total protein content:protease) and incubated at 37 C for 20 hours. Digestion was finally quenched with the additional of 2 uL of formic acid. Glucagon (1 ng/uL) and standard heavy peptides were then added before injection.

SRM assays were developed on a triple quadrupole mass spectrometer TSQ Quantiva coupled with HPLC Ultimate 3000 (Thermo Fisher Scientific). Reverse phase separations were carried out in a 20 min linear gradient from 5 to 40% B, with a total run time of 40 min (Solvent A: Water 0.2% FA, Solvent B: ACN 0.2% FA). The flow rate during the linear gradient was set to 240 µL/min. The total injection volume was 160 µL for all samples and points on the curve. A 150 mm ×2.1 mm Accucore aQ column (ThermoFisher Scientific) was run at a temperature of 50° C.

Optimization was performed on heavy labeled synthetic peptides, incorporating 13C- and 15N-labeled arginine or lysine (ThermoFisher Scientific or New England Peptide). Individual instrument parameters such as collision energy, tube lens, and dwell time were automatically tested for every transition. After multiple iterations, the optimized list of peptides and transitions (i.e. highest intensity signal and least overlap with other transitions), and corresponding retention times were finalized with at least four fragment transitions per peptide chosen.

Peptides were identified by co-eluting light and heavy-labeled transitions in the chromatographic separation. Pinpoint (Thermo Fisher Scientific) and Skyline (MacCoss Lab) softwares were used for time alignment, relative quantification of the transitions and targeted protein quantification.

Relative and absolute quantifications of the markers were performed by employing the exemplary methods as described in the following.

Relative Quantification:

1. Determining increased or decreased presence of the marker by comparing the SRM signature peak area from a given peptide detected in biological sample to the same SRM signature peak area of the same fragment peptide in at least a second, third, fourth or more biological samples.

2. Determining increased or decreased presence of the marker by comparing the SRM signature peak area from a given peptide detected in a biological sample to SRM signature peak areas developed from fragment peptides from other proteins, in other samples derived from different and separate biological sources, where the SRM signature peak area comparison between the 2 samples for a peptide fragment are normalized to amount of protein analyzed in each sample.

3. Determining increased or decreased presence of the marker by comparing the SRM signature peak area for a given peptide to the SRM signature peak areas from other fragment peptides derived from different proteins within the same biological sample in order to normalize changing levels of the maker to levels of other proteins that do not change their levels of expression under various cellular conditions.

4. These assays were applied to both unmodified fragment peptides and for modified fragment peptides, e.g. the histones protein, where the modifications included, but were not limited to phosphorylation and/or glycosylation, acetylation, methylation (mono, di, tri), citrullination, ubiquitinization and where the relative levels of modified peptides were determined in the same manner as determining relative amounts of unmodified peptides.

Absolute Quantification of a Given Peptide:

Comparing the SRM/MRM signature peak area for a given fragment peptide from the marker in an individual biological sample to the SRM/MRM signature peak area of an internal fragment peptide standard spiked into the protein lysate from the biological sample.

The internal standard was a labeled synthetic version of the fragment peptide from the marker protein that was being interrogated or the labeled recombinant protein. This standard was spiked into a sample in known amounts before or after digestion, and the SRM/MRM signature peak area was determined for both the internal fragment peptide standard and the native fragment peptide in the biological sample separately, followed by comparison of both peak areas.

Such an assay was applied to unmodified fragment peptides and modified fragment peptides, where the modifications included but are not limited to phosphorylation and/or glycosylation, acetylation, methylation (mono, di, tri), citrullination, ubiquitinization, and where the absolute levels of modified peptides were determined in the same manner as determining absolute levels of unmodified peptides.

Histone H4 was also measured by an immunoassay. The Histone H4 Immuno-Assay (H4 IA) consist of a mouse monoclonal antibody (mAb) raised against a synthetic peptide (amino acids 46-56 of SEQ ID NO: 1) coupled to MagPlex-C Micropheres (Luminex, Austin Tex.), and a biotinylated sheep polyclonal antibody (pAb) raised against a synthetic peptide (amino acids 67-78 of SEQ ID NO 1). A synthetic peptide (amino acids 46-102 of SEQ ID NO: 1) was used as standard material. Samples were measured on a MAgPix with xPonent 4.2 System (Luminex, Austin Tex.). Data was analyzed using 5 parameter logistic regression from JMP-12 (SAS statistical software, UK).

Statistical Analysis

All analyses were performed using the software R 3.0.2.

The data is expressed as median and interquartile range [IQR] in brackets.

As all analyzed biomarkers show highly right-skewed distributions, values were $\log_{10}$-transformed prior to inclusion into regression models in order to decrease the impact of extreme values on the model fit.

Values below limit of quantification (LoQ) were replaced by a small value below LoQ. Missing values were not replaced. Each model includes all patients with complete data on all variables in the model.

P-values <0.05 were considered as significant.

For survival analyses, follow-up was censored at 3, 7 or 28 days after ICU admission (maximal follow-up period (FUP)), as appropriate. Patients lost to follow-up before the evaluated FUP (i.e. due to early discharge or relocation to a different ward) were censored at the day of their last visit on the ICU. Patients alive at the maximal FUP were censored at this day. For time-dependent outcome variables, Cox regression models were used. Displayed results are the Likelihood-Ratio-$\chi^2$ test (L.R. $\chi^2$ and p-value), C index (Harrel) and standardized hazard ratios (HR). Hazard ratios herein refer to a two-fold change in the biomarkers level (upper vs. lower quartile of biomarkers). In adjusted models, adjusting variables were included into the model in order to determine the additional effect of biomarkers on model performance.

Results:

The study population comprised 237 patients. Two patients (one patient without SIRS, one sepsis patient) had to be excluded from analyses due to conflicting documentation of mortality data. One hundred and seventy-two patients (73%) presented with severe sepsis or septic shock, 15 patients (6%) with SIRS and 49 patients (21%) without SIRS. Median age was 67 [59-77 years]years. The majority of patients was male (60%). Most frequent underlying conditions were cardiovascular diseases (35%), diabetes mellitus (31%) and malignancies (27%) followed by respiratory disease (16%), liver disease (12%), renal disease (12%) and immunodepression (7%). Most frequent site of infection was the lower respiratory tract (46%) and urinary tract (45%). SAPS II score (56 [40-69 points] points) and SOFA score (9 [6-12 points] points) were increased on admission. Organ failures were most frequently respiratory failure (61%), circulatory shock (56%) and renal failure (41%). Accordingly, many patients required MV (78%), vasopressors (68%) and RRT (37%) during ICU stay. All cause ICU mortality was 32%, median length of ICU stay was 5.4 [2.5-10.6] days.

We analyzed short term (e.g. at day 3 and 7, i.e. 3 day and 7 day) and long term (at day 28, i.e. 28 day) mortality in all 235 critically ill patients using uni- and bivariate Cox regression models adjusted for age and sex. Twenty-three patients (10%) had died by day 3, 49 patients (21%) had died by day 7 and 74 patients (32%) had died by day 28 after ICU admission. In addition, mortality was analyzed in subpopulations of patients with lower respiratory tract infection, urinary tract infection (UTI) and malignancies using univariate Cox regression models adjusted for age and sex. Twenty-seven patients (25%) of 109 patients with lower respiratory tract infection had died by day 7, 34 patients (36%) of 94 patients with UTI had died by day 28 and 16 patients (25%) of 64 patients with malignancies had died by day 7 after ICU admission. The power of each Cox regression model to discriminate survivors from non-survivors is reflected by the C index ranging from 0 to 1 with best predictive Cox regression models resulting in a C index close to 1. In addition, HR are calculated with HR>0 indicating a worse prognosis and HR<0 indicating a protective effect of the variable.

Among all analyzed variables, the SAPS II score on ICU admission shows the best prediction at 3 day (C index 0.876, HR per IQR 8.42), 7 day (C index 0.809, HR per IQR 5.15) and 28 day (C index 0.776, HR per IQR 4.19) mortality, followed by the SOFA score on ICU admission in prediction of 3 day (C index 0.866, HR per IQR 6.68) and 7 day mortality (C index 0.778, HR per IQR 3.82) in all 235 critically ill patients (Table 1-Table 3). Similar results are obtained in the subgroup of sepsis patients and for prediction of 7 day mortality in critically ill patients with lower respiratory tract infection for the SAPS II score (C index 0.773, HR per IQR 3.47) (Table 4).

In comparison, MR-proADM discriminates survivors and non-survivors best among all biomarkers on day 7 (C index 0.769, HR per IQR 4.53) and day 28 (C index 0.765, HR per IQR 4.86) after ICU admission in all critically ill patients (Table 2, Table 3). It is superior to the SOFA score in predicting 28 d mortality in all critically ill patients (Table 3). Similar results are obtained in the subgroup of sepsis patients. In bivariate analysis, MR-proADM improves the performance of SAPS II or SOFA for prediction of 7 day mortality (C index 0.832 for combined model of SAPS II and MR-proADM compared to C index 0.809 for SAPS II alone) and the performance of SAPS II for prediction of 28 day mortality (C index 0.810 for combined model of SAPS II and MR-proADM compared to C index 0.776 for SAPS II alone) in all critically ill patients (Table 2, Table 3). There is no improved prognostic value in a combined model of SAPS II or SOFA and MR-proADM for prediction of 3 day mortality in these patients (Table 1).

In comparison to other biomarkers and scores, PCT (e.g. C index 0.689, HR per IQR 1.90 for prediction of 28 day mortality in all critically ill patients) and aldolase B (e.g. C index 0.667, HR per IQR 1.47 for prediction of 28 day mortality in all critically ill patients) on ICU admission show moderate association with mortality in all critically ill patients or subgroups thereof (e.g. Table 1). However, in a bivariate Cox regression model PCT improves the prognostic value of SAPS II or SOFA for prediction of 28 day mortality in all critically ill patients (e. g. combined model of SAPS II and PCT results in a C index of 0.786 compared to 0.776 for SAPS II in univariate analysis) (e.g. Table 3). In addition, a bivariate Cox regression model including aldolase B improves association of MR-proADM with 7 day mortality in all critically ill patients (combined model of MR-proADM and aldolase B with a C index of 0.780 compared to univariate model of MR-proADM with a C index of 0.769) (Table 2). The prediction was not further improved by PCT or aldolase B to SAPS II, MR-proADM or histones in other mortality analyses (Table 1-Table 3).

The levels of the histones H2A, H2B, H3 and H4 on ICU admission were strongly associated with 3 day (e.g. H2B C index 0.793, HR per IQR 2.76), 7 day (e.g. H2B C index 0.768, HR per IQR 2.40) and 28 day (e.g. H2B C index 0.752, HR per IQR 2.40) mortality in all critically ill patients (Table 1-Table 3). Similar results are obtained in the subgroup of sepsis patients. Among all histones H2B performs best, followed by H4, H2A and H3 (Table 1-Table 6). Comparing the performance of histones H2A, H2B, H3 and H4 to other biomarkers, there is a striking prognostic value of histones for short term (3 and 7 day) mortality, i.e. while H2B may be inferior to MR-proADM in prediction of 28 day mortality (MR-proADM C index 0.765 versus H2B C index 0.752). H2B and MR-proADM are comparably associated with 7 day mortality (H2B C index 0.793 versus MR-proADM C index 0.786) and H2B is superior to MR-proADM for prediction of 3 day mortality (H2B C index 0.768 versus MR-proADM C index 0.769) in all critically ill patients (Table 1-Table 3).

In bivariate Cox regression models, histones H2A, H2B, H3 and H4 improve the performance of SAPS II or SOFA (e.g. combined model of H2B and SAPS II C index 0.811 compared to univariate model of SAPS II C index 0.776 for prediction of 28 day mortality) and MR-proADM (combined model of H2B and MR-proADM C index 0.795 compared to univariate model of MR-proADM C index 0.765 for prediction of 28 day mortality) (Table 1-Table 3). In critically ill patients with lower respiratory tract infection histones H2A, H2B, H3 and H4 on ICU admission are the best predictor of 7 day mortality among the biomarkers (e.g. H2B C index 0.785, HR per IQR 2.56) (Table 4). In critically ill patients with UTI histones H2A, H2B, H3 and H4 are strongest associated with 28 day mortality among all variables on ICU admission (e.g. H2B C index 0.764, HR per IQR 2.52) (Table 5). Histones H2A, H2B, H3 and H4 on ICU admission show strongest association with 7 day mortality (e.g. H2B C index 0.815, HR per IQR 4.79) among all variables in critically ill patients admitted to the ICU with malignancies (Table 6).

TABLE 1

Table 1: Uni- and bivariable Cox regression analysis for 3 day mortality in all critically patients Twenty-four patients of a total number (n) of 235 critically ill patients had died by day 3 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment; MR-proADM: midregional proadrenomedullin; PCT: procalcitonin; Histones are represented by histone H2A, H2B, H3 and H4; H4 was also measured by an immunoassay (IA)).

| Model | N | Events | L.R. $\chi^2$ | df | p-value | C index | HR [95% CI] per ... IQR | ... 2fold change |
|---|---|---|---|---|---|---|---|---|
| SAPS II | 235 | 24 | 55.11 | 3 | <0.001 | 0.876 | 8.42 [4.38-16.19] | |
| SOFA | 235 | 24 | 41.78 | 3 | <0.001 | 0.866 | 6.68 [3.33-13.39] | |
| H2B | 235 | 24 | 29.31 | 3 | <0.001 | 0.793 | 2.76 [1.77-4.29] | 1.47 [1.24-1.73] |
| H4 | 235 | 24 | 28.24 | 3 | <0.001 | 0.786 | 2.70 [1.72-4.25] | 1.45 [1.23-1.72] |
| H2A | 235 | 24 | 28.14 | 3 | <0.001 | 0.787 | 2.45 [1.63-3.66] | 1.45 [1.23-1.72] |
| H4 IA | 228 | 23 | 26.61 | 3 | <0.001 | 0.779 | 14.35 [3.26-63.19] | 1.39 [1.16-1.66] |
| MR-proADM | 235 | 24 | 24.99 | 3 | <0.001 | 0.786 | 4.82 [2.08-11.18] | 2.05 [1.40-3.01] |
| H3 | 235 | 24 | 19.68 | 3 | <0.001 | 0.740 | 3.45 [1.54-7.70] | 1.23 [1.08-1.41] |
| Aldolase B | 235 | 24 | 14.65 | 3 | 0.002 | 0.721 | 1.65 [1.05-2.59] | 1.16 [1.02-1.32] |
| PCT | 235 | 24 | 12.08 | 3 | 0.007 | 0.705 | 1.49 [0.85-2.62] | 1.09 [0.97-1.23] |

TABLE 1-continued

Table 1: Uni- and bivariable Cox regression analysis for 3 day mortality in all critically patients Twenty-four patients of a total number (n) of 235 critically ill patients had died by day 3 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment; MR-proADM: midregional proadrenomedullin; PCT: procalcitonin; Histones are represented by histone H2A, H2B, H3 and H4; H4 was also measured by an immunoassay (IA)).

| Model | N | Events | L.R. $\chi^2$ | df | p-value | C index | HR [95% CI] per ... IQR | ... 2fold change |
|---|---|---|---|---|---|---|---|---|
| H2B + SAPS II | 235 | 24 | 61.95 | 4 | <0.001 | 0.885 | | |
| H4 + SAPS II | 235 | 24 | 61.83 | 4 | <0.001 | 0.884 | | |
| H2A + SAPS II | 235 | 24 | 61.70 | 4 | <0.001 | 0.884 | | |
| H4 IA + SAPS II | 228 | 23 | 61.51 | 4 | <0.001 | 0.898 | | |
| H3 + SAPS II | 235 | 24 | 57.02 | 4 | <0.001 | 0.878 | | |
| MR-proADM + SAPS II | 235 | 24 | 56.79 | 4 | <0.001 | 0.884 | | |
| PCT + SAPS II | 234 | 24 | 55.10 | 4 | <0.001 | 0.875 | | |
| Aldolase B + SAPS II | 234 | 24 | 54.97 | 4 | <0.001 | 0.876 | | |
| MR-proADM + H2B | 235 | 24 | 36.15 | 4 | <0.001 | 0.828 | | |
| H4 IA + SOFA | 228 | 23 | 50.05 | 4 | <0.001 | 0.887 | | |
| H2B + SOFA | 235 | 24 | 47.98 | 4 | <0.001 | 0.876 | | |
| H4 + SOFA | 235 | 24 | 47.56 | 4 | <0.001 | 0.876 | | |
| H2A + SOFA | 235 | 24 | 47.30 | 4 | <0.001 | 0.874 | | |
| H3 + SOFA | 235 | 24 | 43.63 | 4 | <0.001 | 0.863 | | |
| MR-proADM + SOFA | 235 | 24 | 42.27 | 4 | <0.001 | 0.872 | | |
| PCT + SOFA | 234 | 24 | 42.04 | 4 | <0.001 | 0.866 | | |
| Aldolase B + SOFA | 234 | 24 | 41.60 | 4 | <0.001 | 0.865 | | |
| MR-proADM + H4 | 235 | 24 | 35.29 | 4 | <0.001 | 0.826 | | |
| MR-proADM + H2A | 235 | 24 | 35.16 | 4 | <0.001 | 0.825 | | |
| MR-proADM + H4 IA | 228 | 23 | 32.60 | 4 | <0.001 | 0.809 | | |
| MR-proADM + H3 | 235 | 24 | 29.15 | 4 | <0.001 | 0.806 | | |
| H2B + Aldolase B | 234 | 24 | 31.35 | 4 | <0.001 | 0.799 | | |
| PCT + H2B | 234 | 24 | 29.29 | 4 | <0.001 | 0.791 | | |

TABLE 2

Table 2: Uni- and bivariable Cox regression analysis for 7 day mortality in all critically patients Forty-nine patients of a total number (n) of 235 critically ill patients had died by day 7 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4; H4 was also measured by an immunoassay (IA)).

| Model | N | Events | L.R. $\chi^2$ | df | p-value | C index | HR [95% CI] per ... IQR | ... 2fold change |
|---|---|---|---|---|---|---|---|---|
| SAPS II | 235 | 49 | 68.07 | 3 | <0.001 | 0.809 | 5.15 [3.26-8.13] | |
| SOFA | 235 | 49 | 50.64 | 3 | <0.001 | 0.778 | 3.82 [2.39-6.09] | |
| MR-proADM | 235 | 49 | 45.88 | 3 | <0.001 | 0.769 | 4.53 [2.55-8.04] | 1.99 [1.53-2.59] |
| H2B | 235 | 49 | 45.33 | 3 | <0.001 | 0.768 | 2.40 [1.76-3.28] | 1.39 [1.24-1.57] |

TABLE 2-continued

Table 2: Uni- and bivariable Cox regression analysis for 7 day mortality in all critically ill patients Forty-nine patients of a total number (n) of 235 critically ill patients had died by day 7 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4; H4 was also measured by an immunoassay (IA)).

| Model | N | Events | L.R. $\chi^2$ | df | p-value | C index | HR [95% CI] per . . . IQR | . . . 2fold change |
|---|---|---|---|---|---|---|---|---|
| H4 | 235 | 49 | 42.81 | 3 | <0.001 | 0.761 | 2.32 [1.68-3.18] | 1.37 [1.22-1.55] |
| H2A | 235 | 49 | 40.91 | 3 | <0.001 | 0.755 | 2.09 [1.57-2.78] | 1.36 [1.21-1.54] |
| H3 | 235 | 49 | 38.22 | 3 | <0.001 | 0.742 | 3.62 [2.07-6.34] | 1.24 [1.13-1.37] |
| H4 IA | 228 | 48 | 35.98 | 3 | <0.001 | 0.741 | 5.57 [2.40-12.96] | 1.23 [1.11-1.37] |
| Aldolase B | 235 | 49 | 26.66 | 3 | <0.001 | 0.697 | 1.69 [1.22-2.33] | 1.17 [1.06-1.28] |
| PCT | 235 | 49 | 23.57 | 3 | <0.001 | 0.698 | 1.66 [1.12-2.46] | 1.12 [1.02-1.22] |
| H2B + SAPS II | 235 | 49 | 83.39 | 4 | <0.001 | 0.839 | | |
| H4 + SAPS II | 235 | 49 | 82.29 | 4 | <0.001 | 0.834 | | |
| H2A + SAPS II | 235 | 49 | 80.74 | 4 | <0.001 | 0.830 | | |
| H3 + SAPS II | 235 | 49 | 79.27 | 4 | <0.001 | 0.835 | | |
| MR-proADM + SAPS II | 235 | 49 | 76.75 | 4 | <0.001 | 0.832 | | |
| H4 IA + SAPS II | 228 | 48 | 75.64 | 4 | <0.001 | 0.834 | | |
| Aldolase B + SAPS II | 234 | 49 | 70.32 | 4 | <0.001 | 0.809 | | |
| PCT + SAPS II | 234 | 49 | 68.47 | 4 | <0.001 | 0.811 | | |
| H2B + SOFA | 235 | 49 | 61.45 | 4 | <0.001 | 0.810 | | |
| H4 + SOFA | 235 | 49 | 60.08 | 4 | <0.001 | 0.804 | | |
| H4 IA + SOFA | 228 | 48 | 59.58 | 4 | <0.001 | 0.803 | | |
| MR-proADM + H2B | 235 | 49 | 59.50 | 4 | <0.001 | 0.804 | | |
| H2A + SOFA | 235 | 49 | 58.66 | 4 | <0.001 | 0.800 | | |
| H3 + SOFA | 235 | 49 | 58.44 | 4 | <0.001 | 0.800 | | |
| MR-proADM + H4 | 235 | 49 | 57.83 | 4 | <0.001 | 0.801 | | |
| MR-proADM + SOFA | 235 | 49 | 57.26 | 4 | <0.001 | 0.800 | | |
| MR-proADM + H2A | 235 | 49 | 56.25 | 4 | <0.001 | 0.796 | | |
| MR-proADM + H3 | 235 | 49 | 55.10 | 4 | <0.001 | 0.795 | | |
| MR-proADM + H4 IA | 228 | 48 | 52.66 | 4 | <0.001 | 0.780 | | |
| Aldolase B + SOFA | 234 | 49 | 51.39 | 4 | <0.001 | 0.781 | | |
| PCT + SOFA | 234 | 49 | 50.77 | 4 | <0.001 | 0.778 | | |
| MR-proADM + Aldolase B | 234 | 49 | 49.84 | 4 | <0.001 | 0.780 | | |
| PCT + H2B | 234 | 49 | 46.55 | 4 | <0.001 | 0.769 | | |
| MR-proADM + PCT | 234 | 49 | 46.37 | 4 | <0.001 | 0.768 | | |
| H2B + Aldolase B | 234 | 49 | 46.13 | 4 | <0.001 | 0.765 | | |

TABLE 3

Table 3: Uni- and bivariable Cox regression analysis for 28 day mortality in all critically ill patients Seventy-four patients of a total number (n) of 235 critically ill patients had died by day 3 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4; H4 was also measured by an immunoassay (IA))

| Model | N | Events | L.R. $\chi^2$ | df | p-value | C index | HR [95% CI] per ... IQR | ... 2fold change |
|---|---|---|---|---|---|---|---|---|
| SAPS II | 235 | 74 | 76.19 | 3 | <0.001 | 0.776 | 4.19 [2.89-6.07] | |
| MR-proADM | 235 | 74 | 66.81 | 3 | <0.001 | 0.765 | 4.86 [3.05-7.73] | 2.06 [1.66-2.54] |
| SOFA | 235 | 74 | 59.04 | 3 | <0.001 | 0.753 | 3.33 [2.27-4.88] | |
| H2B | 235 | 74 | 58.04 | 3 | <0.001 | 0.752 | 2.40 [1.84-3.11] | 1.39 [1.26-1.54] |
| H4 | 235 | 74 | 53.89 | 3 | <0.001 | 0.742 | 2.28 [1.75-2.99] | 1.37 [1.23-1.51] |
| H2A | 235 | 74 | 53.09 | 3 | <0.001 | 0.742 | 2.11 [1.66-2.70] | 1.37 [1.24-1.52] |
| H4 IA | 228 | 70 | 48.71 | 3 | <0.001 | 0.734 | 6.04 [2.97-12.27] | 1.25 [1.14-1.36] |
| H3 | 235 | 74 | 45.95 | 3 | <0.001 | 0.720 | 3.33 [2.10-5.29] | 1.22 [1.13-1.32] |
| PCT | 235 | 74 | 33.87 | 3 | <0.001 | 0.689 | 1.90 [1.37-2.64] | 1.15 [1.07-1.24] |
| Aldolase B | 235 | 74 | 25.91 | 3 | <0.001 | 0.667 | 1.47 [1.11-1.95] | 1.12 [1.03-1.22] |
| H2B + SAPS II | 235 | 74 | 100.75 | 4 | <0.001 | 0.811 | | |
| H4 + SAPS II | 235 | 74 | 98.37 | 4 | <0.001 | 0.806 | | |
| H2A + SAPS II | 235 | 74 | 97.64 | 4 | <0.001 | 0.805 | | |
| MR-proADM + SAPS II | 235 | 74 | 97.47 | 4 | <0.001 | 0.810 | | |
| H3 + SAPS II | 235 | 74 | 93.05 | 4 | <0.001 | 0.801 | | |
| H4 IA + SAPS II | 228 | 70 | 90.73 | 4 | <0.001 | 0.804 | | |
| MR-proADM + H2B | 235 | 74 | 83.70 | 4 | <0.001 | 0.795 | | |
| PCT + SAPS II | 234 | 74 | 81.63 | 4 | <0.001 | 0.786 | | |
| MR-proADM + H4 | 235 | 74 | 81.25 | 4 | <0.001 | 0.792 | | |
| MRproADM + H2A | 235 | 74 | 80.39 | 4 | <0.001 | 0.789 | | |
| H2B + SOFA | 235 | 74 | 77.41 | 4 | <0.001 | 0.785 | | |
| MR-proADM + SOFA | 235 | 74 | 77.32 | 4 | <0.001 | 0.783 | | |
| Aldolase B + SAPS II | 234 | 74 | 77.24 | 4 | <0.001 | 0.774 | | |
| MR-proADM + H3 | 235 | 74 | 76.68 | 4 | <0.001 | 0.786 | | |
| MR-proADM + H4 IA | 228 | 70 | 76.13 | 4 | <0.001 | 0.784 | | |
| H4 + SOFA | 235 | 74 | 74.89 | 4 | <0.001 | 0.778 | | |
| H2A + SOFA | 235 | 74 | 74.08 | 4 | <0.001 | 0.776 | | |
| H4 IA + SOFA | 228 | 70 | 72.78 | 4 | <0.001 | 0.778 | | |
| H3 + SOFA | 235 | 74 | 71.09 | 4 | <0.001 | 0.770 | | |
| MR-proADM + Aldolase B | 234 | 74 | 68.19 | 4 | <0.001 | 0.771 | | |
| MR-proADM + PCT | 234 | 74 | 66.57 | 4 | <0.001 | 0.766 | | |
| PCT + SOFA | 234 | 74 | 62.80 | 4 | <0.001 | 0.756 | | |
| PCT + H2B | 234 | 74 | 62.73 | 4 | <0.001 | 0.757 | | |
| H2B + Aldolase B | 234 | 74 | 62.54 | 4 | <0.001 | 0.753 | | |
| Aldolase B + SOFA | 234 | 74 | 59.13 | 4 | <0.001 | 0.753 | | |

TABLE 4

Table 4: Univariable Cox regression analysis for 7 day mortality in critically ill patients with lower respiratory tract infection Twenty-seven patients of a total number (n) of 109 critically ill patients with lower respiratory tract infection had died by day 7 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4 was also measured by an immunoassay (IA))

| Model | N | Events | L.R. $\chi^2$ | df | p-value | C index | HR [95% CI] per ... IQR | ... 2fold change |
|---|---|---|---|---|---|---|---|---|
| SAPS II | 109 | 27 | 29.14 | 3 | <0.001 | 0.773 | 3.47 [1.86-6.49] | |
| H2B | 109 | 27 | 27.70 | 3 | <0.001 | 0.785 | 2.56 [1.59-4.12] | 1.39 [1.18-1.64] |
| H4 | 109 | 27 | 26.36 | 3 | <0.001 | 0.778 | 2.39 [1.49-3.84] | 1.36 [1.15-1.61] |
| H2A | 109 | 27 | 25.40 | 3 | <0.001 | 0.774 | 2.16 [1.40-3.33] | 1.35 [1.14-1.60] |
| H4 IA | 105 | 26 | 22.06 | 3 | <0.001 | 0.752 | 5.64 [1.66-19.13] | 1.23 [1.06-1.41] |
| SOFA | 109 | 27 | 21.84 | 3 | <0.001 | 0.742 | 2.72 [1.38-5.36] | 1.05 [1.02-1.09] |
| MR-proADM | 109 | 27 | 21.54 | 3 | <0.001 | 0.752 | 2.86 [1.37-5.94] | 1.67 [1.17-2.39] |
| H3 | 109 | 27 | 21.48 | 3 | <0.001 | 0.760 | 2.89 [1.36-6.13] | 1.19 [1.05-1.35] |
| Aldolase B | 109 | 27 | 17.16 | 3 | 0.001 | 0.721 | 1.49 [1.00-2.22] | 1.14 [1.00-1.29] |
| PCT | 109 | 27 | 14.81 | 3 | 0.002 | 0.716 | 1.47 [0.77-2.80] | 1.08 [0.95-1.22] |

TABLE 5

Table 5: Univariable Cox regression analysis for 28 day mortality in critically ill patients with urinary tract infection Thirty-four patients of a total number (n) of 94 critically ill patients with urinary tract infection had died by day 28 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4; H4 was also measured by an immunoassay (IA))

| Model | N | Events | L.R. $\chi^2$ | df | p-value | C index | HR [95% CI] per ... IQR | ... 2fold change |
|---|---|---|---|---|---|---|---|---|
| H2B | 94 | 34 | 25.79 | 3 | <0.001 | 0.764 | 2.52 [1.75-3.65] | 1.39 [1.22-1.59] |
| H4 | 94 | 34 | 25.46 | 3 | <0.001 | 0.761 | 2.47 [1.70-3.60] | 1.38 [1.21-1.58] |
| H3 | 94 | 34 | 24.98 | 3 | <0.001 | 0.756 | 4.52 [2.34-8.75] | 1.29 [1.15-1.44] |
| H2A | 94 | 34 | 24.65 | 3 | <0.001 | 0.759 | 2.32 [1.64-3.28] | 1.39 [1.21-1.59] |
| SAPS II | 94 | 34 | 23.69 | 3 | <0.001 | 0.737 | 3.00 [1.85-4.89] | |
| H4 IA | 90 | 31 | 22.52 | 3 | <0.001 | 0.751 | 8.43 [2.79-25.45] | 1.29 [1.13-1.47] |
| SOFA | 94 | 34 | 16.07 | 3 | 0.001 | 0.696 | 2.28 [1.39-3.76] | 1.05 [1.02-1.08] |

TABLE 5-continued

Table 5: Univariable Cox regression analysis for 28 day mortality in critically ill patients with urinary tract infection Thirty-four patients of a total number (n) of 94 critically ill patients with urinary tract infection had died by day 28 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4; H4 was also measured by an immunoassay (IA))

| Model | N | Events | L.R. $\chi^2$ | df | p-value | C index | HR [95% CI] per ... IQR | ... 2fold change |
|---|---|---|---|---|---|---|---|---|
| MR-proADM | 94 | 34 | 14.93 | 3 | 0.002 | 0.689 | 2.28 [1.36-3.81] | 1.65 [1.21-2.25] |
| Aldolase B | 94 | 34 | 11.96 | 3 | 0.008 | 0.679 | 1.82 [1.19-2.78] | 1.18 [1.05-1.33] |
| PCT | 94 | 34 | 5.54 | 3 | 0.136 | 0.594 | 1.30 [0.74-2.29] | 1.05 [0.94-1.17] |

TABLE 6

Table 6: Univariable Cox regression analysis for 7 day mortality in critically ill patients with malignancies Sixteen patients of a total number (n) of 64 critically ill patients with malignancies had died by day 7 after ICU admission (events). Scores or biomarkers measured on ICU admission are included in the models. All univariable or bivariable models are adjusted for age and sex. The degrees of freedom (df) reflect the number of variables and adjustments included. Displayed results are the Likelihood-Ratio-$\chi^2$ test (L.R. $\chi^2$ and p-value), C index (Harrel) and standardized hazard ratios (HR) plus 95% confidence interval (CI), either per interquartile range (IQR) or 2fold change. (SAPS II: simplified acute physiology score II; SOFA: sequential organ failure assessment MR-proADM: midregional proadrenomedullin; PCT: procalcitonin; Histones are represented by histone H2A, H2B, H3 and H4. H4 was also measured by an immunoassay (IA))

| Model | N | Events | L.R. $\chi^2$ | df | p-value | C index | HR [95% CI] per ... IQR | ... 2fold change |
|---|---|---|---|---|---|---|---|---|
| H2B | 64 | 16 | 22.32 | 3 | <0.001 | 0.815 | 4.79 [2.44-9.43] | 1.60 [1.31-1.96] |
| H2A | 64 | 16 | 22.28 | 3 | <0.001 | 0.811 | 4.35 [2.31-8.20] | 1.61 [1.31-1.98] |
| H4 | 64 | 16 | 21.99 | 3 | <0.001 | 0.812 | 4.53 [2.33-8.81] | 1.60 [1.30-1.97] |
| H4 IA | 61 | 16 | 21.95 | 3 | <0.001 | 0.803 | 5.52 [2.24-13.58] | 1.64 [1.26-2.13] |
| H3 | 64 | 16 | 17.59 | 3 | 0.001 | 0.767 | 7.95 [2.70-23.45] | 1.40 [1.17-1.67] |
| SAPS II | 64 | 16 | 15.16 | 3 | 0.002 | 0.755 | 4.76 [1.99-11.38] | 1.02 [1.01-1.03] |
| MR-proADM | 64 | 16 | 10.20 | 3 | 0.017 | 0.737 | 3.15 [1.38-7.17] | 1.88 [1.20-2.96] |
| SOFA | 64 | 16 | 9.84 | 3 | 0.020 | 0.722 | 3.36 [1.42-7.95] | 1.06 [1.02-1.11] |
| Aldolase B | 64 | 16 | 7.30 | 3 | 0.063 | 0.644 | 2.05 [1.15-3.64] | 1.25 [1.05-1.50] |
| PCT | 64 | 16 | 4.75 | 3 | 0.191 | 0.661 | 1.95 [0.92-4.14] | 1.15 [0.98-1.34] |

Example 2: Superior Accuracy of Proadrenomedullin for Mortality Prediction in Sepsis with Varying Levels of Illness Severity Background: the use of novel sepsis biomarkers has increased in recent years. However, their prognostic value with respect to illness severity has not been explored. In this work, we examined the ability of mid-regional proadrenomedullin (MR-proADM) in predicting mortality in sepsis patients with different degrees of organ failure, compared to that of procalcitonin, C-reactive protein and lactate.

Methods: this was a two-centre prospective observational cohort, enrolling severe sepsis or septic shock patients admitted to the ICU. Plasma biomarkers were measured during the first 12 hours of admission. The association between biomarkers and 28 day mortality was assessed by Cox regression analysis and Kaplan-Meier curves. Patients were divided into three groups as evaluated by the Sequential Organ Failure Assessment (SOFA) score. The accuracy of the biomarkers for mortality was determined by area under the receiver operating characteristic curve (AUROC) analysis.

Results: 326 patients with severe sepsis (21.7%) or septic shock (79.3%) were enrolled with a 28 day mortality rate of 31.0%. Only MR-proADM and lactate were associated with mortality in the multivariate analysis: hazard ratio (HR): 8.5 vs. 3.4 (p<0.001). MR-proADM showed the best AUROC for mortality prediction at 28 days in the analysis over the entire cohort (AUROC [95% CI]: 0.79 [0.74-0.84]) (p<0.001). When patients were stratified by the degree of organ failure, MR-proADM was the only biomarker to predict mortality in all severity groups (SOFA≤6, SOFA=7-12, and SOFA≥13), AUROC [95% CI] of 0.75 [0.61-0.88], 0.74 [0.66-0.83] and 0.73 [0.59-0.86] respectively (p<0.05). All patients with MR-proADM concentrations ≤0.88 nmol/L survived up to 28 days. In patients with SOFA≤6, the addition of MR-proADM to the SOFA score increased the ability of SOFA to identify non-survivors, AUROC [95% CI]: 0.70 [0.58-0.82] and 0.77 [0.66-0.88] respectively (p<0.05 for both).

Conclusions: the performance of prognostic biomarkers in sepsis is highly influenced by disease severity. MR-proADM accuracy to predict mortality is not affected by the degree of organ failure. In consequence, it is a good candidate in the early identification of sepsis patients with moderate disease severity but at risk of mortality.

Background

Sepsis remains the primary cause of death in intensive care unit (ICU) patients despite improvements in antibiotic and early hemodynamic management. In Europe, sepsis occurrence in acutely ill patients results in an ICU mortality rate ranging between 27% and 54% depending on the severity [1]. In the United States, the Centre for Disease Control estimates that 500,000 people develop sepsis and 200,000 die each year [2] [3]. The prompt diagnosis and assessment of high risk sepsis patients is therefore highly desirable, increasing the possibility of initiating early and specific treatments. Thus, clinical severity scores such as Sequential Organ Failure Assessment (SOFA) score can play a critical role [4]. However, the isolated use of these scoring systems to guide decision-making in sepsis has been heavily criticized [5]. A standardized assessment tool for the early identification of sepsis patients upon admission with a range of severity levels would be of dramatic value in aiding clinical decision making and optimizing the use of health care resources. Accordingly, a number of prognostic biomarkers have been proposed in the field of sepsis over the last decades-many more than in other diseases. Most of these molecules are hormones, cytokines or circulating proteins related to inflammation or the coagulation system and may require considerable time, effort and costs to be measured [6].

Adrenomedullin (ADM) is a peptide which can act as a hormone, and is produced by multiple tissues during physiologic and infectious stress with varying physiological functions, including vasodilatory, anti-inflammatory and antimicrobial activity, which is further enhanced by its regulation and modulation of complement activity [7]. Thus, ADM is considered a "hormokine", characterized by a hormone-like behavior in non-inflammatory conditions when it is only produced by endocrine cells, and by a cytokine-like behavior in sepsis when it is ubiquitously hyper-expressed. Moreover, exogenous ADM has been shown to reduce acute lung injury, vascular permeability and death in animal models of sepsis; whilst endogenous over-expression similarly ameliorates the sepsis insult [8] [9]. Measurement of circulating ADM is complicated by a rapid degradation and clearance from the circulation, and is further masked by a binding protein (complement factor H), preventing its detection by standard immunoassay. The mid-regional fragment of pro-adrenomedullin (MR-proADM), comprising of amino acids 45-92, is more stable and directly reflects levels of the rapidly degraded active ADM peptide [10]. Increased MR-proADM concentrations have been identified in the plasma of patients with community acquired pneumonia (CAP) and are widely used in the risk and severity assessment of the condition [11] [12] [13]. However, little data is available for severe sepsis and septic shock patients. Additionally, the influence of disease severity on the performance of prognostic biomarkers in sepsis has not been appropriately studied yet.

In this study, we aimed to evaluate the ability of MR-proADM levels to predict 28 day mortality in sepsis patients, compared to other standard biomarkers (procalcitonin (PCT), C-reactive protein (CRP), and lactate), in three different levels of disease severity as measured by the SOFA score.

Methods

Patients, inclusion and exclusion criteria: this study was a prospective observational cohort of patients recruited consecutively from two intensive care units (ICU) in Spain and France. Adult patients with age ≥18 years and admitted to the ICU from April 2013 to January 2016 were enrolled within 12 hours after meeting criteria for severe sepsis or septic shock, based on the SEPSIS-2 definition by the American College of Chest Physicians/Society of Critical Care Medicine Consensus Conference [14]. Enrolled patients also had SOFA score ≥2 and therefore met criteria for the new SEPSIS-3 definition for sepsis [15]. Patients with human immunodeficiency virus (HIV) infection and those undergoing radiotherapy or receiving immunosuppressive drugs, including chemotherapy or systemic steroids, in the last 3 months prior to admission to the ICU were considered to be immunosuppressed. Exclusion criteria were age <18 years, the presence of pregnancy, the absence of a blood sample available for biomarker profiling within the first 12 hours following ICU admission, or lack of informed consent. Clinical data recorded from the medical records included demographics, comorbidities, laboratories, microbiology, and biomarker levels. The severity of illness was assessed on admission by calculating the Sequential Organ Failure Assessment (SOFA) score.

Biomarker Evaluation

Plasma samples for biomarker profiling were collected as close as possible to the moment of ICU admission, and always within the first 12 hours. Plasma MR-proADM measurement was performed by TRACE technology (Time Resolved Amplified Cryptate Emission) using a new sandwich immunoassay (Kryptor Compact Plus Analyser, BRAHMS, Hennigsdorf, Germany); limit of detection 0.05 nmol/L. PCT measurement was performed by electrochemiluminescence immunoassay (ECLIA) on a chemistry analyser (Cobas 6000, Roche Diagnostics, Meylan, France); limit of detection 0.02 ng/ml. Serum CRP and lactate were measured by particle-enhanced immunoturbidimetric and colorimetric assay respectively (e501 Module Analyser, Roche Diagnostics, Meylan, France); limit of detection 0.15 mg/dL and 0.2 mmol/L respectively.

Statistical Analysis

Differences in demographic and clinical characteristics between survivors and non-survivors were assessed using the $\chi 2$ test for categorical variables. Student's t-test or Mann-Whitney U test were respectively used to compare continuous variables based upon the presence or absence of normal distribution. The association between biomarkers and the risk of mortality was assessed by Cox regression analysis, adjusted by confounding variables. Time was censored at 28 days following admission to the ICU. The first 24 hours of ICU admission was considered as day 1 in the analysis. Variables yielding a p<0.05 in the univariate regression analysis were further included in the multivariate analysis. Biomarkers were log transformed in order to reach a normal distribution. The impact of biomarkers on mean survival time was assessed by using Kaplan-Meier curves and the Mantel-Haenszel log-rank test. Similar to the Cox regression analysis, time was censored at 28 days following admission to the ICU. Accuracy and predictive values of the biomarkers for mortality were evaluated by calculating the area under the receiver operating characteristic (AUROC) curve. Patients were distributed into three groups depending on disease severity as assessed by the SOFA score using two predefined cut-offs, one with a sensitivity close to 90% and the other showing a specificity close to 90% for detecting non-survivors at 28 days (FIG. 4). Data were analyzed by using the IBM SPSS 20.0 software (SPSS, Chicago, Ill.).

Results

Patient characteristics and biomarker concentrations: Three hundred and twenty six patients (326) with severe sepsis (21.7%) or septic shock (79.3%) were enrolled with a 28 day mortality rate of 25.5% and 34.9% in Valladolid and Dijon respectively, and an overall mortality rate of 31.0% across both sites (Table 7). The median age was 65 years and 54.3% of patients were male. Compared to survivors, non-survivors were older and presented with higher SOFA scores, and an increased incidence of septic shock, mechanical ventilation, renal replacement therapy, neoplasia, cardiovascular disease, chronic renal failure, immunosuppression, and respiratory disease (all p<0.05). The most common source of infection was of respiratory and urologic origin, regardless of outcome. Mortality rates depending on the source of infection were as follows: 37.2% in patients suffering from a respiratory infection, 32.4% in those with an urological infection, 28.6% in patients with an abdominal infection, 35.5% in those showing a primary or secondary bacteremia and 25.6% in those patients with an infection of other origin. Regarding microbiological identification, both survivors and non-survivors showed a balanced presence of Gram−, Gram+ and virus pathogens. Fungal infections were more frequent in non-survivors. The most common cause of death was multi-organ dysfunction syndrome (n=58; 57.4%), followed by refractory shock (n=9, 8.9%) and refractory hypoxemia (n=8, 7.9%). A limitation of therapeutic effort was applied to 21 patients. MR-proADM, PCT and lactate concentrations were all significantly elevated in non-surviving patients compared to survivors (all p<0.01), whereas CRP levels remained similar in both groups. Levels of MR-proADM depending on the source of infection were as follows [median (interquartile range)]: respiratory infection [3.6 nmol/L (5.6)], urological infection [4.6 nmol/L (5.4)], abdominal infection [4.9 nmol/L (6.5)], bacteriemia [3.8 nmol/L (5.1)], and [3.5 nmol/L (5.8)] in infections of other origin. Levels of MR-proADM depending on the infecting microbe were [median (interquartile range)]: fungal infection [6.1 nmol/L (5.6)], Gram−bacteria [4.9 nmol/L (5.9)], Gram+bacteria [4.1 nmol/L (6.2)] or viruses [1.2 nmol/L (3.4)].

TABLE 7

Clinical characteristics of the patients: Data are presented as mean (S.D.) or median (IQR) where appropriate. Values expressed in percentages (%) indicate the proportion of survivors and non-survivors at 28 days for specific variables.

|  | Survivors n = 225 | Non-survivors n = 101 | Total n = 326 | p |
|---|---|---|---|---|
| Patients from Valladolid (n, %) | 102 (45.3%) | 35 (34.7%) | 137 | 0.071 |
| Patients from Dijon (n, %) | 123 (54.7%) | 66 (65.3%) | 189 |  |
| Male (n, %) | 133 (59.1%) | 68 (67.3%) | 201 (61.4%) | 0.098 |
| Age (years) (mean, SD) | 63 (14) | 69 (12) | 65.4 (14) | <0.001 |
| SOFA (mean, SD) | 8 (3.4) | 11 (3.5) | 9 (3.7) | <0.001 |
| Septic shock (n, %) | 152 (67.5%) | 87 (86.1%) | 239 (73.3%) | 0.020 |
| Mechanical ventilation (n, %) | 150 (66.7%) | 89 (88.1%) | 239 (73.3%) | <0.001 |
| RRT (n, %) | 40 (17.7%) | 45 (44.6%) | 85 (26.2%) | <0.001 |
| ICU stay (days) (mean, SD) | 12.9 (18) | 7.7 (6.7) | 11.2 (15.6) | 0.012 |
| Neoplasia (n, %) | 47 (21%) | 35 (34.7%) | 82 (25.2%) | 0.007 |
| Diabetes (n, %) | 58 (25.8%) | 29 (28.7%) | 87 (26.7%) | 0.330 |
| COPD (n, %) | 33 (14.7%) | 16 (15.8%) | 49 (15%) | 0.450 |
| Cardiovascular disease (n, %) | 56 (25%) | 41 (40.6%) | 97 (29.8%) | 0.030 |
| Chronic renal failure (n, %) | 16 (7.1%) | 16 (15.8%) | 32 (9.8%) | 0.014 |
| Immunosuppression (n, %) | 21 (9.3%) | 25 (24.8%) | 46 (14.1%) | <0.001 |
| Respiratory infection (n, %) | 98 (43.6%) | 58 (57.4%) | 156 (48%) | 0.014 |
| Urologic infection (n, %) | 75 (33.3%) | 36 (35.6%) | 111 (34%) | 0.380 |
| Abdominal infection (n, %) | 25 (11.1%) | 10 (9.9%) | 35 (10.7%) | 0.450 |
| Other infection (n, %) | 32 (14%) | 11 (10.9%) | 43 (13%) | 0.40 |
| Primary or secondary bacteremia (n, %) | 69 (30.7%) | 38 (37.6%) | 107 (32.8%) | 0.130 |
| Gram − bacteria (n, %) | 62 (27.6%) | 28 (27.7%) | 90 (27.6%) | 0.975 |
| Gram + bacteria (n, %) | 47 (20.9%) | 22 (21.8%) | 69 (21.2%) | 0.855 |
| Fungi (n, %) | 3 (1.3%) | 5 (5%) | 8 (2.5%) | 0.050 |
| Virus (n, %) | 15 (6.7%) | 5 (5%) | 20 (6.1%) | 0.550 |
| MR-proADM (nmol/L) (median, IQR) | 2.68 (3.56) | 7.44 (6.84) | 3.62 (5.6) | <0.001 |
| Lactate (mmol/L) (median, IQR) | 2.00 (1.54) | 3.60 (5.53) | 2.12 (2.28) | <0.001 |
| CRP (mg/dl) (median, IQR) | 147.8 (193.6) | 163.0 (181.9) | 155.0 (189) | 0.200 |
| PCT (ng/ml) (median, IQR) | 2.9 (17.5) | 5.8 (36.7) | 3.54 (27.5) | 0.001 |

Survival Analysis

MR-proADM, PCT and lactate showed a significant association with mortality in the univariate Cox regression analysis (Table 8). After adjusting for confounders and compared to PCT, CRP, and lactate, MR-proADM showed the strongest independent association with the risk of mortality (hazard ratio: 8.5; 95% confidence interval: 4.2-17.4; p<0.001) (Table 8). In addition, Kaplan Meier analysis showed that no patients with a MR-proADM value ≤0.88 nmol/L died in the first 28 days following ICU admission (FIG. 1). This cut-off was selected since it provided a sensitivity of 100% in identifying non-survivors in the AUROC (FIG. 2).

TABLE 8

Uni and multivariate Cox regression analysis for mortality prediction at 28 days following ICU admission.

|  | Univariate | | Multivariate | |
| --- | --- | --- | --- | --- |
|  | HR (95% CI) | p | HR (95% CI) | p |
| MR-proADM | 11.2 (6.3-19.8) | <0.001 | 8.5 (4.2-17.4) | <0.001 |
| Lactate | 3.8 (2.6-5.5) | <0.001 | 3.4 (2.0-5.8) | <0.001 |
| CRP | 1.3 (0.8-1.9) | 0.266 | — | — |
| PCT | 1.4 (1.2-1.8) | 0.001 | 1.1 (0.9-1.4) | 0.326 |
| SOFA | 1.2 (1.2-1.3) | <0.001 | 1.2 (1.1-1.3) | <0.001 |

Adjusting variables were: age, septic shock, cardiovascular disease, immunosupression, chronic renal failure, neoplasia, respiratory source of infection, renal replacement therapy, hospital (Valladolid/Dijon), presence of fungal infection, limitation of therapeutic effort The Influence of Disease Severity on Biomarker Performance MR-proADM showed the best AUROC for mortality prediction at 28 days in the analysis over the entire cohort, even better than that of SOFA score (FIG. 2). When patients were stratified by the degree of organ failure, MR-proADM was the only biomarker able to discriminate non-survivors from survivors at 28 days in those patients with the lowest degree of disease severity (SOFA score 6), (AUROC [95% confidence interval (95% CI):]: 0.75 [0.61-0.88]), (p=0.006) (FIG. 3). In the moderately severe patients (SOFA score 7-12), MR-proADM showed a higher AUROC than that observed with lactate (0.74 [0.66-0.83] vs. 0.61 [0.52-0.71] respectively) (FIG. 3). In the most severe patients (SOFA score≥13), MR-proADM and lactate had a similar AUROC (0.73 [0.59-0.86] vs. 0.72 [0.59-0.86] respectively) (FIG. 3). Neither CRP not PCT were predictive of 28 day mortality in any severity group based on the SOFA score.

The threshold values (cut-off) of MR-proADM for identifying non-survivors were those showing the highest specificity from those with a pre-fixed sensitivity of at least 0.80. For patients with SOFA scores ≤6, 7-12, and ≥13, the MR-proADM cut-off was 1.79, 3.25, and 5.58 nmol/L respectively (Table 9).

TABLE 9

MR-proADM cut-off (nmol/L) with the highest accuracy for predicting 28 day mortality based on SOFA score. PPV—positive predictive value, NPV—negative predictive value, +LR—positive likelihood ratio, −LR—negative likelihood ratio.

|  | Cut-off | Sensitivity | Specificity | PPV | NPV | +LR | −LR |
| --- | --- | --- | --- | --- | --- | --- | --- |
| SOFA ≤6 | 1.79 | 83.0 | 61.0 | 23.8 | 96.2 | 2.14 | 0.27 |
| SOFA 7-12 | 3.25 | 83.0 | 52.0 | 43.4 | 87.0 | 1.74 | 0.33 |
| SOFA ≥13 | 5.58 | 83.8 | 60.0 | 75.6 | 71.4 | 2.09 | 0.27 |

The length of ICU stay in each severity group was [mean, (SD)]: SOFA ≤6: 11.0 days (18.3); SOFA 7-12: 12.4 days (16.0); SOFA 13: 8.4 days (7.6). The mortality rates for each severity group 12.8%, 30.6% and 59.7% respectively.

MR-proADM Improves Mortality Prediction in the Less Severely Ill Patients

We evaluated the combination of MR-proADM and SOFA score in predicting mortality, such that patients with MR-proADM concentrations >1.79 nmol/L were considered to have a 1 point increase in the SOFA score. In patients with SOFA≤6, the MR-proADM modified SOFA score (ADM-SOFA) showed an increased ability to identify non-survivors compared to SOFA alone, AUROC [95% CI]: SOFA 0.70 [0.58-0.82] and ADM-SOFA 0.77 [0.66-0.88].

Discussion

Severity in sepsis depends on the extent of organ failure as evaluated by the SOFA score, which in turn is directly associated with the risk of mortality [15]. Nonetheless, the emergence of an increasing number of biomarkers may provide a new avenue with which to improve prognostic accuracy in a simple and fast manner. In this regard, our study suggests that MR-proADM may be a promising biomarker. However, previous studies evaluating the prognostic role of MR-proADM in sepsis have provided conflicting results. Christ-Crain et al found that MR-proADM yielded an AUROC of 0.81 for detecting ICU mortality in a group of 53 patients with sepsis [16]. In contrast, Suberviola et al found limited value of MR-proADM for predicting hospital mortality in 137 sepsis patients, with an AUROC of 0.62 [17]. Yet Marino et al showed that in 101 patients with sepsis, severe sepsis or septic shock, plasma adrenomedullin was strongly associated with the severity of disease, vasopressor requirement and 28 day mortality [18]. These divergent results on the prognostic role of MR-proADM may be explained by differences in patient characteristics, disease severity, infectious source, surgical vs. medical and small sample sizes across the various studies.

In the present study, we demonstrated for the first time that the performance of biomarkers to predict mortality in sepsis strongly depends on the degree of organ failure upon ICU admission. Stratifying patients based on their SOFA score allowed us to demonstrate that MR-proADM was the only biomarker able to identify non-survivors in all the severity groups. This is particularly important for the less severely ill patients (SOFA score ≤6), since this group represents either the earliest presentation in the clinical course of sepsis and/or the less severe form of this disease in the ICU setting. Thus, MR-proADM may be a good candidate to be incorporated in an early sepsis management protocol, since it could provide a rapid prognostic value and help to guide diagnostic interventions and treatment decisions, thus resembling the role of troponin in myocardial infarction or d-dimer in pulmonary embolism. The cut-off value of MR-proADM identified for this group of patients (1.79 nmol/L) could be very useful to this regard. This cut-off is able to detect mortality with a good sensitivity and a high negative predictive value. Finally, MR-proADM could help stratify patients in clinical trials examining novel therapies for sepsis.

MR-proADM showed greater predictive values for the risk of mortality than other more commonly used biomarkers, including lactate, in patients with an intermediate degree of organ failure (SOFA score 7-12). In contrast, both MR-proADM and lactate performed similarly in the most severe patients (SOFA≥13). Therefore, our results support the importance of considering the degree of organ failure when designing studies for the discovery of prognostic biomarkers in sepsis.

The assessment of organ failure by using the SOFA score was recently proposed by the SEPSIS-3 consensus to identify high risk patients with suspected infection [15]. Our results show that a "positive" MR-proADM value may improve the ability of SOFA to predict mortality in sepsis. Interestingly, a combination of MR-proADM with clinical scores such as PSI or CURB-65 also performed better than the clinical scores alone in patients with Community Acquired Pneumonia (CAP) or lower respiratory tract infections (LRTI) [12] [19] [20] [21]. As a result, MR-proADM could be used as a reliable risk-stratification tool with the ability to predict mortality or adverse events and to guide clinical decisions. Further clinical studies evaluating strategies combining MR-proADM with other classical severity scores and/or biomarkers for improving the recognition and prognostication of sepsis are therefore warranted [22] [23].

Finally, we observed that an MR-proADM value lower than 0.88 nmol/L may allow to "rule out" mortality in the 28 days following admission to the ICU. This cut-off may be especially useful for guiding early clinical decisions, when the clinical signs of overt organ failure are not yet apparent.

MR-proADM monitoring over time may further illustrate a temporal trend, which can indicate the success of specific treatments and therapies and consequently increase its outcome predictive value [25]. Finally, in our cohort, MR-proADM levels slightly differed depending on the source of infection. Fungal infections induced the highest levels of MR-proADM, while viral infection induced the lowest. This is probably related to the fact that fungal infections resulted in a higher disease severity (median SOFA score of 12 vs. 9 points in patients with no fungal infection), while viral infections resulted in a milder disease severity (median SOFA score 6.5 vs. 9 points in patients with no viral infection).

Conclusions

Our results demonstrate that the performance of biomarkers in determining the risk of mortality in sepsis is influenced by disease severity. In patients with moderate severity, MR-proADM outperformed other standard biomarkers. As a consequence, MR-proADM may aid the early identification of sepsis patients requiring urgent ICU admission as well as facilitating the subsequent clinical management of these patients.

List of Abbreviations

ADM: Adrenomedullin
MR-proADM: Mid-regional proadrenomedullin
CRP: C-reactive protein
PCT: Procalcitonin
SOFA: Sequential Organ Failure Assessment Score
CI: Confidence Interval
AUROC: Area Under Receiver Operating Characteristics
PPV: Positive Predictive Value
NPV: Negative Predictive Value
LR: Likelihood ratio
HR: Hazard ratio
PSI: Pneumonia Severity Index
RRT: Renal Replacement Therapy All references cited herein are fully incorporated by reference.

Albrich, W. C. and S. Harbarth (2015). "*Intensive Care Med* 41(10): 1739-1751.
Bone, R. C., R. A. Balk, et al. (1992). *Chest* 101(6): 1644-1655.
Bouch, D. C. and J. P. Thompson (2008). *Continuing Education in Anaesthesia, Critical Care & Pain* 8(5): 181-185.
Breslow, M. J. and O. Badawi (2012). *Chest* 141(1): 245-252.
Ferreira, A. M. and Y. Sakr (2011). *Semin Respir Crit Care Med* 32(5): 543-551.
Fine, M J; Auble, T E; Yealy, D M; Hanusa, B H; Weissfeld, L A; Singer, D E; Coley, C M; Marrie, T J;
Kapoor, W N; et al. (1997). *N Engl J Med.* 336 (4): 243-250
Hodkinson, H M (1972). *Age and Ageing* 1 (4): 233-8
Halpern, N. A. and S. M. Pastores (2010). *Crit Care Med* 38(1): 65-71.
Kaneko-Wada Fde, J., G. Dominguez-Cherit, et al. (2015). *Gac Med Mex* 151(5): 628-634.
Le Gall, J. R., S. Lemeshow, et al. (1993). *JAMA* 270(24): 2957-2963.
Lim W S, van der Eerden M M, Laing R, et al. (2003). *Thorax.* 58 (5): 377-82
Mayr, V. D., M. W. Dunser, et al. (2006). *Crit Care* 10(6): R154.
Vincent, J. L. (2008). *Langenbecks Arch Surg* 393(6): 817-824.
Vincent, J. L., R. Moreno, et al. (1996). *Intensive Care Med* 22(7): 707-710.

References for Example 2 and the specification:

1. Vincent J-L. Clinical sepsis and septic shock-definition, diagnosis and management principles. Langenbecks Arch. Surg. Dtsch. Ges. Fur Chir. 2008; 393:817-24.
2. Jean-Baptiste E. Cellular mechanisms in sepsis. J. Intensive Care Med. 2007; 22:63-72.
3. Hoyert D L, Xu J. Deaths: preliminary data for 2011. Natl. Vital Stat. Rep. Cent. Dis. Control Prev. Natl. Cent. Health Stat. Natl. Vital Stat. Syst. 2012; 61:1-51.
4. Vincent J L, Moreno R, Takala J, Willatts S, De Mendonca A, Bruining H, et al. The SOFA (Sepsis-related Organ Failure Assessment) score to describe organ dysfunction/failure. On behalf of the Working Group on Sepsis-Related Problems of the European Society of Intensive Care Medicine. Intensive Care Med. 1996; 22:707-10.
5. Vincent J-L, Opal S M, Marshall J C. Ten reasons why we should NOT use severity scores as entry criteria for clinical trials or in our treatment decisions. Crit. Care Med. 2010; 38:283-7.
6. Pierrakos C, Vincent J-L. Sepsis biomarkers: a review. Crit. Care Lond. Engl. 2010; 14:R15.
7. Hirata Y, Mitaka C, Sato K, Nagura T, Tsunoda Y, Amaha K, et al. Increased circulating adrenomedullin, a novel vasodilatory peptide, in sepsis. J. Clin. Endocrinol. Metab. 1996; 81:1449-53.
8. Müller-Redetzky H C, Will D, Hellwig K, Kummer W, Tschernig T, Pfeil U, et al. Mechanical ventilation drives pneumococcal pneumonia into lung injury and sepsis in mice: protection by adrenomedullin. Crit. Care Lond. Engl. 2014; 18:R73.

9. Pugin J. Adrenomedullin: a vasodilator to treat sepsis? Crit. Care Lond. Engl. 2014; 18:152.
10. Struck J, Tao C, Morgenthaler N G, Bergmann A. Identification of an Adrenomedullin precursor fragment in plasma of sepsis patients. Peptides. 2004; 25:1369-72.
11. Huang D T, Angus D C, Kellum J A, Pugh N A, Weissfeld L A, Struck J, et al. Midregional proadrenomedullin as a prognostic tool in community-acquired pneumonia. Chest. 2009; 136:823-31.
12. Albrich W C, Dusemund F, Ruegger K, Christ-Crain M, Zimmerli W, Bregenzer T, et al. Enhancement of CURB65 score with proadrenomedullin (CURB65-A) for outcome prediction in lower respiratory tract infections: derivation of a clinical algorithm. BMC Infect. Dis. 2011; 11:112.
13. Kruger S, Ewig S, Giersdorf S, Hartmann O, Suttorp N, Welte T, et al. Cardiovascular and inflammatory biomarkers to predict short- and long-term survival in community-acquired pneumonia: Results from the German Competence Network, CAPNETZ. Am. J. Respir. Crit. Care Med. 2010; 182:1426-34.
14. Bone R C, Balk R A, Cerra F B, Dellinger R P, Fein A M, Knaus W A, et al. Definitions for sepsis and organ failure and guidelines for the use of innovative therapies in sepsis. The ACCP/SCCM Consensus Conference Committee. American College of Chest Physicians/Society of Critical Care Medicine. 1992. Chest. 2009; 136:e28.
15. Singer M, Deutschman C S, Seymour C W, Shankar-Hari M, Annane D, Bauer M, et al. The Third International Consensus Definitions for Sepsis and Septic Shock (Sepsis-3). JAMA. 2016; 315:801-10.
16. Christ-Crain M, Morgenthaler N G, Struck J, Harbarth S, Bergmann A, Müller B. Mid-regional pro-adrenomedullin as a prognostic marker in sepsis: an observational study. Crit. Care Lond. Engl. 2005; 9:R816-824.
17. Suberviola B, Castellanos-Ortega A, Ruiz Ruiz A, Lopez-Hoyos M, Santibanez M. Hospital mortality prognostication in sepsis using the new biomarkers suPAR and proADM in a single determination on ICU admission. Intensive Care Med. 2013; 39:1945-52.
18. Marino R, Struck J, Maisel A S, Magrini L, Bergmann A, Di Somma S. Plasma adrenomedullin is associated with short-term mortality and vasopressor requirement in patients admitted with sepsis. Crit. Care Lond. Engl. 2014; 18:R34.
19. Christ-Crain M, Morgenthaler N G, Stolz D, Müller C, Bingisser R, Harbarth S, et al. Pro-adrenomedullin to predict severity and outcome in community-acquired pneumonia [ISRCTN04176397]. Crit. Care Lond. Engl. 2006; 10:R96.
20. Courtais C, Kuster N, Dupuy A-M, Folschveiller M, Jreige R, Bargnoux A-S, et al. Proadrenomedullin, a useful tool for risk stratification in high Pneumonia Severity Index score community acquired pneumonia. Am. J. Emerg. Med. 2013; 31:215-21.
21. Renaud B, Schuetz P, Claessens Y-E, Labarère J, Albrich W, Mueller B. Proadrenomedullin improves Risk of Early Admission to ICU score for predicting early severe community-acquired pneumonia. Chest. 2012; 142:1447-54.
22. Guignant C, Voirin N, Venet F, Poitevin F, Malcus C, Bohé J, et al. Assessment of pro-vasopressin and pro-adrenomedullin as predictors of 28-day mortality in septic shock patients. Intensive Care Med. 2009; 35:1859-67.
23. Travaglino F, De Berardinis B, Magrini L, Bongiovanni C, Candelli M, Silveri N G, et al. Utility of Procalcitonin (PCT) and Mid regional pro-Adrenomedullin (M R-proADM) in risk stratification of critically ill febrile patients in Emergency Department (E D). A comparison with APACHE II score. BMC Infect. Dis. 2012; 12:184.
24. Bello S, Lasierra A B, Mincholé E, Fandos S, Ruiz M A, Vera E, et al. Prognostic power of proadrenomedullin in community-acquired pneumonia is independent of aetiology. Eur. Respir. J. 2012; 39:1144-55.
25. Andaluz-Ojeda D, Cicuéndez R, Calvo D, Largo E, Nogales L, Muñoz M F, et al. Sustained value of proadrenomedullin as mortality predictor in severe sepsis. J. Infect. 2015; 71:136-9.

The invention claimed is:

1. A method for detecting proadrenomedullin (proADM) in a subject in need thereof, the method comprising:
   contacting a sample obtained from the subject with a first anti-proADM antibody, antigen-binding fragment;
   detecting binding between proADM and the first anti-proADM antibody, antigen-binding fragment;
   determining the level of proADM in the sample;
   determining the sequential organ failure assessment (SOFA) score of the subject; and
   if the SOFA score is ≤6, then determining whether the proADM level is >1.8 nmol/L.

2. The method of claim 1, wherein said level of proADM is determined using a method selected from the group consisting of mass, luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, and rare cryptate assay.

3. The method of claim 2, wherein the method is an immunoassay and wherein the assay is performed in homogeneous phase or in heterogeneous phase.

4. The method of claim 3, wherein the contacting further comprises contacting the sample with a second anti-proADM antibody, antigen-binding fragment or; and
   detecting the binding of the first and second anti-proADM antibodies or antigen-binding fragments to proADM.

5. The method of claim 4, wherein one of the first or second anti-proADM antibodies is labeled and the other antibody is bound to, or is capable of being selectively bound to a solid phase.

6. The method of claim 4, wherein the first anti-proADM antibody and the second anti-proADM antibody are present dispersed in a liquid reaction mixture, and wherein a first labelling component which is part of a labelling system based on fluorescence or chemiluminescence extinction or amplification is bound to the first anti-proADM antibody, and a second labelling component of said labelling system is bound to the second anti-proADM antibody so that, after binding of both anti-proADM antibodies to said proADM to be detected, a measurable signal which permits detection of the resulting sandwich complexes in the measuring solution is generated.

7. The method of claim 6, wherein the labelling system comprises a rare earth cryptate or chelate in combination with a fluorescent or chemiluminescent dye, optionally of the cyanine type.

8. The method of claim 1, wherein if the SOFA score is ≤6, then determining whether the proADM level is >0.88 nmol/L.

9. The method of claim 1, further comprising diagnosing the subject as having an increased risk of an adverse event within 28 days from when the sample was obtained, where said adverse event is selected from the group consisting of:
- organ dysfunction; multiple organ dysfunctions; organ failure; multiple organ failure; life-threatening infection; mortality; and life-threatening progression of a disease or disorder, said disease or disorder selected from the group consisting of:
- respiratory disease; urinary tract infection; inflammatory response related to infective and non-infective etiologies; systemic inflammatory response syndrome (SIRS); sepsis; severe sepsis; septic shock; organ failure(s); cardiovascular disease;
- hematologic disease; disseminated coagulation; diabetes mellitus; malignancy;
- liver disease; renal disease; immunodepression; viral infection; fungal infection;
- bacterial infection; gram-negative bacterial infection; gram-positive bacterial infection; abdominal infection; and immunosuppression.

\* \* \* \* \*